(12) United States Patent
Gunde et al.

(10) Patent No.: US 10,975,143 B2
(45) Date of Patent: Apr. 13, 2021

(54) ANTI-TNF-α-ANTIBODIES AND FUNCTIONAL FRAGMENTS THEREOF

(71) Applicant: Tillotts Pharma AG, Rheinfelden (CH)

(72) Inventors: Tea Gunde, Zurich (CH); Sebastian Meyer, Eggenwil (CH); Esther Maria Furrer, Rheinfelden (CH)

(73) Assignee: Tillotts Pharma AG, Rheinfelden (CH)

( * ) Notice: Subject to any disclaimer, the term of this patent is extended or adjusted under 35 U.S.C. 154(b) by 290 days.

(21) Appl. No.: 16/085,543

(22) PCT Filed: Mar. 16, 2017

(86) PCT No.: PCT/EP2017/056246
§ 371 (c)(1),
(2) Date: Sep. 14, 2018

(87) PCT Pub. No.: WO2017/158097
PCT Pub. Date: Sep. 21, 2017

(65) Prior Publication Data
US 2020/0299375 A1    Sep. 24, 2020

(30) Foreign Application Priority Data
Mar. 17, 2016  (EP) .................................... 16160918

(51) Int. Cl.
*C07K 16/24* (2006.01)
(52) U.S. Cl.
CPC ........ *C07K 16/241* (2013.01); *C07K 2317/24* (2013.01); *C07K 2317/33* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

2009/0202558 A1   8/2009  Couto

FOREIGN PATENT DOCUMENTS

| EP | 2 623 515 | 8/2013 |
|----|-----------|--------|
| WO | WO 2012/007880 | 1/2012 |
| WO | WO 2015/065987 | 5/2015 |
| WO | WO 2015/144852 | 10/2015 |
| WO | WO 2017/158079 | 9/2017 |
| WO | WO 2017/158084 | 9/2017 |
| WO | WO 2017/158092 | 9/2017 |

OTHER PUBLICATIONS

Brown et al. "Tolerance to Single, but Not Multiple, Amino Acid Replacements in Antibody VH, CDR2", J Immunol 1996; 156:3285-3291; (Year: 1996).*
Fleury et al. "Structural Evidence for Recognition of a Single Epitope by Two Distinct Antibodies". Proteins: Structure, Function, and Genetics 40:572-578 (2000) (Year: 2000).*
Jones et al. "High-Level Expression of Recombinant IgG in the Human Cell Line PER.C6". Biotechnol. Prog. 2003, 19, 163-168. (Year: 2003).*
Marie Wiekowski et al., "Infliximab (Remicade)", *Handbook of Therapeutic Antibodies*, pp. 885-904, Stefan Dübel, ed., Wiley VCH Verlag GmbH & Co. KGaA, Weinheim, Germany, Jan. 2007.
Harmut Kupper et al., "Adalimumab (Humira)", *Handbook of Therapeutic Antibodies*, pp. 697-732, Stefan Dübel, ed., Wiley VCH Verlag GmbH & Co. KGaA, Weinheim, Germany, Jan. 2007.
Gil Melmed et al., "Certolizumab pegol", *Nature Reviews: Drug Discovery*, vol. 7. No. 8, pp. 641-642, Aug. 1, 2008.
Sohini Mazumdar et al., "Golimumab", *MABS: Landes Bioscience*, vol. 1, No. 5, pp. 422-431, Sep. 1, 2009.
"CDP 571: Anti-TNF monoclonal antibody, BAY 103356, Bay W 3356, Humicade", *Drugs in R&D*, vol. 4, No. 3, pp. 174-178, Jan. 1, 2003.
José W. Saldanha, "Molecular Engineering I: Humanization", *Handbook of Therapeutic Antibodies*, pp. 119-144, Stefan Dübel, ed., Wiley VCH Verlag GmbH & Co. KGaA, Weinheim, Germany, Jan. 2007.
Jonathan Gershoni et al., "Epitope mapping—The First Step in Developing Epitope-Based Vaccines", *Biodrugs*, vol. 21, No. 3, pp. 145-156, Jan. 1, 2007.
Stuart Rudikoff et al., "Single Amino Acid Substituion Altering Antigen-Binding Specificity", *PNAS USA*, vol. 79, No. 6, pp. 1979-1983, Mar. 1, 1982.
Daniel Tracey et al., "Tumor Necrosis Factor Antagonist Mechanisms of Action: A Comprehensive Review", *Pharmacology & Therapeutics*, vol. 117, No. 2, pp. 244-279. Oct. 26, 2007.

* cited by examiner

*Primary Examiner* — Joanne Hama
*Assistant Examiner* — Scott T. Humbarger
(74) *Attorney, Agent, or Firm* — Smith Patent, LLC; Chalin A. Smith

(57) ABSTRACT

The present invention relates to antibody molecules and functional fragments thereof, capable of binding to tumor necrosis factor alpha (TNFα), to processes for their production, and to their therapeutic uses.

20 Claims, 12 Drawing Sheets

Specification includes a Sequence Listing.

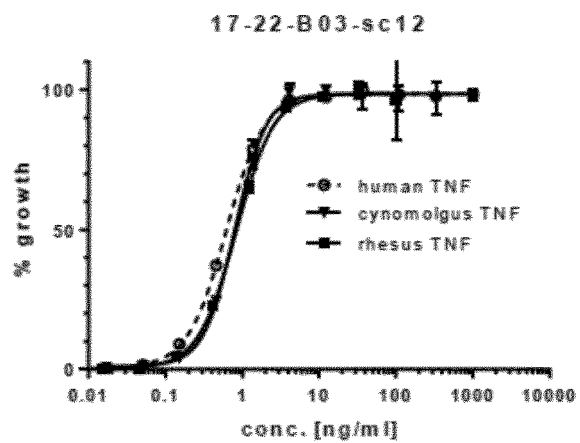
Figure 9
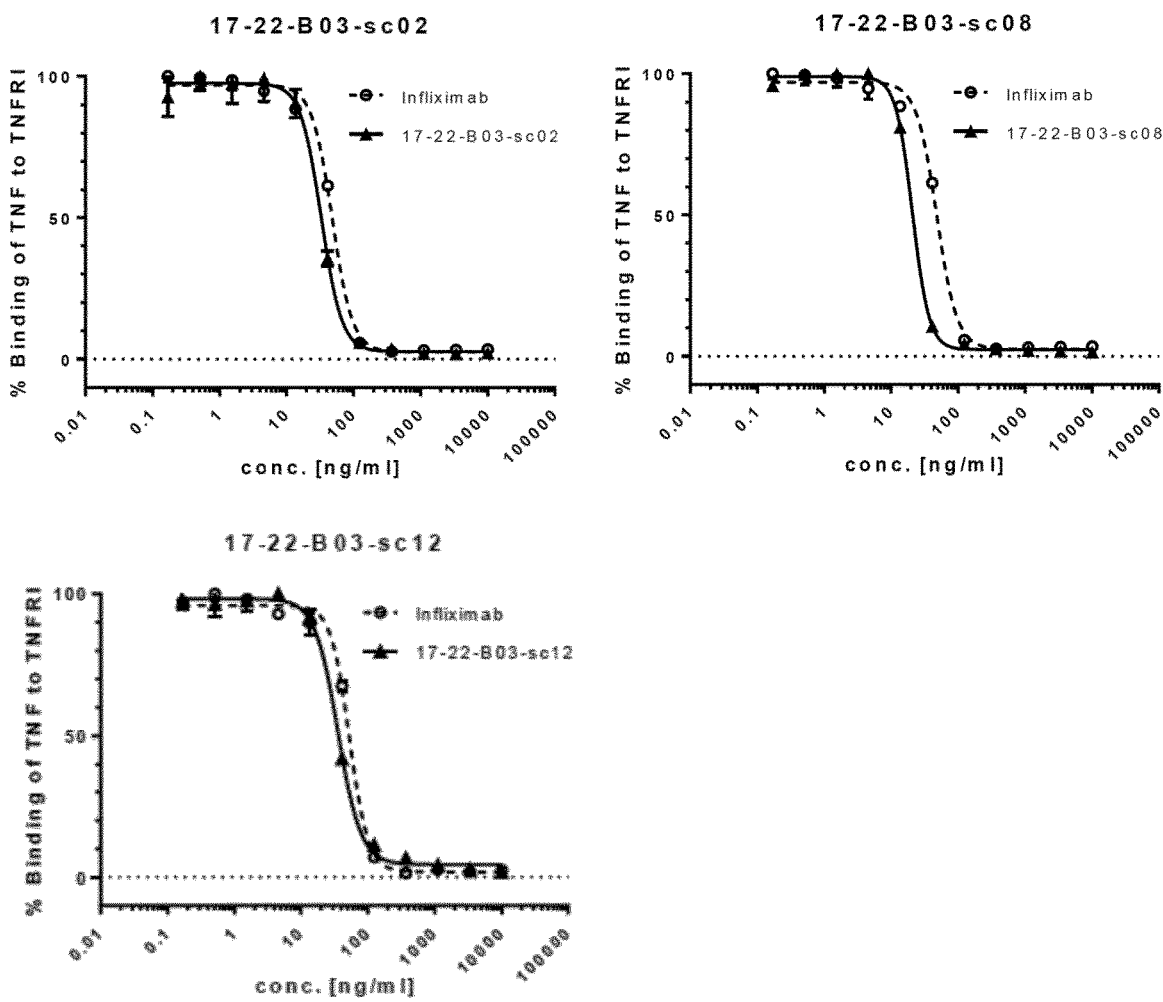

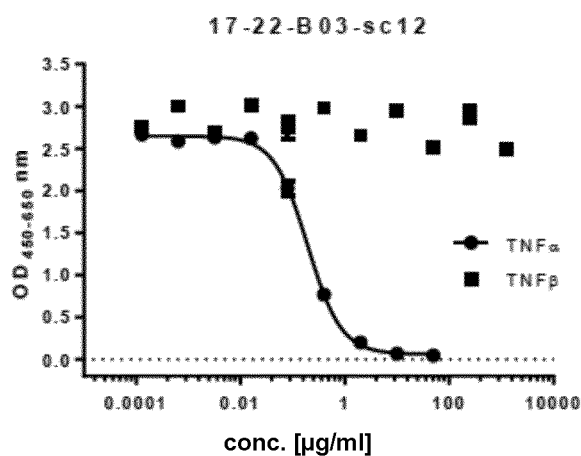
Figure 12
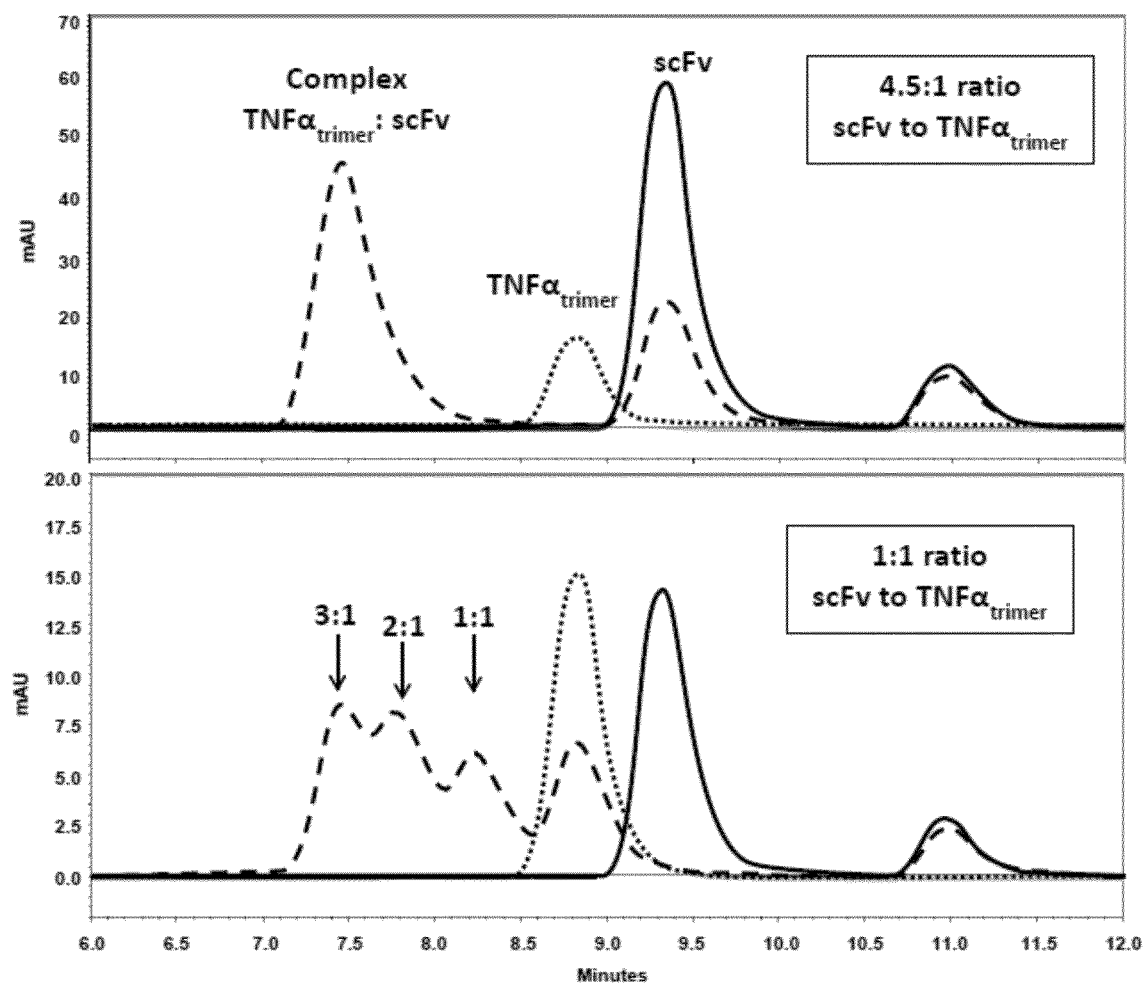

ANTI-TNF-α-ANTIBODIES AND FUNCTIONAL FRAGMENTS THEREOF

RELATED APPLICATIONS

The present application is related to the following co-pending applications:
U.S. application Ser. No. 16/085,506 filed on Sep. 14, 2018; and
U.S. application Ser. No. 16/085,565 filed on Sep. 15, 2018; and
U.S. application Ser. No. 16/085,570 filed on Sep. 15, 2018;
all of which share at least one common inventor as well as a common foreign priority date with the present invention (i.e., Mar. 17, 2016). As such, none should or are admitted to be prior art to the present invention.

PRIORITY

This application corresponds to the U.S. National Phase of International Application No. PCT/EP2017/056246, filed Mar. 16, 2017, which, in turn, claims priority to European Patent Application No. 16.160918.5 filed Mar. 17, 2016, the contents of which are incorporated by reference herein in their entirety.

SEQUENCE LISTING

The instant application contains a Sequence Listing that has been submitted in ASCII format via EFS-Web and is hereby incorporated by reference in its entirety. Said ASCII copy, created on Sep. 14, 2018, is named LNK_193US_SEQ_LIST.txt and is 20,272 bytes in size.

FIELD OF THE INVENTION

The present invention relates to antibody molecules and functional fragments thereof, capable of binding to tumor necrosis factor alpha (TNFα), to processes for their production, and to their therapeutic uses.

BACKGROUND

TNFα is a homo-trimeric pro-inflammatory cytokine that is released by and interacts with cells of the immune system. TNFα has also been shown to be up-regulated in a number of human diseases, including chronic diseases such as rheumatoid arthritis, Crohn's disease, ulcerative colitis and multiple sclerosis.

Antibodies to TNFα have been proposed for the prophylaxis and treatment of endotoxic shock (Beutler et al., Science, 234, 470-474, 1985). Bodmer et al., (Critical Care Medicine, 21, S441-S446, 1993) and Wherry et al., (Critical Care Medicine, 21, S436-S440, 1993) discuss the therapeutic potential of anti-TNFα antibodies in the treatment of septic shock. The use of anti-TNFα antibodies in the treatment of septic shock is also discussed by Kirschenbaum et al., (Critical Care Medicine, 26, 1625-1626, 1998). Collagen-induced arthritis can be treated effectively using an anti-TNFα monoclonal antibody (Williams et al. (PNAS-USA, 89, 9784-9788, 1992)).

The use of anti-TNFα antibodies in the treatment of rheumatoid arthritis and Crohn's disease is discussed in Feldman et al. (Transplantation Proceedings, 30, 4126-4127, 1998), Adorini et al. (Trends in Immunology Today, 18, 209-211, 1997) and in Feldman et al. (Advances in Immunology, 64, 283-350, 1997). The antibodies to TNFα previously used in such treatments are generally chimeric antibodies, such as those described in U.S. Pat. No. 5,919,452.

Monoclonal antibodies against TNFα have been described in the prior art. Meager et al. (Hybridoma, 6, 305-311, 1987) describe murine monoclonal antibodies against recombinant TNFα. Fendly et al. (Hybridoma, 6, 359-370, 1987) describe the use of murine monoclonal antibodies against recombinant TNFα in defining neutralising epitopes on TNF.

Furthermore, in International Patent Application WO 92/11383, recombinant antibodies, including CDR-grafted antibodies, specific for TNFα are disclosed. Rankin et al. (British J. Rheumatology, 34, 334-342, 1995) describe the use of such CDR-grafted antibodies in the treatment of rheumatoid arthritis. U.S. Pat. No. 5,919,452 discloses anti-TNFα chimeric antibodies and their use in treating pathologies associated with the presence of TNFα. Further anti-TNFα antibodies are disclosed in Stephens et al. (Immunology, 85, 668-674, 1995), GB-A-2 246 570, GB-A-2 297 145, U.S. Pat. No. 8,673,310, US 2014/0193400, EP 2 390 267 B1, U.S. Pat. Nos. 8,293,235, 8,697,074, WO 2009/155723 A2 and WO 2006/131013 A2.

The prior art recombinant anti-TNFα antibody molecules generally have a reduced affinity for TNFα compared to the antibodies from which the hypervariable regions or CDRs are derived. All currently marketed inhibitors of TNFα are administered intravenously or subcutaneously in weekly or longer intervals as bolus injections, resulting in high starting concentrations that are steadily decreasing until the next injection.

Currently approved anti-TNFα biotherapeutics include (i) infliximab, a chimeric IgG anti-human monoclonal antibody (Remicade®; Wiekowski M et al: "Infliximab (Remicade)", Handbook of Therapeutic Antibodies, WILEY-VCH; Weinheim, 2007 Jan. 1, p. 885-904); (ii) etanercept, a TNFR2 dimeric fusion protein, with an IgG1 Fc (Enbrel®); (iii) adalimumab, a fully human monoclonal antibody (mAb) (Humira®; Kupper H et al: "Adalimumab (Humira)", Handbook of Therapeutic Antibodies, WILEY-VCH; Weinheim, 2007 Jan. 1, p. 697-732), (iv) certolizumab, a PEGylated Fab fragment (Cimzia®; Melmed G Y et al: "Certolizumab pegol", Nature Reviews. Drug Discovery, Nature Publishing Group, GB, Vol. 7, No. 8, 2008-08-01, p. 641-642); (v) Golimumab, a human IgGIK monoclonal antibody (Simponi®; Mazumdar S et al: "Golimumab", mAbs, Landes Bioscience, US, Vol. 1, No. 5, 2009 Sep. 1, p. 422-431). However, various biosimilars are in development, and a mimic of infliximab known as Remsima has already been approved in Europe.

Infliximab has a relatively low affinity to TNFα ($K_D$>0.2 nM; Weir et al., 2006, Therapy 3: 535) and a limited neutralization potency in an L929 assay. In addition, infliximab shows substantially no cross-reactivity with TNFα from Cynomolgus or Rhesus monkeys. For anti-TNFα antibodies, however, cross-reactivity with TNFα from monkeys is highly desirable, as this allows for animal tests with primates, reflecting the situation in humans in many aspects.

Etanercept, although a bivalent molecule, binds TNFα at a ratio of one trimer per one etanercept molecule, precluding the formation of large antigen-biotherapeutics complexes (Wallis, 2008, Lancet Infect Dis 8: 601). It does not inhibit LPS-induced cytokine secretion in monocytes (Kirchner et al., 2004, Cytokine 28: 67).

The potency of adalimumab is similar to that of infliximab. Another disadvantage of adalimumab is its poor stability, e.g. as determined in a thermal unfolding test. The melting temperature ($T_m$) of adalimumab in such a test was determined to be 67.5° C. The lower the $T_m$ value of an antibody, however, the lower is its general stability. A lower $T_m$ makes antibodies less suitable for pharmaceutical use, e.g. for oral administration.

The potency of certolizumab is slightly greater than that of infliximab, but still not satisfying. Certolizumab does not inhibit T-cell proliferation in a MLR (Vos et al., 2011, Gastroenterology 140: 221).

EP2623515 A1 discloses humanized anti-TNFα antibodies and antigen-binding fragments (Fab) thereof. As becomes clear from the disclosed examples, the potency of the resulting humanized Fab fragments is comparable to that of infliximab in a L929 neutralization assay (see Table 2 and 5). The sole anti-TNFα IgG antibody tested for cross-reactivity binds only weakly to Rhesus TNF-α (see [0069]; FIG. 3). Cross-reactivity with Cynomolgus TNFα was not tested. Moreover, there is weak binding to human TNFβ (see FIG. 3). Therefore, EP2623515 A1 does not disclose anti-TNFα antibodies or functional fragments thereof, which have a potency to inhibit TNFα-induced apoptosis in L929 cells greater than that of infliximab and which are cross-reactive with Rhesus TNFα and Cynomolgus TNFα.

WO 2012/007880 A2 discloses a modified single domain antigen binding molecule (SDAB) in the form of fusion proteins comprising one or more single antigen binding domains that bind to one or more targets (e.g. TNFα), a linker and one or more polymer molecules. The only specific example given is termed SDAB-01 and includes two antigen binding domains, which bind to TNFα, connected with a flexible linker, and a C-terminal Cysteine supporting the site specific PEGylation (see FIG. 3). WO 2012/007880 A2 fails to compare the potency of SDAB-01 to known TNFα antibodies like infliximab in a L929 cell-based neutralization assay, or to assess other SDAB-01-specific parameters like the effectiveness to block TNFα-TNFRI/II interaction and the selectivity for binding TNFα over TNFβ. In an assay where the treatment with SDAB-01 and infliximab are compared in a transgenic mouse model for polyarthritis that overexpresses human TNFα (see page 54, Example 8), the two seem to be similarly effective in preventing further development of arthritis (e.g. FIGS. 17&18). However, the dosage given in this example is misleading as the molecular weight of SDAB-01 is less than half of that of infliximab. Thus, WO 2012/007880 A2 does not disclose anti-TNFα antibodies having a potency to inhibit TNFα-induced apoptosis in L929 cells greater than that of infliximab.

WO 2015/144852 A1 investigates the properties of an anti-TNF-α scFv designated "scFv1". This scFv showed a TNFα neutralization capacity in a PK-15 cell assay that was comparable to that of infliximab (see [0236]). In addition, the scFv seems to have some cross-reactivity to TNF-α from rhesus macaque and cynomolgus monkey (see Ex. 8). No affinity data are reported in WO 2015/144852 A1. The single chain antibody fragment DLX105 (also known as ESBA 105), however, which is known to have only moderate affinity ($K_D$=157 pM; see Urech et al. 2010 Ann Rheum Dis 69: 443) shows a better binding to TNFα than scFv1 (see FIG. 1 of WO 2015/144852 A1). Therefore, WO 2015/144852 A1 does not disclose anti-TNF-α antibodies having high affinity for human TNFα ($K_D$<100 pM).

WO 2015/065987 A1 describes anti-TNF-α antibodies, anti-IL-6 antibodies, and bispecific antibodies binding to both antigens. Certain anti-TNFα antibodies showed some cross-reactivity with TNFα from Cynomolgus (FIG. 17). The anti-TNFα antibodies, however, exhibited a significantly lower potency than infliximab in an L929 neutralization assay ([0152]; FIG. 5). Therefore, WO 2015/065987 A1 does not disclose anti-TNF-α antibodies having a potency to inhibit TNFα-induced apoptosis in L929 cells greater than that of infliximab.

Drugs in R&D, Vol. 4 No. 3, 2003, pages 174-178 describes the humanized antibody "Humicade" (CDP 571; BAY 103356), a monoclonal anti-TNFα antibody with high affinity. The potency of Humicade to inhibit TNFα-induced apoptosis in L929 cells, however, appears to be limited (see, e.g., US 2003/0199679 A1 at [0189]). The reference therefore does not disclose anti-TNF-α antibodies having a potency to inhibit TNFα-induced apoptosis in L929 cells greater than that of infliximab.

Saldanha J W et al: "Molecular Engineering I: Humanization", Handbook of Therapeutic Antibodies, Chapter 6, 2007 Jan. 1, WILEY-VCH, Weinheim, p. 119-144 discloses different strategies for humanization of monoclonal antibodies including CDR Grafting, Resurfacing/Veneering, SDR transfer and DeImmunization Technology.

There is a need for improved antibody molecules to treat chronic inflammatory diseases such as inflammatory bowel disorders. The antibody molecules should at least have (i) high affinity for human TNFα (i.e. a $K_D$<100 pM), (ii) a high potency to inhibit TNFα-induced apoptosis in L929 cells, (iii) substantial affinity to TNFα from Cynomolgus and Rhesus (e.g. a $K_D$<1 nM), and (iv) a high melting temperature of the variable domain as determined in a thermal unfolding experiment (e.g. a $T_m$>70° C.).

SUMMARY OF THE INVENTION

The inventors of the present application found that certain anti-TNFα antibodies and functional fragments thereof exhibit a combination of favorable properties, including high affinity for human TNFα ($K_D$<100 pM), a potency to inhibit TNFα-induced apoptosis in L929 cells greater than that of infliximab, and substantial affinity ($K_D$<1 nM) to TNFα from animals such as Cynomolgus monkey (*Macaca fascicularis*) and/or Rhesus macaques (*Macaca mulatta*). In addition, the antibodies and functional fragments thereof were specific for TNFα in that they did not significantly bind to TNFβ, and exhibit a significant stability, as determined in a thermal unfolding assay of the variable domain.

The invention provides antibody molecules and functional fragments thereof.

The present invention therefore relates to the subject matter defined in the following items (1) to (47):

(1) An antibody or a functional fragment thereof capable of binding to human tumor necrosis factor alpha (TNFα), wherein said antibody or functional fragment thereof comprises (i) a $V_L$ domain comprising a CDR1 region having an amino acid sequence in accordance with the amino acid sequence as shown in SEQ ID NO:1, a CDR2 region having an amino acid sequence in accordance with the amino acid sequence as shown in SEQ ID NO:2, and a CDR3 region having an amino acid sequence in accordance with the amino acid sequence as shown in SEQ ID NO:3, and (ii) a $V_H$ domain comprising a CDR1 region having an amino acid sequence in accordance with the amino acid sequence as shown in SEQ ID NO:4, a CDR2 region having an amino acid sequence in accordance with the amino acid sequence as shown in SEQ ID NO:5, and a CDR3 region having the amino acid sequence as shown in SEQ ID NO:6.

(2) The antibody or functional fragment of item (1), wherein said antibody or functional fragment comprises (i) a $V_L$ domain comprising a CDR1 region having the amino acid sequence as shown in SEQ ID NO:7, a CDR2 region having the amino acid sequence as shown in SEQ ID NO:8, and a CDR3 region having the amino acid sequence as shown in SEQ ID NO:9, and (ii) a $V_H$ domain comprising a CDR1 region having the amino acid sequence as shown in SEQ ID NO:10, a CDR2 region having the amino acid sequence as shown in SEQ ID NO:11, and a CDR3 region having the amino acid sequence as shown in SEQ ID NO:6.

(3) The antibody or functional fragment of any one of the preceding items, wherein said antibody or functional fragment comprises a $V_H$ domain having the amino acid sequence as shown in SEQ ID NO:21.

(4) The antibody or functional fragment of any one of the preceding items, wherein said antibody or functional fragment comprises a $V_L$ domain having an amino acid sequence selected from the group consisting of SEQ ID NO:22, SEQ ID NO:23 and SEQ ID NO:24; preferably selected from the group consisting of SEQ ID NO:22 and SEQ ID NO:23.

(5) The antibody or functional fragment of any one of the preceding items, wherein said antibody or functional fragment thereof specifically binds to human TNFα.

(6) The antibody or functional fragment of any one of any one of the preceding items, wherein said antibody or functional fragment thereof does not significantly bind to TNFβ.

(7) The antibody or functional fragment of any one of the preceding items, wherein said antibody or functional fragment
   (i) binds to human TNFα with a dissociation constant ($K_D$) of less than 100 pM;
   (ii) is cross-reactive with *Macaca mulatta* TNFα and with *Macaca fascicularis* TNFα;
   (iii) has a greater potency than infliximab, as determined by an L929 assay; and/or
   (iv) is capable of binding to human TNFα$_{Trimer}$ in a stoichiometry (antibody: TNFα$_{Trimer}$) of at least 2.

(8) The antibody or functional fragment of any one of the preceding items, which binds to human TNFα with a $K_D$ of less than 75 pM.

(9) The antibody or functional fragment of any one of the preceding items, which binds to TNFα from *Macaca mulatta* with a $K_D$ of less than 1 nM.

(10) The antibody or functional fragment of any one of the preceding items, which binds to TNFα from *Macaca fascicularis* with a $K_D$ of less than 1 nM.

(11) The antibody or functional fragment of any one of the preceding items, wherein the potency of the antibody or functional fragment to inhibit TNFα-induced apoptosis relative to that of infliximab (relative potency), determined in an L929 assay, is greater than 5, and wherein said relative potency is the ratio of the IC$_{50}$ value in ng/mL of infliximab in the L929 assay to the IC$_{50}$ value in ng/mL of the antibody in scFv format in the L929 assay.

(12) The antibody or functional fragment of any one of the preceding items, wherein the melting temperature of the variable domain of the antibody in scFv format, determined by differential scanning fluorimetry, is at least 65° C.

(13) The antibody or functional fragment of any one of the preceding items, wherein the melting temperature of the variable domain of the antibody in scFv format, determined by differential scanning fluorimetry, is at least 70° C.

(14) The antibody or functional fragment of any one of the preceding items, wherein the melting temperature, determined by differential scanning fluorimetry, is at least 75° C.

(15) The antibody or functional fragment of any one of the preceding items, wherein the loss in monomer content, after five consecutive freeze-thaw cycles, is less than 0.2%.

(16) The antibody or functional fragment of any one of the preceding items, wherein the loss in monomer content, after storage for four weeks at 4° C., is less than 1%.

(17) The antibody or functional fragment of any one of the preceding items, wherein the potency of the antibody or functional fragment to block the interaction between human TNFα and TNF receptor I (TNFRI), relative to that of infliximab (relative potency), as determined in an inhibition ELISA, is at least 1.3, wherein said relative potency is the ratio of the IC$_{50}$ value in ng/mL of infliximab to the IC$_{50}$ value in ng/mL of the antibody in scFv format.

(18) The antibody or functional fragment of any one of the preceding items, wherein the potency of the antibody or functional fragment to block the interaction between human TNFα and TNF receptor II (TNFRII), relative to that of infliximab (relative potency), as determined in an inhibition ELISA, is at least 1.3, wherein said relative potency is the ratio of the IC$_{50}$ value in ng/mL of infliximab to the IC$_{50}$ value in ng/mL of the antibody in scFv format.

(19) The antibody or functional fragment of any one of the preceding items, which is capable of inhibiting cell proliferation of peripheral blood mononuclear cells in a mixed lymphocyte reaction.

(20) The antibody or functional fragment of any one of the preceding items, which is capable of inhibiting LPS-induced secretion of interleukin-1β from CD14$^+$ monocytes.

(21) The antibody or functional fragment of item (20), wherein the IC$_{50}$ value for inhibiting LPS-induced secretion of interleukin-1β is less than 1 nM.

(22) The antibody or functional fragment of item (21), wherein said IC$_{50}$ value for inhibiting LPS-induced secretion of interleukin-1β, on a molar basis, is lower than that of adilumumab.

(23) The antibody or functional fragment of any one of the preceding items, which is capable of inhibiting LPS-induced secretion of TNFα from CD14$^+$ monocytes.

(24) The antibody or functional fragment of item (23), wherein the IC$_{50}$ value for inhibiting LPS-induced secretion of TNFα is less than 1 nM.

(25) The antibody or functional fragment of item (24), wherein said IC$_{50}$ value for inhibiting LPS-induced secretion of TNFα, on a molar basis, is lower than that of adalimumab.

(26) The antibody of any one of the preceding items, which is an immunoglobulin G (IgG).

(27) The functional fragment of any one of items (1) to (25), which is a single-chain variable fragment (scFv).

(28) The functional fragment of item (27), wherein said scFv comprises or consists of an amino acid sequence selected from the group consisting of SEQ ID NO:25, SEQ ID NO:26 and SEQ ID NO:27, preferably selected from the group consisting of SEQ ID NO:25 and SEQ ID NO:26.

(29) The functional fragment of any one of items (1) to (25), which is a diabody.

(30) An antibody or functional fragment thereof binding to essentially the same epitope on human TNFα as an antibody comprising a $V_H$ domain having the amino acid sequence as shown in SEQ ID NO:21 and a $V_L$ domain having the amino acid sequence selected from the group consisting of SEQ ID NO:22, SEQ ID NO:23 and SEQ ID NO:24, preferably the functional fragment comprising the $V_L$ domain consisting of an amino acid sequence selected from the group consisting of SEQ ID NO:22 and SEQ ID NO:23, in particular wherein said antibody or functional fragment exhibits one or more of the features referred to in items 1 to 29 herein above.

(31) The antibody or functional fragment of any one of the preceding items, wherein the sum of (i) the number of amino acids in framework regions I to III of the variable light domain of said antibody or functional fragment that are different from the respective human Vκ1 consensus sequences with SEQ ID NOs: 31 to 33 (see Table 10), and (ii) the number of amino acids in framework region IV of the variable light domain of said antibody or functional fragment that are different from the most similar human λ germline-based sequence selected from SEQ ID NOs: 34 to 37 (see Table 11), is less than 7, preferably less than 4.

(32) The antibody or functional fragment of any one of the preceding items, wherein the framework regions I to III of the variable light domain of said antibody or functional fragment consist of human Vκ1 consensus sequences with SEQ ID NOs:31 to 33, respectively, and framework region IV consists of a λ germline-based sequence selected from SEQ ID NOs:34 to 37.

(33) A nucleic acid encoding the antibody or functional fragment of any one of the preceding items.

(34) A vector or plasmid comprising the nucleic acid of item (33).

(35) A cell comprising the nucleic acid of item (34) or the vector or plasmid of item (33).

(36) A method of preparing the antibody or functional fragment of any one of items (1) to (32), comprising culturing the cell of item (35) in a medium under conditions that allow expression of the nucleic acid encoding the antibody or functional fragment, and recovering the antibody or functional fragment from the cells or from the medium.

(37) A pharmaceutical composition comprising the antibody or functional fragment of any one of items (1) to (32), and optionally a pharmaceutically acceptable carrier and/or excipient.

(38) The antibody or functional fragment as defined in any one of items (1) to (32) for use in a method of treating an inflammatory disorder or a TNFα-related disorder.

(39) The antibody or functional fragment for use according to item (38), wherein said inflammatory disorder or TNFα-related disorder is selected from the list of disorders and diseases listed in Section "Disorders to be treated" below.

(40) The antibody or functional fragment for use according to item (38), wherein said inflammatory disorder is an inflammatory disorder of the gastrointestinal tract.

(41) The antibody or functional fragment for use according to item (40), wherein said inflammatory disorder of the gastrointestinal tract is inflammatory bowel disease.

(42) The antibody or functional fragment for use according to item (40) or (41), wherein said inflammatory disorder of the gastrointestinal tract is Crohn's disease.

(43) The antibody or functional fragment for use according to item (42), wherein said Crohn's disease is selected from the group consisting of ileal, colonic, ileocolonic, and/or isolated upper Crohn's disease (gastric, duodenal and/or jejunal) and including non-stricturing/non-penetrating, stricturing, penetrating and perianal disease behavior, allowing any combination of localization and disease behavior of any of the above mentioned.

(44) The antibody or functional fragment for use according to item (40) or (41), wherein said inflammatory disorder of the gastrointestinal tract is ulcerative colitis.

(45) The antibody or functional fragment for use according to item (44), wherein said ulcerative colitis is selected from the group consisting of ulcerative proctitis, proctosigmoiditis, left-sided colitis, pan-ulcerative colitis, and pouchitis.

(46) The antibody or functional fragment for use according to item (40) or (41), wherein said inflammatory disorder of the gastrointestinal tract is microscopic colitis.

(47) The antibody or functional fragment for use according to any one of items (38) to (46), wherein said method comprises orally administering the antibody or functional fragment to a subject.

BRIEF DESCRIPTION OF THE DRAWINGS

FIG. 9: Potency of two scFvs to block the TNFα-TNFRI interaction. Dose-response curves are shown. The highest scFv concentration and negative controls were set to 0% and 100% of binding of TNFα to TNFRI.

FIG. 12 depicts the formation of 17-22-B03-scFv:TNFα complexes determined by SE-HPLC (Example 4).

DETAILED DESCRIPTION

Figure 1:
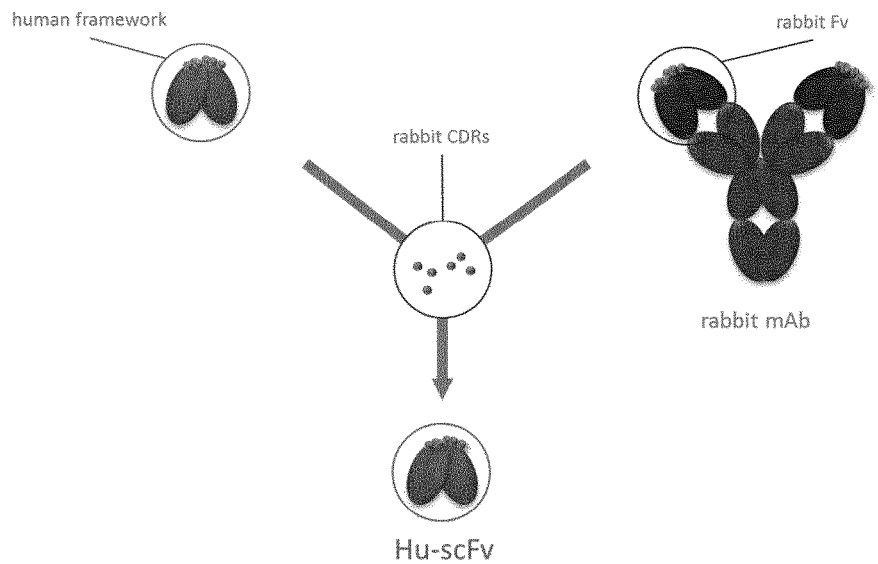
FIG. 1: Schematic representation of the humanization process.

The present invention pertains to an antibody or a functional fragment thereof capable of binding to human TNFα.

In the context of the present application, the term "antibody" is used as a synonym for "immunoglobulin" (Ig), which is defined as a protein belonging to the class IgG, IgM, IgE, IgA, or IgD (or any subclass thereof), and includes all conventionally known antibodies and functional fragments thereof. In the context of the present invention, a "functional fragment" of an antibody/immunoglobulin is defined as antigen-binding fragment or other derivative of a parental antibody that essentially maintains one or more of the properties of such parental antibody referred to in items (1) to (30) herein above. An "antigen-binding fragment" of an antibody/immunoglobulin is defined as fragment (e.g., a variable region of an IgG) that retains the antigen-binding region. An "antigen-binding region" of an antibody typically is found in one or more hypervariable region(s) of an antibody, i.e., the CDR-1, -2, and/or -3 regions. "Antigen-binding fragments" of the invention include the domain of a F(ab')$_2$ fragment and a Fab fragment. "Functional fragments" of the invention include, scFv, dsFv, diabodies, triabodies, tetrabodies and Fc fusion proteins. The F(ab')$_2$ or Fab may be engineered to minimize or completely remove the intermolecular disulphide interactions that occur between the CH1 and CL domains. The antibodies or functional fragments of the present invention may be part of bi- or multifunctional constructs.

Preferred functional fragments in the present invention are scFv and diabodies.

An scFv is a single chain Fv fragment in which the variable light ("$V_L$") and variable heavy ("$V_H$") domains are linked by a peptide bridge.

A diabody is a dimer consisting of two fragments, each having variable regions joined together via a linker or the like (hereinafter referred to as diabody-forming fragments), and typically contain two $V_L$s and two $V_H$s. Diabody-forming fragments include those consisting of $V_L$ and $V_H$, $V_L$ and $V_L$, $V_H$ and $V_H$, etc., preferably $V_H$ and $V_L$. In diabody-forming fragments, the linker joining variable regions is not specifically limited, but preferably enough short to avoid noncovalent bonds between variable regions in the same fragment. The length of such a linker can be determined as appropriate by those skilled in the art, but typically 2-14 amino acids, preferably 3-9 amino acids, especially 4-6 amino acids. In this case, the $V_L$ and $V_H$ encoded on the same fragment are joined via a linker short enough to avoid noncovalent bonds between the $V_L$ and $V_H$ on the same chain and to avoid the formation of single-chain variable region fragments so that dimers with another fragment can be formed. The dimers can be formed via either covalent or noncovalent bonds or both between diabody-forming fragments.

Moreover, diabody-forming fragments can be joined via a linker or the like to form single-chain diabodies (sc(Fv)$_2$). By joining diabody-forming fragments using a long linker of about 15-20 amino acids, noncovalent bonds can be formed between diabody-forming fragments existing on the same chain to form dimers. Based on the same principle as for preparing diabodies, polymerized antibodies such as trimers or tetramers can also be prepared by joining three or more diabody-forming fragments.

Preferably, the antibody or functional fragment of the invention specifically binds to TNFα. As used herein, an antibody or functional fragment thereof "specifically recognizes", or "specifically binds to" human TNFα, when the antibody or functional fragment is able to discriminate between human TNFα and one or more reference molecule(s). Preferably, the IC$_{50}$ value for binding to each of the reference molecules is at least 1,000 times greater than the IC$_{50}$ value for binding to TNFα, particularly as described in Example 2, section 2.1.4. In its most general form (and when no defined reference is mentioned), "specific binding" is referring to the ability of the antibody or functional fragment to discriminate between human TNFα and an unrelated biomolecule, as determined, for example, in accordance with a specificity assay methods known in the art. Such methods comprise, but are not limited to, Western blots and ELISA tests. For example, a standard ELISA assay can be carried out. Typically, determination of binding specificity is performed by using not a single reference biomolecule, but a set of about three to five unrelated biomolecules, such as milk powder, BSA, transferrin or the like. In one embodiment, specific binding refers to the ability of the antibody or fragment to discriminate between human TNFα and human TNFβ.

The antibody of the invention or the functional fragment of the invention comprises a $V_L$ domain and a $V_H$ domain. The $V_L$ domain comprises a CDR1 region (CDRL1), a CDR2 region (CDRL2), a CDR3 region (CDRL3) and Framework regions. The $V_H$ domain comprises a CDR1 region (CDRH1), a CDR2 region (CDRH2), a CDR3 region (CDRH3) and Framework regions.

The term "CDR" refers to one of the six hypervariable regions within the variable domains of an antibody that mainly contribute to antigen binding. One of the most commonly used definitions for the six CDRs was provided by Kabat E. A. et al., (1991) Sequences of proteins of immunological interest. NIH Publication 91-3242). As used herein, Kabat's definition of CDRs only apply for CDR1, CDR2 and CDR3 of the light chain variable domain (CDR L1, CDR L2, CDR L3, or L1, L2, L3), as well as for CDR2 and CDR3 of the heavy chain variable domain (CDR H2, CDR H3, or H2, H3). CDR1 of the heavy chain variable domain (CDR H1 or H1), however, as used herein is defined by the following residues (Kabat numbering): It starts with position 26 and ends prior to position 36.

The CDR1 region of the $V_L$ domain consists of an amino acid sequence in accordance with the amino acid sequence as shown in SEQ ID NO:1. Preferably, the CDR1 region of the $V_L$ domain consists of an amino acid sequence selected from the group consisting of SEQ ID NO:7, SEQ ID NO:16, SEQ ID NO:17 and SEQ ID NO:19. Most preferably, the CDR1 region of the $V_L$ domain consists of the amino acid sequence as shown in SEQ ID NO:7.

The CDR2 region of the $V_L$ domain consists of an amino acid sequence in accordance with the amino acid sequence as shown in SEQ ID NO:2. Preferably, the CDR2 region of the $V_L$ domain consists of an amino acid sequence selected from the group consisting of SEQ ID NO:8, SEQ ID NO:13 and SEQ ID NO:20. Most preferably, the CDR2 region of the $V_L$ domain consists of the amino acid sequence as shown in SEQ ID NO:8.

The CDR3 region of the $V_L$ domain consists of an amino acid sequence in accordance with the amino acid sequence as shown in SEQ ID NO:3. Preferably, the CDR3 region of the $V_L$ domain consists of an amino acid sequence in accordance with the amino acid sequence as shown in SEQ ID NO:28. In a particular embodiment the CDR3 region of the $V_L$ domain consists of the amino acid sequence as shown in SEQ ID NO:9.

The CDR1 region of the $V_H$ domain consists of an amino acid sequence in accordance with the amino acid sequence as shown in SEQ ID NO:4. Preferably, the CDR1 region of the $V_H$ domain consists of an amino acid sequence selected from the group consisting of SEQ ID NO:10 and SEQ ID NO:18. Most preferably, the CDR1 region of the $V_H$ domain consists of the amino acid sequence as shown in SEQ ID NO:10.

The CDR2 region of the $V_H$ domain consists of an amino acid sequence in accordance with the amino acid sequence as shown in SEQ ID NO:5. Preferably, the CDR2 region of the $V_H$ domain consists of an amino acid sequence selected from the group consisting of SEQ ID NO:11, SEQ ID NO:12, SEQ ID NO:14 and SEQ ID NO:15. Most preferably, the CDR2 region of the $V_H$ domain consists of the amino acid sequence as shown in SEQ ID NO:11.

The CDR3 region of the $V_H$ domain consists of an amino acid sequence in accordance with the amino acid sequence as shown in SEQ ID NO:6.

In a particular embodiment, the antibody of the invention or the functional fragment of the invention comprises (i) a $V_L$ domain comprising a CDR1 region having an amino acid sequence in accordance with the amino acid sequence as shown in SEQ ID NO:1, a CDR2 region having an amino acid sequence in accordance with the amino acid sequence as shown in SEQ ID NO:2, and a CDR3 region having an amino acid sequence in accordance with the amino acid sequence as shown in SEQ ID NO:3, and (ii) a $V_H$ domain comprising a CDR1 region having an amino acid sequence in accordance with the amino acid sequence as shown in SEQ ID NO:4, a CDR2 region having an amino acid sequence in accordance with the amino acid sequence as shown in SEQ ID NO:5, and a CDR3 region having an amino acid sequence in accordance with the amino acid sequence as shown in SEQ ID NO:6

In a particular embodiment, the antibody of the invention or the functional fragment of the invention comprises (i) a $V_L$ domain comprising a CDR1 region having the amino acid sequence as shown in SEQ ID NO:7, a CDR2 region having the amino acid sequence as shown in SEQ ID NO:8, and a CDR3 region having the amino acid sequence as shown in SEQ ID NO:9, and (ii) a $V_H$ domain comprising a CDR1 region having the amino acid sequence as shown in SEQ ID NO:10, a CDR2 region having the amino acid sequence as shown in SEQ ID NO:11, and a CDR3 region having the amino acid sequence as shown in SEQ ID NO:6.

In a more preferred embodiment, the antibody of the invention or the functional fragment of the invention comprises a $V_H$ domain having the amino acid sequence as shown in SEQ ID NO:21. In another more preferred embodiment the antibody or functional fragment comprises a $V_L$ domain having the amino acid sequence selected from the group consisting of SEQ ID NO:22, SEQ ID NO:23 and SEQ ID NO:24. In an even more preferred embodiment the antibody or functional fragment comprises a $V_L$ domain having the amino acid sequence selected from the group consisting of SEQ ID NO:22 and SEQ ID NO:23. Most preferably, the antibody of the invention or the functional fragment of the invention comprises (i) a $V_H$ domain having the amino acid sequence as shown in SEQ ID NO:21, and (ii) a $V_L$ domain having the amino acid sequence as shown in SEQ ID NO:22, SEQ ID NO:23 or SEQ ID NO:24

In a particularly preferred embodiment, the functional fragment is a single chain antibody (scFv) comprising a $V_H$ domain having the amino acid sequence as shown in SEQ ID NO:21 and a $V_L$ domain having the amino acid sequence selected from the group consisting of SEQ ID NO:22, SEQ ID NO:23 and SEQ ID NO:24. The $V_H$ domain and the $V_L$ domain are preferably linked by a peptide linker. The peptide linker (hereinafter referred to as "linkerA") typically has a length of about 10 to about 30 amino acids, more preferably of about 15 to about 25 amino acids. The linkerA typically comprises Gly and Ser residues, but other amino acids are also possible. In preferred embodiments the linker comprises multiple repeats of the sequence GGGGS (SEQ ID NO:30), e.g. 2 to 6, or 3 to 5, or 4 consecutive repeats of the amino acid sequence as shown in SEQ ID NO:30. Most preferably, the linkerA consists of the amino acid sequence as shown in SEQ ID NO:29. The scFv may have the following structure (with the N-terminus being left and the C-terminus being right):

$V_L$-LinkerA-$V_H$; or
$V_H$-LinkerA-$V_L$.

Most preferably, the functional fragment is a single chain antibody (scFv) consisting of the amino acid sequence selected from the group consisting of SEQ ID NO:25, SEQ ID NO:26 and SEQ ID NO:27.

In another particularly preferred embodiment, the functional fragment is a diabody comprising a $V_H$ domain having the amino acid sequence as shown in SEQ ID NO:21 and a $V_L$ domain having the amino acid sequence selected from the group consisting of SEQ ID NO:22, SEQ ID NO:23 and SEQ ID NO:24. The $V_H$ domain and the $V_L$ domain are linked by a peptide linker. The peptide linker (hereinafter referred to as "linkerB") preferably has a length of about 2 to about 10 amino acids, more preferably of about 5 amino acids. The linkerB typically comprises Gly and Ser residues, but other amino acids are also possible. Most preferably, the linkerB consists of the amino acid sequence as shown in SEQ ID NO:30.

The diabody preferably is a monospecific diabody, i.e. it is directed to one epitope only. The diabody is preferably a homodimer. The diabody may be a dimer of two polypeptide chains that are non-covalently bound to each other. Each monomer may be a polypeptide chain having the structure:

$V_L$-LinkerB-$V_H$; or
$V_H$-LinkerB-$V_L$.

Moreover, diabody-forming fragments can be joined via a linkerA or the like to form single-chain diabodies (sc(Fv)$_2$). By joining diabody-forming fragments using a long linker of about 15-20 amino acids, noncovalent bonds can be formed between diabody-forming fragments existing on the same chain to form dimers. Examples of the arrangements of single-chain diabodies include the following.

$V_H$-linkerB-$V_L$-linkerA-$V_H$-linkerB-$V_L$
$V_L$-linkerB-$V_H$-linkerA-$V_L$-linkerB-$V_H$ Preferably the diabody of the invention has the following structure:

$V_L$-linkerB-$V_H$-linkerA-$V_L$-linkerB-$V_H$

Based on the same principle as for preparing diabodies, polymerized antibodies such as trimers or tetramers can also be prepared by joining three or more diabody-forming fragments.

In another particular embodiment the antibody of the invention is an immunoglobulin, preferably an immunoglobulin G (IgG). The subclass of the IgG of the invention is not limited and includes $IgG_1$, $IgG_2$, $IgG_3$, and $IgG_4$. Preferably, the IgG of the invention is of subclass 1, i.e. it is an $IgG_1$ molecule.

Affinity

The antibody or functional fragment of the invention has a high affinity to human TNFα. The term "$K_D$," refers to the dissociation equilibrium constant of a particular antibody-antigen interaction. Typically, the antibody or functional fragment of the invention binds to human TNFα with a dissociation equilibrium constant ($K_D$) of less than approximately $2 \times 10^{-10}$ M, preferably less than $1.5 \times 10^{-10}$ M, preferably less than $1 \times 10^{-10}$ M, most preferably less than $7 \times 10^{-11}$ M, or even lower, for example, as determined using surface plasmon resonance (SPR) technology in a BIA-CORE instrument. In particular, the determination of the $K_D$ is carried out as described in Example 2, section 2.1.1.

Cross-Reactivity to TNFα from Cynomolgus Monkeys or from Rhesus Macaques

In particular embodiments, the antibody or functional fragment of the invention has substantial affinity to TNFα from animals such as Cynomolgus monkeys (*Macaca fascicularis*) and/or Rhesus macaques (*Macaca mulatta*). This is advantageous, as preclinical tests of anti-human TNFα antibodies such as toxicity studies are preferably performed with such animals. Accordingly, the antibody or functional fragment of the invention is preferably cross-reactive with TNFα from animals such as Cynomolgus monkeys and/or Rhesus macaques. Affinity measurements are carried out as described in Example 2, section 2.1.1.

In one embodiment, the antibody or functional fragment of the invention is cross-reactive with TNFα from *Macaca fascicularis*. The antibody or functional fragment of the invention preferably has an affinity to *Macaca fascicularis* TNFα that is less than 10-fold, particularly less than 5-fold, even more particularly less than 2-fold, ore even less than 1.5-fold different to its affinity to human TNFα. Typically, the antibody or functional fragment of the invention binds to TNFα from *Macaca fascicularis* with a dissociation equilibrium constant ($K_D$), wherein the ratio $R_{M. fascicularis}$ of (i) the $K_D$ for binding to TNFα from *Macaca fascicularis* to (ii) the $K_D$ for binding to human TNFα is less than 10.

$$R_{M. fascicularis .} = \frac{K_D(M.\ fascicularis)}{K_D(\text{human})}$$

$R_{M. fascicularis}$ is preferably less than 5, particularly less than 2, even more particularly less than 1.5.

In another embodiment, the antibody or functional fragment of the invention is cross-reactive with TNFα from *Macaca mulatta*. The antibody or functional fragment of the invention preferably has an affinity to *Macaca mulatta* TNFα that is less than 20-fold, more particularly less than 10-fold different, even more particularly less than 5-fold different to its affinity to human TNFα. Typically, the antibody or functional fragment of the invention binds to TNFα from *Macaca mulatta* with a dissociation equilibrium constant ($K_D$), wherein the ratio $R_{M. mulatta}$ of (i) the $K_D$ for binding to TNFα from *Macaca mulatta* to (ii) the $K_D$ for binding to human TNFα is less than 20.

$$R_{M. mulatta} = \frac{K_D(M.\ mulatta)}{K_D(\text{human})}$$

$R_{M. mulatta}$ is preferably less than 20, particularly less than 10, even more particularly less than 5.

In yet another embodiment, the antibody or functional fragment of the invention is cross-reactive with TNFα from *Macaca fascicularis* and with TNFα from *Macaca mulatta*. The antibody or functional fragment of the invention preferably has an affinity to *Macaca fascicularis* TNFα that is less than 10-fold, particularly less than 5-fold, even more particularly less than 2-fold, or even less than 1.5-fold different to its affinity to human TNFα, and it preferably has an affinity to *Macaca mulatta* TNFα that is less than 20-fold, more particularly less than 10-fold, even more particularly less than 5-fold different to its affinity to human TNFα. The ratio $R_{M. fascicularis}$ of the antibody or functional fragment is preferably less than 10, particularly less than 5, even more particularly less than 2, or even less than 1.5, and the ratio $R_{M. mulatta}$ of the antibody or functional fragment is preferably less than 20, particularly less than 10, even more particularly less than 5.

Potency to Inhibit TNFα-Induced Apoptosis of L929 Cells

The antibody or functional fragment of the invention has a high potency to inhibit TNFα-induced apoptosis of L929 cells. In a particular embodiment, the antibody or functional fragment of the invention has a potency to inhibit TNFα-induced apoptosis of L929 cells greater than that of the known antibody infliximab.

Potency relative to infliximab can be determined in an L929 assay as described in Example 2, section 2.1.2 of this application. The relative potency of the antibody or functional fragment of the invention is greater than 1.5, preferably greater than 2, more preferably greater than 3, more preferably greater than 5, more preferably greater than 7.5, or even greater than 10, wherein the relative potency is the ratio of (i) the $IC_{50}$ value of infliximab in an L929 assay over (ii) the $IC_{50}$ value of the antibody or functional fragment of the invention in the L929 assay, and wherein the $IC_{50}$ indicates the concentration in ng/mL of the respective molecule necessary to achieve 50% of maximal inhibition of TNF-induced apoptosis of L929 cells.

In another embodiment, the relative potency of the antibody or functional fragment of the invention is greater than 1.5, preferably greater than 2, more preferably greater than 3, more preferably greater than 5, more preferably greater than 7.5, or even greater than 10, wherein the relative potency is the ratio of (i) the $IC_{90}$ value of infliximab in an L929 assay over (ii) the $IC_{90}$ value of the antibody or functional fragment of the invention in the L929 assay, and wherein the $IC_{90}$ value indicates the concentration in ng/mL of the respective molecule necessary to achieve 90% of maximal inhibition of TNF-induced apoptosis of L929 cells.

Inhibition of LPS-Induced Cytokine Secretion

The antibody or functional fragment of the invention may be capable of inhibiting LPS-induced cytokine secretion from monocytes. LPS-induced cytokine secretion from monocytes can be determined as described in Example 7.

In one embodiment, the antibody or functional fragment of the invention is capable of inhibiting LPS-induced secretion of interleukin-1β from $CD14^+$ monocytes. The $IC_{50}$ value for inhibiting LPS-induced secretion of interleukin-1β may be less than 1 nM and/or less than 100 pg/mL. The $IC_{50}$ value for inhibiting LPS-induced secretion of interleukin-1β, on a molar basis and/or on a weight-per-volume basis, may be lower than that of adalimumab.

In another embodiment, the antibody or functional fragment of the invention is capable of inhibiting LPS-induced secretion of TNFα from $CD14^+$ monocytes. The $IC_{50}$ value for inhibiting LPS-induced secretion of TNFα may be less than 1 nM and/or less than 150 pg/mL. The $IC_{50}$ value for inhibiting LPS-induced secretion of TNFα, on a molar basis and/or on a weight-per-volume basis, may be lower than that of adalimumab.

Inhibition of Cell Proliferation

The antibody or functional fragment of the invention may be capable of inhibiting cell proliferation of peripheral blood mononuclear cells in a mixed lymphocyte reaction. The inhibition of cell proliferation can be determined as described in Example 6. The stimulation index of the antibody or functional fragment, e.g. of the scFv or diabody of the invention, determined according to Example 6, may be less than 5, or less than 4.5. In particular embodiments, the stimulation index of the antibody, e.g. of the IgG of the invention, is less than 4 or even less than 3.

Inhibition of Interaction Between TNFα and TNF Receptor

Typically, the antibody or functional fragment of the invention is capable of inhibiting the interaction between human TNFα and TNF receptor I (TNFRI). The inhibition of the interaction between human TNFα and TNFRI can be determined in an inhibition ELISA as described below in Example 2, section 2.1.3.

The potency of the antibody or functional fragment of the invention to inhibit the interaction between human TNFα and TNFRI, relative to that of infliximab (relative potency), as determined in an inhibition ELISA, is preferably at least 1.3, wherein said relative potency is the ratio of the $IC_{50}$ value in ng/mL of infliximab to the $IC_{50}$ value in ng/mL of the antibody or functional fragment thereof.

Typically, the antibody or functional fragment of the invention is capable of inhibiting the interaction between human TNFα and TNF receptor II (TNFRII). The inhibition of the interaction between human TNFα and TNFRII can be determined in an inhibition ELISA as described below in Example 2, section 2.1.3.

The potency of the antibody or functional fragment of the invention to inhibit the interaction between human TNFα and TNFRII, relative to that of infliximab (relative potency), as determined in an inhibition ELISA, is preferably at least 1.3, wherein said relative potency is the ratio of the $IC_{50}$ value in ng/mL of infliximab to the $IC_{50}$ value in ng/mL of the antibody or functional fragment thereof.

Stoichiometry and Crosslinking

The antibody or functional fragment of the invention is typically capable of binding to human $TNFα_{Trimer}$ in a stoichiometry (antibody: $TNFα_{Trimer}$) of at least 2. The stoichiometry (antibody: $TNFα_{Trimer}$) is preferably greater than 2, or at least 2.5, or at least 3. In one embodiment, the stoichiometry (antibody: $TNFα_{Trimer}$) is about 3. The stoichiometry (antibody: $TNFα_{Trimer}$) can be determined as described in Example 4 below.

In another embodiment, the antibody or functional fragment of the invention is capable of forming a complex with human TNFα, wherein said complex comprises at least two molecules of TNFα and at least three molecules of antibody or functional fragment. The functional fragment in accordance with this embodiment comprises at least two separate binding sites for TNFα such as, e.g. diabodies. Complex formation can be determined as described in Example 5 below.

In one embodiment, the antibody is an IgG, and is capable of forming a complex of at least 600 kDa with TNFα. In another embodiment, the functional fragment is a diabody, and is capable of forming a complex of at least 300 kDa with TNFα.

Target Selectivity

In certain embodiments, the antibody or the functional fragment of the invention has a high target selectivity, i.e. it can discriminate between TNFα and TNFβ. Preferably, the $IC_{50}$ value of TNFβ is at least 1,000 times greater than the $IC_{50}$ value of TNFα, as determined in a competition ELISA as described in Example 2, section 2.1.4. More preferably, the $IC_{50}$ value of TNFβ is at least 5,000 times, most preferably at least 10,000 greater than the $IC_{50}$ value of TNFα, as determined in a competition ELISA as described in Example 2, section 2.1.4.

Expression Yield and Refolding Yield

In other embodiments, the antibody or functional fragment of the invention, preferably the scFv or diabody, can be recombinantly expressed in high yield in microorganisms such as bacteria or in other cells. Preferably, the expression yield in E. coli, determined as described in Example 2, is at least 0.25 g/L. This particularly applies to functional fragments such as scFvs.

The refolding yield, determined as described in Example 2, is at least 5 mg/L, more preferably at least 10 mg/L, more preferably at least 15 mg/L, and most preferably at least 20 mg/L. This particularly applies to functional fragments such as scFvs.

Stability

Typically, the antibody or functional fragment of the invention, preferably the scFv or diabody, has a high stability. Stability can be assessed by different methodologies. The "melting temperature" $T_m$ of the variable domain of the antibody or functional fragment of the invention, determined by differential scanning fluorimetry (DSF) as described in Example 2, section 2.2.4, is preferably at least 65° C., more preferably at least 68° C., more preferably at least 70° C., most preferably at least 74° C. The "melting temperature of the variable domain", as used herein, refers to the melting temperature of an scFv consisting of the sequence $V_L$-LinkerA-$V_H$, wherein the amino acid sequence of LinkerA consists of the amino acid sequence as shown in SEQ ID NO:29. For example, the melting temperature of the variable domain of an IgG is defined as the melting temperature of its corresponding scFv as defined above.

The loss in monomer content (at a concentration of 10 g/L; initial monomer content >95%) after storage for four weeks at 4° C., determined by analytical size-exclusion chromatography as described in Example 2, section 2.2.5, is preferably less than 5%, more preferably less than 3%, more preferably less than 1%, most preferably less than 0.5%. The loss in monomer content (at a concentration of 10 g/L; initial monomer content >95%) after storage for four weeks at −20° C., determined by analytical size-exclusion chromatography as described in Example 2, section 2.2.5, is preferably less than 5%, more preferably less than 3%, more preferably less than 1%, most preferably less than 0.5%. The loss in monomer content (at a concentration of 10 g/L; initial monomer content >95%) after storage for four weeks at −65° C., determined by analytical size-exclusion chromatography as described in Example 2, section 2.2.5, is preferably less than 5%, more preferably less than 3%, more preferably less than 1%, most preferably less than 0.5%.

The monomer loss after five consecutive freeze-thaw cycles, determined as described in Example 2, is less than 5%, more preferably less than 1%, more preferably less than 0.5%, most preferably less than 0.2%, e.g. 0.1% or 0.0%.

Antibodies and Functional Fragments

Particular embodiments of the invention relate to functional fragments of the antibodies described herein. Functional fragments include, but are not limited to, F(ab')$_2$ fragment, a Fab fragment, scFv, diabodies, triabodies and tetrabodies. Preferably, the functional fragment is a single chain antibody (scFv) or a diabody. More preferably, the non-CDR sequences of the scFv or of the diabody are human sequences.

Preferably in order to minimize potential for immunogenicity in humans the chosen acceptor scaffold is composed of framework regions derived from human consensus sequences or human germline sequences. In particular framework regions I to III of the variable light domain consist of human Vκ1 consensus sequences according to SEQ ID NOs: 31 to 33 and a framework region IV of a λ germline-based sequence selected from SEQ ID NOs:34 to 37. As residues that are not human consensus or human germline residues may cause immune reactions the number of such residues in each variable domain (VH or VL) should be as low as possible, preferably lower than 7, more preferably lower than 4, most preferably 0.

Preferably the antibody is a monoclonal antibody. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Monoclonal antibodies can be prepared using a wide variety of techniques known in the art including the use of hybridoma, recombinant, and phage display technologies, or a combination thereof. (Harlow and Lane, "Antibodies, A Laboratory Manual" CSH Press 1988, Cold Spring Harbor N.Y.).

In other embodiments, including embodiments relating to the in vivo use of the anti-TNFα antibodies in humans, chimeric, primatized, humanized, or human antibodies can be used. In a preferred embodiment, the antibody is a human antibody or a humanized antibody, more preferably a monoclonal human antibody or a monoclonal humanized antibody.

The term "chimeric" antibody as used herein refers to an antibody having variable sequences derived from a non-human immunoglobulin, such as a rat or mouse antibody, and human immunoglobulins constant regions, typically chosen from a human immunoglobulin template. Methods for producing chimeric antibodies are known in the art. See, e.g., Morrison, 1985, Science 229(4719): 1202-7; Oi et al, 1986, BioTechniques 4:214-221; Gillies et al., 1985, J. Immunol. Methods 125: 191-202; U.S. Pat. Nos. 5,807,715; 4,816,567; and 4,816397, which are incorporated herein by reference in their entireties.

Different recombinant methodologies are available to one of ordinary skill in the art to render a non-human (e.g., murine) antibody more human-like by generating immunoglobulins, immunoglobulin chains or fragments thereof (such as Fv, Fab, Fab', F(ab')$_2$ or other target-binding subsequences of antibodies), which contain minimal sequences derived from such non-human immunoglobulin. In general, the resulting recombinant antibody will comprise substantially all of at least one, and typically two, variable domains, in which all or substantially all of the CDR regions correspond to those of a non-human immunoglobulin and all or substantially all of the FR regions are those of a human immunoglobulin sequence, particularly a human immunoglobulin consensus sequence. CDR-grafted antibodies are antibody molecules having one or more complementarity determining regions (CDRs) from an antibody originally generated in a non-human species that bind the desired antigen and framework (FR) regions from a human immunoglobulin molecule (EP239400; PCT publication WO 91/09967; U.S. Pat. Nos. 5,225,539; 5,530,101 and 5,585,089). Often, in a process called "humanization", framework residues in the human framework regions will additionally be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., Riechmann et al., 1988, Nature 332: 323-7 and Queen et al, U.S. Pat. Nos. 5,530,101; 5,585,089; 5,693,761; 5,693,762; and 6,180,370 (each of which is incorporated by reference in its entirety). Antibodies can be rendered more human using a variety of additional techniques known in the art including, for example, veneering or resurfacing (EP592106; EP519596; Padlan, 1991, Mol. Immunol, 28:489-498; Studnicka et al, 1994, Prot. Eng. 7:805-814; Roguska et al, 1994, Proc. Natl. Acad. Sci. 91:969-973, and chain shuffling (U.S. Pat. No. 5,565,332), all of which are hereby incorporated by reference in their entireties. A CDR-grafted or humanized antibody can also comprise at least a portion of an immunoglobulin constant region (Fc), typically that of a human immunoglobulin template chosen.

In some embodiments, humanized antibodies are prepared as described in Queen et al, U.S. Pat. Nos. 5,530,101; 5,585,089; 5,693,761; 5,693,762; and 6,180,370 (each of which is incorporated by reference in its entirety).

In some embodiments, the anti-TNFα antibodies are human antibodies. Completely "human" anti-TNFα antibodies can be desirable for therapeutic treatment of human patients. As used herein, "human antibodies" include antibodies having the amino acid sequence of a human immunoglobulin and include antibodies isolated from human immunoglobulin libraries or from animals transgenic for one or more human immunoglobulin and that do not express endogenous immunoglobulins. Human antibodies can be made by a variety of methods known in the art including phage display methods described above using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety. Human antibodies can also be produced using transgenic mice which are incapable of expressing functional endogenous immunoglobulins, but which can express human immunoglobulin genes. See, e.g., PCT publications WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entireties. Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope (Jespers et al, 1988, Biotechnology 12:899-903).

In some embodiments, the anti-TNFα antibodies are primatized antibodies. The term "primatized antibody" refers to an antibody comprising monkey variable regions and human constant regions. Methods for producing primatized antibodies are known in the art. See e.g., U.S. Pat. Nos.

5,658,570; 5,681,722; and 5,693,780, which are incorporated herein by reference in their entireties.

In some embodiments, the anti-TNFα antibodies are derivatized antibodies. For example, but not by way of limitation, the derivatized antibodies that have been modified, e.g., by glycosylation, acetylation, pegylation, phosphorylation, amidation, derivatization by known protecting/blocking groups, proteolytic cleavage, linkage to a cellular ligand or other protein (see below for a discussion of antibody conjugates), etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

In yet other aspects, an anti-TNFα antibody has one or more amino acids inserted into one or more of its hypervariable region, for example as described in US 2007/0280931.

Antibody Conjugates

In some embodiments, the anti-TNFα antibodies are antibody conjugates that are modified, e.g., by the covalent attachment of any type of molecule to the antibody, such that covalent attachment does not interfere with binding to TNFα. Techniques for conjugating effector moieties to antibodies are well known in the art (See, e.g., Hellstrom et al., Controlled Drag Delivery, 2nd Ed., at pp. 623-53 (Robinson et al., eds., 1987)); Thorpe et al., 1982, Immunol. Rev. 62: 119-58 and Dubowchik et al., 1999, Pharmacology and Therapeutics 83:67-123).

In one example, the antibody or fragment thereof is fused via a covalent bond (e.g., a peptide bond), at optionally the N-terminus or the C-terminus, to an amino acid sequence of another protein (or portion thereof; preferably at least a 10, 20 or 50 amino acid portion of the protein). Preferably the antibody, or fragment thereof, is linked to the other protein at the N-terminus of the constant domain of the antibody. Recombinant DNA procedures can be used to create such fusions, for example as described in WO 86/01533 and EP0392745. In another example the effector molecule can increase half-life in vivo. Examples of suitable effector molecules of this type include polymers, albumin, albumin binding proteins or albumin binding compounds such as those described in WO 2005/117984.

In some embodiments, anti-TNFα antibodies can be attached to poly(ethyleneglycol) (PEG) moieties. For example, if the antibody is an antibody fragment, the PEG moieties can be attached through any available amino acid side-chain or terminal amino acid functional group located in the antibody fragment, for example any free amino, imino, thiol, hydroxyl or carboxyl group. Such amino acids can occur naturally in the antibody fragment or can be engineered into the fragment using recombinant DNA methods. See for example U.S. Pat. No. 5,219,996. Multiple sites can be used to attach two or more PEG molecules. Preferably PEG moieties are covalently linked through a thiol group of at least one cysteine residue located in the antibody fragment. Where a thiol group is used as the point of attachment, appropriately activated effector moieties, for example thiol selective derivatives such as maleimides and cysteine derivatives, can be used.

In another example, an anti-TNFα antibody conjugate is a modified Fab' fragment which is PEGylated, i.e., has PEG (poly(ethyleneglycol)) covalently attached thereto, e.g., according to the method disclosed in EP0948544. See also Poly(ethyleneglycol) Chemistry, Biotechnical and Biomedical Applications, (J. Milton Harris (ed.), Plenum Press, New York, 1992); Poly(ethyleneglycol) Chemistry and Biological Applications, (J. Milton Harris and S. Zalipsky, eds., American Chemical Society, Washington D.C., 1997); and Bioconjugation Protein Coupling Techniques for the Biomedical Sciences, (M. Aslam and A. Dent, eds., Grove Publishers, New York, 1998); and Chapman, 2002, Advanced Drug Delivery Reviews 54:531-545.

Pharmaceutical Compositions and Treatment

Treatment of a disease encompasses the treatment of patients already diagnosed as having any form of the disease at any clinical stage or manifestation; the delay of the onset or evolution or aggravation or deterioration of the symptoms or signs of the disease; and/or preventing and/or reducing the severity of the disease.

A "subject" or "patient" to whom an anti-TNFα antibody or functional fragment thereof is administered can be a mammal, such as a non-primate (e.g., cow, pig, horse, cat, dog, rat, etc.) or a primate (e.g., monkey or human). In certain aspects, the human is a pediatric patient. In other aspects, the human is an adult patient.

Compositions comprising an anti-TNFα antibody and, optionally one or more additional therapeutic agents, such as the second therapeutic agents described below, are described herein. The compositions typically are supplied as part of a sterile, pharmaceutical composition that includes a pharmaceutically acceptable carrier. This composition can be in any suitable form (depending upon the desired method of administering it to a patient).

The anti-TNFα antibodies and functional fragments can be administered to a patient by a variety of routes such as orally, transdermally, subcutaneously, intranasally, intravenously, intramuscularly, intrathecally, topically or locally. The most suitable route for administration in any given case will depend on the particular antibody, the subject, and the nature and severity of the disease and the physical condition of the subject. Typically, an anti-TNFα antibody or functional fragment thereof will be administered intravenously.

In a particularly preferred embodiment, the antibody or functional fragment of the invention is administered orally. If the administration is via the oral route the functional fragment is preferably a single chain antibody (scFv), diabody or IgG.

In typical embodiments, an anti-TNFα antibody or functional fragment is present in a pharmaceutical composition at a concentration sufficient to permit intravenous administration at 0.5 mg/kg body weight to 20 mg/kg body weight. In some embodiments, the concentration of antibody or fragment suitable for use in the compositions and methods described herein includes, but is not limited to, 0.5 mg/kg, 0.75 mg/kg, 1 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, or a concentration ranging between any of the foregoing values, e.g., 1 mg/kg to 10 mg/kg, 5 mg/kg to 15 mg/kg, or 10 mg/kg to 18 mg/kg.

The effective dose of an anti-TNFα antibody or functional fragment can range from about 0.001 to about 750 mg/kg per single (e.g., bolus) administration, multiple administrations or continuous administration, or to achieve a serum concentration of 0.01-5000 μg/mL serum concentration per single (e.g., bolus) administration, multiple administrations or continuous administration, or any effective range or value therein depending on the condition being treated, the route of administration and the age, weight and condition of the subject. In certain embodiments, each dose can range from about 0.5 mg to about 50 mg per kilogram of body weight or from about 3 mg to about 30 mg per kilogram body weight. The antibody can be formulated as an aqueous solution.

Pharmaceutical compositions can be conveniently presented in unit dose forms containing a predetermined amount of an anti-TNFα antibody or functional fragment per dose. Such a unit can contain 0.5 mg to 5 g, for example, but without limitation, 1 mg, 10 mg, 20 mg, 30 mg, 40 mg, 50 mg, 100 mg, 200 mg, 300 mg, 400 mg, 500 mg, 750 mg, 1000 mg, or any range between any two of the foregoing values, for example 10 mg to 1000 mg, 20 mg to 50 mg, or 30 mg to 300 mg. Pharmaceutically acceptable carriers can take a wide variety of forms depending, e.g., on the condition to be treated or route of administration.

Determination of the effective dosage, total number of doses, and length of treatment an anti-TNFα antibody or functional fragment thereof is well within the capabilities of those skilled in the art, and can be determined using a standard dose escalation study.

Therapeutic formulations of the anti-TNFα antibodies and functional fragments suitable in the methods described herein can be prepared for storage as lyophilized formulations or aqueous solutions by mixing the antibody having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives must be nontoxic to the recipients at the dosages and concentrations employed.

Buffering agents help to maintain the pH in the range which approximates physiological conditions. They can present at concentration ranging from about 2 mM to about 50 mM. Suitable buffering agents include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives can be added to retard microbial growth, and can be added in amounts ranging from 0.2%-1% (w/v). Suitable preservatives include phenol, benzyl alcohol, meta-cresol, methyl paraben, propyl paraben, octadecyldimethyl-benzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions and include polyhydric sugar alcohols, preferably trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers can be present in the range from 0.1 to 10,000 weights per part of weight active protein.

Non-ionic surfactants or detergents (also known as "wetting agents") can be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic polyols, polyoxyethylene sorbitan monoethers (TWEEN®-20, TWEEN®-80, etc.). Non-ionic surfactants can be present in a range of about 0.05 mg/mL to about 1.0 mg/mL, or in a range of about 0.07 mg/mL to about 0.2 mg/mL.

Additional miscellaneous excipients include bulking agents (e.g., starch), chelating agents (e.g., EDTA), antioxidants (e.g., ascorbic acid, methionine, vitamin E), protease inhibitors and co-solvents.

The formulation herein can also contain a second therapeutic agent in addition to an anti-TNFα antibody or functional fragment thereof. Examples of suitable second therapeutic agents are provided below.

The dosing schedule can vary from once a month to daily depending on a number of clinical factors, including the type of disease, severity of disease, and the patient's sensitivity to the anti-TNFα antibody or functional fragment. In specific embodiments, an anti-TNFα antibody or functional fragment thereof is administered daily, twice weekly, three times a week, every other day, every 5 days, every 10 days, every two weeks, every three weeks, every four weeks or once a month, or in any range between any two of the foregoing values, for example from every four days to every month, from every 10 days to every two weeks, or from two to three times a week, etc.

The dosage of an anti-TNFα antibody or functional fragment to be administered will vary according to the particular antibody, the subject, and the nature and severity of the disease, the physical condition of the subject, the therapeutic regimen (e.g., whether a second therapeutic agent is used), and the selected route of administration; the appropriate dosage can be readily determined by a person skilled in the art.

It will be recognized by one of skill in the art that the optimal quantity and spacing of individual dosages of an anti-TNFα antibody or functional fragment thereof will be determined by the nature and extent of the condition being treated, the form, route and site of administration, and the age and condition of the particular subject being treated, and that a physician will ultimately determine appropriate dosages to be used. This dosage can be repeated as often as appropriate. If side effects develop the amount and/or frequency of the dosage can be altered or reduced, in accordance with normal clinical practice.

Disorders to be Treated

The invention relates to a method of treating or preventing a human TNFα-related disease in a subject, comprising administering to the subject the antibody or functional fragment as defined herein. The term "TNF-related disorder" or "TNF-related disease" refers to any disorder, the onset, progression or the persistence of the symptoms or disease states of which requires the participation of TNFα. Exemplary TNF-related disorders include, but are not limited to, chronic and/or autoimmune states of inflammation in general, immune mediated inflammatory disorders in general, inflammatory CNS disease, inflammatory diseases affecting the eye, joint, skin, mucous membranes, central nervous system, gastrointestinal tract, urinary tract or lung, states of uveitis in general, retinitis, HLA-B27+ uveitis, Behçet's disease, dry eye syndrome, glaucoma, Sjögren syndrome, diabetes mellitus (incl. diabetic neuropathy), insulin resistance, states of arthritis in general, rheumatoid arthritis, osteoarthritis, reactive arthritis and Reiter's syndrome, juvenile arthritis, ankylosing spondylitis, multiple sclerosis, Guillain-Barré syndrome, myasthenia gravis, amyotrophic lateral sclerosis, sarcoidosis, glomerulonephritis, chronic kidney disease, cystitis, psoriasis (incl. psoriatic arthritis), hidradenitis suppurativa, panniculitis, pyoderma gangrenosum, SAPHO syndrome (synovitis, acne, pustulosis, hyperostosis and osteitis), acne, Sweet's sydrome, pemphigus, Crohn's disease (incl. extraintestinal manifestastations), ulcerative colitis, asthma bronchiale, hypersensitivity pneumonitis, general allergies, allergic rhinitis, allergic sinusitis, chronic obstructive pulmonary disease (COPD), lung fibrosis, Wegener's granulomatosis, Kawasaki syndrome, Giant cell arteritis, Churg-Strauss vasculitis, polyarteritis nodosa, burns, graft versus host disease, host versus graft reactions, rejection episodes following organ or bone marrow transplantation, systemic and local states of vasculitis in general, systemic and cutaneous lupus erythematodes, polymyositis and dermatomyositis, sclerodermia, pre-eclampsia, acute and chronic pancreatitis, viral hepatitis, alcoholic hepatitis, postsurgical inflammation such as after eye surgery (e.g. cataract (eye lens replacement) or glaucoma surgery), joint surgery (incl. arthroscopic surgery), surgery at joint-related structures (e.g. ligaments), oral and/or dental surgery, minimally invasive cardiovascular procedures (e.g. PTCA, atherectomy, stent placement), laparoscopic and/or endoscopic intra-abdominal and gynecological procedures, endoscopic urological procedures (e.g. prostate surgery, ureteroscopy, cystoscopy, interstitial cystitis), or perioperative inflammation (prevention) in general, bullous dermatitis, neutrophilic dermatitis, toxic epidermal necrolysis, pustular dermatitis, cerebral malaria, hemolytic uremic syndrome, allograft rejection, otitis media, snakebite, erythema nodosum, myelodysplastic syndromes, primary sclerosing cholangitis, seronegative spondylartheropathy, autoimmune hematolytic anemia, orofacial granulamatosis, pyostomatitis vegetans, aphthous stomatitis, geographic tongue, migratory stoimatitis, Alzheimer disease, Parkinson's disease, Huntington's disease, Bell's palsy, Creutzfeld-Jakob disease and neuro-degenerative conditions in general.

Cancer-related osteolysis, cancer-related inflammation, cancer-related pain, cancer-related cachexia, bone metastases, acute and chronic forms of pain, irrespective whether these are caused by central or peripheral effects of TNFα and whether they are classified as inflammatory, nociceptive or neuropathic forms of pain, sciatica, low back pain, carpal tunnel syndrome, complex regional pain syndrome (CRPS), gout, postherpetic neuralgia, fibromyalgia, local pain states, chronic pain syndroms due to metastatic tumor, dismenorrhea.

Particular disorders to be treated include states of arthritis in general, rheumatoid arthritis, osteoarthritis, reactive arthritis, juvenile arthritis; psoriasis incl. psoriatic arthritis; inflammatory bowel disease, including Crohn's disease, ulcerative colitis incl. proctitis, sigmoiditis, left-sided colitis, extensive colitis and pancolitis, undetermined colitis, microscopic colitis incl. collagenous and lymphocytic colitis, colitis in connective tissue disease, diversion colitis, colitis in diverticular disease, eosinophilic colitis and pouchitis.

Most preferably, the antibody or functional fragment of the invention is used to treat an inflammatory bowel disease, in particular Crohn's disease, ulcerative colitis or microscopic colitis. The Crohn's disease may be ileal, colonic, ileocolonic or isolated upper Crohn's disease (gastric, duodenal and/or jejunal) including non-stricturing/non-penetrating, stricturing, penetrating and perianal disease behavior, allowing any combination of localization and disease behavior of any of the above mentioned. The ulcerative colitis may be ulcerative proctitis, proctosigmoiditis, left-sided colitis, pan-ulcerative colitis and pouchitis.

Combination Therapy and Other Aspects

Preferably, the patient being treated with an anti-TNFα antibody or functional fragment thereof is also treated with another conventional medicament. For example, a patient suffering from inflammatory bowel disease, especially if having moderate to severe disease is typically also being treated with mesalazine or derivatives or prodrugs thereof, corticosteroids, e.g. budesonide or prednisolone (oral or i.v.), immunosuppressants, e.g. azathioprine/6-mercaptopurine (6-MP) or methotrexate, cyclosporine or tacrolimus. Other medicaments which can be co-administered to the patient include biologics such as infliximab, adalimumab, etanercept, certolizumab pegol or others. Further medicaments which can be co-administered to the patient include immunosupressants (e.g. azathioprine/6-MP or methotrexate or oral cyclosporine) in order to maintain stable and longer remission. Yet another aspect of the invention is the use of an anti-TNFα antibody or functional fragment as defined hereinabove for reducing inflammation.

Yet another aspect of the invention is an anti-TNFα antibody or functional fragment as defined hereinabove for use in reducing inflammation in a patient suffering from an inflammatory condition.

A further aspect of this invention is a method of treating an inflammatory condition, comprising administering to a patient in need thereof an effective amount of an anti-TNFα antibody or functional fragment as defined hereinabove. The inflammatory condition is preferably one of the conditions described above.

TABLE 1

Summary of the amino acid sequences

| SEQ ID NO: | Description |
|---|---|
| 1 | Generic CDR L1 |
| 2 | Generic CDR L2 |
| 3 | Generic CDR L3 |
| 4 | Generic CDR H1 |
| 5 | Generic CDR H2 |
| 6 | CDR H3 of clones 17-22-B03, 16-12-E09, 16-13-E01, 16-15-E11, 16-17-C08, 16-17-G01, 17-18-D10 and 17-22-B01 |
| 7 | CDR L1 of clones 17-22-B03, 16-12-E09, 16-13-E01, 16-15-E11 and 17-18-D10 |
| 8 | CDR L2 of clones 17-22-B03, 16-12-E09, 16-15-E11, 16-17-C08, 16-17-G01 and 17-18-D10 |
| 9 | CDR L3 of clones 17-22-B03, 16-12-E09, 16-13-E01, 16-15-E11, 16-17-C08, 16-17-G01, 17-18-D10 and 17-22-B01 |
| 10 | CDR H1 of clones 17-22-B03, 16-12-E09, 16-13-E01, 16-15-E11, 16-17-C08, 17-18-D10 and 17-22-B01 |
| 11 | CDR H2 of clones 17-22-B03 and 16-17-C08 |
| 12 | CDR H2 of clone 16-12-E09 |
| 13 | CDR L2 of clone 16-13-E01 |
| 14 | CDR H2 of clones 16-13-E01 and 17-18-D10 |
| 15 | CDR H2 of clones 16-15-E11, 16-17-G01 and 17-22-B01 |
| 16 | CDR L1 of clone 16-17-C08 |
| 17 | CDR L1 of clone 16-17-G01 |
| 18 | CDR H1 of clone 16-17-G01 |
| 19 | CDR L1 of clone 17-22-B01 |
| 20 | CDR L2 of clone 17-22-B01 |
| 21 | $V_H$ of humanized scFv of clones 17-22-B03-sc02, 17-22-B03-sc08, 17-22-B03-sc12 |
| 22 | $V_L$ of humanized scFv of clone 17-22-B03-sc02 |
| 23 | $V_L$ of humanized scFv of clone 17-22-B03-sc08 |
| 24 | $V_L$ of humanized scFv of clone 17-22-B03-sc12 |
| 25 | Humanized scFv of clone 17-22-B03-sc02 |
| 26 | Humanized scFv of clone 17-22-B03-sc08 |
| 27 | Humanized scFv of clone 17-22-B03-sc12 |
| 28 | Generic CDR L3 where Cys2 (X) is limited to Arg, His, Pro, Phe, Gln, Gly, Ser, Thr, Asn and Tyr |
| 29 | Linker sequence in scFv |
| 30 | Linker sequence in diabody |
| 31 | Vκ1 consensus sequence of framework I (Kabat positions 1-23) (see Table 10) |
| 32 | Vκ1 consensus sequence of framework II (Kabat positions 35-49) (see Table 10) |
| 33 | Vκ1 consensus sequence of framework III (Kabat positions 57-88) (see Table 10) |
| 34 | Vλ germline-based sequence of framework IV (see Table 11) |
| 35 | Vλ germline-based sequence of framework IV (see Table 11) |
| 36 | Vλ germline-based sequence of framework IV (see Table 11) |
| 37 | Vλ germline-based sequence of framework IV (see Table 11) |

EXAMPLES

Example 1: Generation of Rabbit Antibodies Directed Against Human TNFα

1. Results
1.1 Immunization

Rabbits have been immunized with purified recombinant human TNFα (Peprotech, Cat. No. 300-01A). During the course of the immunization, the strength of the humoral immune response against the antigen was qualitatively assessed by determining the maximal dilution (titer) for the serum of each rabbit that still produced detectable binding of the polyclonal serum antibodies to the antigen. Serum antibody titers against immobilized recombinant human TNFα were assessed using an enzyme-linked immunosorbent assay (ELISA, see 2.2.1). All three rabbits showed very high titers with a $10\times10^6$-fold dilution of the serum still resulting in a positive signal (at least 3-fold higher than the signal obtained with serum from a naïve unrelated animal which was used as background control) in the ELISA. In addition, the ability of different rabbit sera to inhibit the biological activity of TNFα was assessed using a mouse L929 cell-based assay (see 2.2.3). All three sera inhibited TNFα-induced apoptosis of mouse L929 fibroblasts. Rabbit #3 showed the strongest neutralizing activity with 50% inhibition ($IC_{50}$) reached at a serum dilution of 1:155'000. Compared to rabbit #3, rabbit #2 and rabbit #1 showed approximately 3 and 21-fold lower activity, reaching 50% inhibition at a serum dilution of 1:55'500 and 1:7'210, respectively.

Lymphocytes isolated from spleens of all three animals were chosen for the subsequent hit identification procedures. The animals were prioritized based on the potency to inhibit the biological activity of TNFα in the L929 assay. Therefore, the highest number of hits that were cultivated originated from rabbit #3, and the lowest number of hits was derived from rabbit #1.

1.2 Hit Identification
1.2.1 Hit Sorting

Prior to the hit identification procedure, a flow-cytometry-based sorting procedure was developed that specifically detects and allows for the isolation of high-affinity TNFα binding B-cells (see 2.1).

A total of $33\times10^6$ lymphocytes (corresponding to 1.5% of total lymphocytes isolated) derived from all three rabbits were characterized in two independent sorting campaigns. Out of the $33\times10^6$ cells analyzed in total 3452 B-cells expressing TNFα-specific antibodies (IgG) were isolated. The numbers of lymphocytes cloned were different for the three rabbits, as more cells were isolated from those rabbits whose sera showed strong inhibition of TNFα in the L929 assay. Of the isolated B-cells, 792 clones were derived from rabbit #1, 1144 clones from rabbit #2 and 1408 clones from rabbit #3. For 108 clones the respective rabbit origin is not known, because they are derived from a mixture of residual lymphocytes from all 3 rabbits to allow optimal recovery of small amount of lymphocytes from the vials.

1.2.2 Hit Screening

The results obtained during the screening phase are based on assays performed with non-purified antibodies from culture supernatants of antibody secreting cells (ASC), as the scale of the high-throughput culture does not allow for purification of the individual rabbit antibodies. Such supernatants were used to rank large numbers of antibodies relative to each other, however not to provide absolute values (e.g. for inhibition of biological activity of TNFα), except for binding affinity. ASC supernatants were screened in a high-throughput ELISA for binding to recombinant human TNFα. TNFα-binding supernatants were further characterized for binding to Cynomolgus monkey TNFα by ELISA, binding kinetics and for their potential to neutralize the biological activity of human TNFα in the L929 assay. With the exception of binding kinetics, the reporting values of the high-throughput screenings should be interpreted as "yes" or "no" answers, which are based on single-point measurements (no dose-response). Affinity to Cynomolgus monkey and mouse TNFα was analyzed for all the 102 clones that were selected for amplification and sequencing of the antibody heavy and light chain variable domains.

1.2.2.1 Binding to Human TNFα

The aim of the primary screening is to identify ASC clones that produce antibodies specific for human TNFα. For this purpose, cell culture supernatants of 3452 ASC clones were analysed for the presence of antibodies to human TNFα by ELISA (see 2.2.1). The ELISA method used assesses the "quantity" of antibodies of the IgG subtype bound to recombinant human TNFα, gives however no information about the affinity or the concentration of the antibodies. In this assay, supernatants from 894 ASC clones produced a signal that was clearly above background. The hit rate in screening was similar for rabbit #1 and rabbit #2 with 153 hits out of 792 (19.3%) identified from rabbit #1 and 225 hits out of 1144 identified from rabbit #2 (19.7%). Rabbit #3 showed a significantly higher hit rate of 34.4% resulting in the identification of 484 hits out of 1408. All 894 hits identified in this primary screening, were subjected to the measurement of binding kinetics by SPR (secondary screening).

1.2.2.2 TNFα Binding Kinetics

The aim of the secondary screening is to obtain quantitative information on the quality of target binding for each hit from the primary screening by surface plasmon resonance (SPR, see 2.2.2). In contrast to the ELISA used during the primary screening, this method assesses the kinetics of target binding as a function of time. This allows determination of the rate constants for association ($k_a$) and dissociation ($k_d$) of the antibody from its target. The ratio $k_d/k_a$ provides the equilibrium dissociation constant ($K_D$), which reflects the affinity of an antibody to its target. Of the 894 hits identified in the primary screening, binding affinities to human TNFα could be determined for 839 monoclonal rabbit antibodies. For the remaining 55 antibodies affinity could not be measured because the antibody concentration in the ASC supernatant was below the detection limit of the SPR instrument in the respective setup. The 839 anti-TNFα antibodies that could be measured showed dissociation constants ($K_D$) ranging from below $1.36 \times 10^{-13}$ M to $1.14 \times 10^{-8}$ M. 69% of all antibodies analyzed had a $K_D$ below 0.5 nM.

The median $K_D$s of $2.21 \times 10^{-10}$ M and $2.09 \times 10^{-10}$ M for screening hits identified from rabbits #2 and #3 were similar while rabbit #1 showed about 2-fold higher values with a median $K_D$ of $4.65 \times 10^{-10}$ M. When considering only neutralizing screening hits, the affinity distributions were similar for all three animals with lower values for the median $K_D$ (median $K_D$s between $1.4 \times 10^{-10}$ M and $1.27 \times 10^{-10}$ M). Affinities below 0.041 nM, 0.029 nM and 0.026 nM were measured for 5% of screening hits for rabbits #1, #2 and #3, respectively. For 2% of supernatants, affinities were even in the low picomolar range (below 6.2 pM, 7.9 pM and 11 pM). The excellent yield of high-affinity antibodies resulting from the secondary screening provides a broad basis for the selection of the most appropriate antibodies for humanization and reformatting.

1.2.2.3 Potency

For the assessment of potency, a cell-based assay (L929 assay) has been developed (see 2.2.3). 506 out of the 894 selected antibodies (56.6%), inhibited TNFα-induced apoptosis in the L929 assay by more than 50%. In line with results obtained during titer analysis, the highest percentage of neutralizing hits was derived from rabbit #3 with a hit rate of 62.8%, followed by rabbit #2 with a hit rate of 56.4% and rabbit #1 with the lowest hit rate of 39.9%. Affinities of these neutralizing antibodies ranged between $1.36 \times 10^{-13}$ to $1.19 \times 10^{-9}$ M.

1.2.2.4 Species Cross-Reactivity (Cynomolgus Monkey)

All 894 hits identified in the primary screening, were analyzed for species cross-reactivity to Cynomolgus monkey TNFα by ELISA (see 2.2.1). The aim of this additional screening was to allow selection of ASC clones that are known to cross-react with Cynomolgus monkey TNFα. The ELISA method used assesses the "quantity" of antibodies of the IgG subtype bound to recombinant Cynomolgus monkey TNFα, gives however no information about the affinity or the concentration of the antibodies. Supernatants from 414 (46%) ASC clones produced a clear signal (optical density (OD) ≥1). The percentage of hits cross-reactive to Cynomolgus monkey TNFα was similar for rabbit #1 and rabbit #3 with 81 hits out of 153 (52.9%) identified from rabbit #1 and 236 hits out of 484 identified from rabbit #3 (48.8%). With 37.8%, rabbit #2 showed a slightly lower percentage of cross-reactive hits resulting in the identification of 82 hits out of 225.

1.2.2.5 Selection of Clones for RT-PCR

As a prerequisite for hit confirmation, gene sequence analysis and subsequent humanization of the rabbit antibodies, the genetic information encoding the rabbit antibody variable domain needs to be retrieved. This was done by reverse transcription (RT) of the respective messenger RNA into the complementary DNA (cDNA), followed by amplification of the double stranded DNA by the polymerase chain reaction (PCR). The selection of ASC clones subjected to RT-PCR was primarily based on affinity and neutralizing activity. As additional criterion cross-reactivity to Cynomolgus monkey TNFα was considered. In total 102 ASC clones were selected for gene cloning by RT-PCR. First, the 93 best ranking ASC (in terms of affinity) with a $K_D$ below 80 pM, that inhibited the biological activity of TNFα in the L929 assay by more than 50% and that showed significant binding to Cynomolgus monkey TNFα were selected. Additionally, all the 9 best ranking ASC clones with $K_D$ below 20 pM that neutralized TNFα activity by more than 50% but did not bind to Cynomolgus monkey TNFα nevertheless were chosen as well. In total, 12, 13 and 66 ASC clones were successfully amplified and sequenced from rabbits #1, #2 and #3, respectively.

1.2.2.6 Identification of Related Clones with Desired Properties

In order to characterize the genetic diversity of the panel of isolated ASC clones the sequences of the complementary determining regions (CDRs) were extracted and subjected to a multiple sequence alignment thus allowing sequence clustering in a phylogenetic tree.

While this analysis on one hand allows the selection of a diverse set of clonal sequences to be carried forward into humanization and re-formatting experiments it also identifies homologous clusters of clonal sequences that appeared to share a common parental B-cell clone in the rabbit. The hallmark of these sequence clusters are high sequence homology in the CDRs and a consistent pattern of pharmacodynamic properties. Both of these features are summarized for a cluster of eight clones in Tables 2 and 3. Despite the functional conservation of this sequence cluster the consensus sequence in Table 3 reveals that a certain variability of the CDRs is tolerated, while still resulting in the desired pharmacodynamic profile.

TABLE 2

Pharmacodynamic properties of monoclonal antibodies in B-cell supernatants.

| | B-cell SN | | | | | | TNFα |
|---|---|---|---|---|---|---|---|
| | Affinity to human TNFα | | | Affinity to Cynomolgus TNFα | | | |
| Clone ID | $k_a$ ($M^{-1}s^{-1}$) | $K_d$ ($s^{-1}$) | $K_D$ (M) | $k_a$ ($M^{-1}s^{-1}$) | $K_d$ ($s^{-1}$) | $K_D$ (M) | neutralization % inhibition |
| 16-12-E09 | 2.37E+06 | 1.42E−04 | 5.99E−11 | 2.46E+06 | 1.29E−04 | 5.23E−11 | 80 |
| 16-13-E01 | 3.12E+06 | 1.37E−04 | 4.40E−11 | 3.26E+06 | 1.45E−04 | 4.44E−11 | 86 |
| 16-15-E11 | 4.16E+06 | 2.90E−04 | 6.97E−11 | 6.36E+06 | 3.39E−04 | 5.33E−11 | 72 |
| 16-17-C08 | 2.54E+06 | 1.03E−04 | 4.06E−11 | 5.01E+06 | 1.41E−04 | 2.81E−11 | 74 |

TABLE 2-continued

Pharmacodynamic properties of monoclonal antibodies in B-cell supernatants.

| | B-cell SN | | | | | | |
|---|---|---|---|---|---|---|---|
| | Affinity to human TNFα | | | Affinity to Cynomolgus TNFα | | | TNFα |
| Clone ID | $k_a$ $(M^{-1}s^{-1})$ | $K_d$ $(s^{-1})$ | $K_D$ (M) | $k_a$ $(M^{-1}s^{-1})$ | $K_d$ $(s^{-1})$ | $K_D$ (M) | neutralization % inhibition |
| 16-17-G01 | 2.20E+06 | 6.13E−05 | 2.79E−11 | 3.50E+06 | 9.42E−05 | 2.69E−11 | 94 |
| 17-18-D10 | 1.08E+06 | 6.72E−05 | 6.20E−11 | 2.37E+06 | 8.72E−05 | 3.69E−11 | 104 |
| 17-22-B01 | 1.48E+06 | 1.06E−04 | 7.15E−11 | 2.61E+06 | 1.25E−04 | 4.79E−11 | 104 |
| 17-22-B03 | 1.43E+06 | 1.03E−05 | 7.23E−12 | 2.40E+06 | 3.93E−05 | 1.64E−11 | 98 |

TABLE 3

The following sequence data regarding the CDRs were obtained for the above clones:

| CDR | clone | Sequence | SEQ ID NO: |
|---|---|---|---|
| CDR L1 | 17-22-B03 | QASQSISSYLA | 7 |
| | 16-12-E09 | QASQSISSYLA | 7 |
| | 16-13-E01 | QASQSISSYLA | 7 |
| | 16-15-E11 | QASQSISSYLA | 7 |
| | 16-17-C08 | QASQSIGSYLA | 16 |
| | 16-17-G01 | QASQSISNYLA | 17 |
| | 17-18-D10 | QASQSISSYLA | 7 |
| | 17-22-B01 | QASQSISSYLS | 19 |
| | Cons. Seq. | QASQSIXXYLX | 1 |
| CDR L2 | 17-22-B03 | KASTLAS | 8 |
| | 16-12-E09 | KASTLAS | 8 |
| | 16-13-E01 | QASTLAS | 13 |
| | 16-15-E11 | KASTLAS | 8 |
| | 16-17-C08 | KASTLAS | 8 |
| | 16-17-G01 | KASTLAS | 8 |
| | 17-18-D10 | KASTLAS | 8 |
| | 17-22-B01 | RASTLAS | 20 |
| | Generic | XASTLAS | 2 |
| CDR L3 | 17-22-B03 | QCTYYEPSYVFRA | 9 |
| | 16-12-E09 | QCTYYEPSYVFRA | 9 |
| | 16-13-E01 | QCTYYEPSYVFRA | 9 |
| | 16-15-E11 | QCTYYEPSYVFRA | 9 |
| | 16-17-C08 | QCTYYEPSYVFRA | 9 |
| | 16-17-G01 | QCTYYEPSYVFRA | 9 |
| | 17-18-D10 | QCTYYEPSYVFRA | 9 |
| | 17-22-B01 | QCTYYEPSYVFRA | 9 |
| | Generic | QXTYYEPSYVFRA | 3 |
| CDR H1 | 17-22-B03 | GIDFSAGYDMC | 10 |
| | 16-12-E09 | GIDFSAGYDMC | 10 |
| | 16-13-E01 | GIDFSAGYDMC | 10 |
| | 16-15-E11 | GIDFSAGYDMC | 10 |
| | 16-17-C08 | GIDFSAGYDMC | 10 |
| | 16-17-G01 | RIDFSAGYDMC | 18 |
| | 17-18-D10 | GIDFSAGYDMC | 10 |
| | 17-22-B01 | GIDFSAGYDMC | 10 |
| | Generic | XIDFSAGYDMC | 4 |
| CDR H2 | 17-22-B03 | CIDSRREESDYASWAKG | 11 |
| | 16-12-E09 | CIDSRSDNTDYASWAKG | 12 |
| | 16-13-E01 | CIDSRREDSDYASWAKG | 14 |
| | 16-15-E11 | CIDSRNDNTDYASWAKG | 15 |
| | 16-17-C08 | CIDSRREESDYASWAKG | 11 |
| | 16-17-G01 | CIDSRNDNTDYASWAKG | 15 |
| | 17-18-D10 | CIDSRREDSDYASWAKG | 14 |
| | 17-22-B01 | CIDSRNDNTDYASWAKG | 15 |
| | Generic | CIDSRXXXXDYASWAKG | 5 |
| CDR H3 | 17-22-B03 | GGYGGDGVDGAFDP | 6 |
| | 16-12-E09 | GGYGGDGVDGAFDP | 6 |
| | 16-13-E01 | GGYGGDGVDGAFDP | 6 |
| | 16-15-E11 | GGYGGDGVDGAFDP | 6 |
| | 16-17-C08 | GGYGGDGVDGAFDP | 6 |
| | 16-17-G01 | GGYGGDGVDGAFDP | 6 |
| | 17-18-D10 | GGYGGDGVDGAFDP | 6 |
| | 17-22-B01 | GGYGGDGVDGAFDP | 6 |
| | Generic | GGYGGDGVDGAFDP | 6 |

*Amino acids designated "X" have the meaning as defined in the accompanying sequence listing.

1.2.2.7 Cross-Reactivity to Cynomolgus Monkey TNFα (by SPR)

Because of the high number of high affinity hits that potently neutralized TNFα, species cross-reactivity was assessed for all monoclonal rabbit antibodies that were subjected to RT-PCR in order to facilitate the selection of ASC clones for Hit confirmation. Affinities to Cynomolgus monkey TNFα were determined by SPR measurements similarly as described above (see also 2.2.2). The affinities of the 93 tested antibodies for Cynomolgus monkey TNFα ranged from $9.6 \times 10^{-12}$ to $2.1 \times 10^{-9}$ M. 38 of the 93 cross-reactive antibodies bound human and Cynomolgus TNFα with similar affinity (less than two-fold difference in $K_D$). Moreover, the difference in affinity between human and Cynomolgus was less than 20-fold for 79 of the 93 cross-reactive antibodies and less than 10-fold for 62 of them, which makes them acceptable for the preclinical development in the Cynomolgus monkey.

2. Methods 2.1 Sorting Assay

Flow-cytometry based sorting procedure for the isolation of antigen-specific B-cells from rabbit lymphatic tissue was performed as outlined by Lalor et al (Eur J Immunol. 1992; 22.3001-2011)

2.2 Screening Assays 2.2.1 TNFα Binding ELISA (Human and Cynomolgus Monkey TNFα)

Recombinant human TNFα (Peprotech, Cat. No. 300-01) was coated on a 96 well microtiter ELISA plate. Binding of rabbit antibodies in the ASC culture supernatants to the immobilized TNFα was detected by a secondary HRP-labelled anti-rabbit IgG (JacksonImmuno Research, Cat. No. 111-035-046). TMB substrate (3,3',5,5'-tetramethylbenzidine, KPL, Cat. No. 53-00-00) was added and the colour reaction was stopped by the addition of $H_2SO_4$. Plates were read using a microtiter plate reader (Infinity reader M200 Pro, Tecan) at a wavelength of 450 nm.

Assay performance during the screening campaigns was monitored by a commercially available positive control anti-TNFα rabbit polyclonal antibody (AbD Serotec, Cat. No. 9295-0174). For this purpose the positive control antibody was tested at 100 and 250 ng/mL in duplicate on each screening plate. Robustness and precision of the response of the positive control was monitored for each plate. At the final assay conditions, the signal-to-background ratio was between 30 to 40 for the positive control at 250 ng/mL and coefficient of variation (CV) of the positive control were below 10%. A signal with an optical density of ≥100% relative to the 250 ng/mL positive control was considered as a primary screening hit.

For serum titer determinations, the same ELISA setup was used as described above. A serum dilution was considered positive when the binding signal of the immune serum was at least 3-fold higher compared to the signal of a naïve unrelated animal.

Species cross-reactivity to Cynomolgus monkey was determined using a similar ELISA as described above. Recombinant Cynomolgus monkey TNFα (Sino Biological, Cat. No. 90018-CNAE) was coated on 96 well microtiter ELISA plates. Binding of rabbit antibodies in the ASC culture supernatants to the immobilized Cynomolgus monkey TNFα was detected by the HRP-labelled secondary antibody as specified above. Immune serum from rabbit #2 was used as positive control at a dilution of 1:80'000 and 1:320'000. Robustness and precision of the response of the positive control was monitored for each plate. At the final assay conditions, the signal-to-background ratio was between 20 to 30 for the positive control at a dilution of 1:80'000 and CVs of the positive control were below 10%.

2.2.2 Binding Kinetics to TNFα by SPR (Human and Cynomolgus Monkey)

Binding affinities of antibodies towards human TNFα were measured by surface plasmon resonance (SPR) using a MASS-1 SPR instrument (Sierra Sensors). Performance of the instrument was qualified by means of standard reference solutions as well as by analysis of a reference antibody-antigen interaction such as infliximab-TNFα interaction.

For affinity screening, an antibody specific for the Fc region of rabbit IgGs (Bethyl Laboratories, Cat. No. A120-111A) was immobilized on a sensor chip (SPR-2 Affinity Sensor, High Capacity Amine, Sierra Sensors) using a standard amine-coupling procedure. Rabbit monoclonal antibodies in ASC supernatants were captured by the immobilized anti-rabbit IgG antibody. After capturing of the monoclonal antibodies, human TNFα (Peprotech, Cat. No. 300-01) was injected into the flow cells for 3 min at a concentration of 90 nM, and dissociation of the protein from the IgG captured on the sensor chip was allowed to proceed for 5 min. After each injection cycle, surfaces were regenerated with two injections of 10 mM Glycine-HCl. The apparent dissociation ($k_d$) and association ($k_a$) rate constants and the apparent dissociation equilibrium constant ($K_D$) were calculated with the MASS-1 analysis software (Analyzer, Sierra Sensors) using one-to-one Langmuir binding model and quality of the fits was monitored based on relative Chi$^2$ (Chi$^2$ normalized to the extrapolated maximal binding level of the analyte), which is a measure for the quality of the curve fitting. For most of the Hits the relative Chi$^2$ value was below 15%. Results were deemed valid if the response units (RU) for ligand binding were at least 2% of the RUs for antibody capturing. Samples with RUs for ligand binding with less than 2% of the RUs for antibody capturing were considered to show no specific binding of TNFα to the captured antibody. Species cross-reactivity to Cynomolgus monkey TNFα (Sino Biological, Cat. No. 90018-CNAE) was measured using the same assay setup and TNFα concentrations and applying the same quality measures. The relative Chi$^2$ was below 15% for most of the ASC supernatants analyzed.

2.2.3 TNFα-Induced Apoptosis in L929 Fibroblasts

The ability of rabbit IgGs from ASC culture supernatants to neutralize the biological activity of recombinant human TNFα was assessed using mouse L929 fibroblasts (ATCC/LGC Standards, Cat. No. CCL-1). L929 cells were sensitized to TNFα-induced apoptosis by addition of 1 µg/mL actinomycin D. Cells were cultured in 96-well flat-bottom microtiter plates in the presence of 50% ASC culture supernatant and 100 pM (5.2 ng/mL) human TNFα (Peprotech, Cat. No. 300-01) for 24 h. Compared to purified antibodies, higher concentrations of TNFα have to be used in the presence of ASC supernatants for hit screening. Survival of the cells was determined by a colorimetric assay using the WST-8 (2-(2-methoxy-4-nitrophenyl)-3-(4-nitrophenyl)-5-(2,4-disulfophenyl)-2H-tetrazolium, monosodium salt) cell proliferation reagent (Sigma Aldrich, Cat. No. 96992). WST-8 is reduced by cellular dehydrogenases to an orange formazan product. The amount of formazan produced is directly proportional to the number of living cells. Data were analyzed using a four-parameter logistic curve fit using the Softmax Data Analysis Software (Molecular Devices), and the concentration of infliximab required to neutralize TNFα-induced apoptosis by 50% ($IC_{50}$) was calculated at a concentration of 36.2 ng/mL. Therefore, the estimated lower limit of detection for this assay is between 30 to 40 ng/mL. This value is only a rough estimate for the detection limit, since the potential to block TNFα is not only dependent on the concentration of the monoclonal antibody but also on affinity of the antibody to the target. However, the sensitivity of the assay is sufficient for screening of ASC supernatants since IgG concentrations in most ASC supernatants are above a concentration of 40 ng/mL. Supernatants resulting in 50% neutralization of TNFα-induced apoptosis were considered positive.

To assure robust assay performance during the screening campaigns the positive control antibody infliximab was tested at 115 ng/mL (0.8 nM) and at 58 ng/mL (0.4 nM) in duplicates on each screening plate. Percent inhibition and precision of the response for the positive control was monitored for each screening plate. The acceptance criteria for each plate were set as follows: at least 60% inhibition with the positive control antibody at a concentration of 115 ng/mL with a coefficient of variation (CV) below 20%.

Example 2: Humanization and Generation of scFv

1. Results 1.1 Hit Confirmation & Selection of Hits for Humanization 73 unique sets of parental rabbit light and heavy chain variable domains were retrieved during hit screening and analyzed by sequence alignment. Based on the screening assay results and the sequence homology of the individual rabbit IgG clones, 30 candidates were selected for hit confirmation. 29 monoclonal antibodies were manufactured and the best performing clones in terms of affinity and potency were selected for the humanization and lead candidate generation. The criteria for the selection of clones were i) neutralization of human TNFα in L929 assay, ii) high affinity to human TNFα, iii) cross-reactivity to Cynomolgus and Rhesus monkey TNFα, and iv) sequence diversity. One clone (17-22-B03) has been selected for humanization—one of the best ranking IgGs in terms of potency to neutralize human TNFα in the L929 assay. With respect to binding strength, a high affinity is desired since a certain loss of affinity needs to be anticipated as a result of humanization and reformatting into the scFv format.

The data for IgG clone No. 17-22-B03 are summarized in Table 4.

TABLE 4

In vitro binding and activity properties of purified monoclonal antibody (17-22-B03)

| Affinity to human TNF | | | Affinity to cyno TNF | | | Affinity to rhesus TNF | | |
|---|---|---|---|---|---|---|---|---|
| $k_a$ (M$^{-1}$s$^{-1}$) | $K_d$ (s$^{-1}$) | KD(M) | $k_a$ (M$^{-1}$s$^{-1}$) | $K_d$ (s$^{-1}$) | KD(M) | $k_a$ (M$^{-1}$s$^{-1}$) | $K_d$ (s$^{-1}$) | KD(M) |
| 5.9E+06 | 9.3E−05 | 1.6E−11 | 8.9E+06 | <1E−06 | 1.12E−13 | 4.0E+06 | 1.6E−04 | 4.1E−11 |

| Potency in L929 assay rel. IC$_{50}$* | Blocking of TNF-TNFRI interaction rel. IC$_{50}$* | Blocking of TNF-TNFRII interaction rel. IC$_{50}$* |
|---|---|---|
| 22.58 | 5.1E−01 | 1.4E+00 |

*IC$_{50,\ Infliximab}$/IC$_{50,\ Test\ Sample}$ 1.2 Generation and Selection of Humanized scFv Fragments The sequences encoding the complementarity determining regions (CDRs) were transferred in silico by CDR-loop grafting onto a human variable domain scaffold sequence as described in WO 2014/206561. In addition a second construct was generated per rabbit clone, which transferred additional amino acids from the donor sequence at positions with structural relevance for the immunoglobulin domains and CDR positioning. An artificial gene (with an optimized codon usage for bacterial expression) encoding the respective humanized single-chain antibody Fv (scFv) was synthesized (from the corresponding variable light and heavy chains). The polypeptide was then produced and subsequently characterized using similar assays as described during the hit confirmation.

1.2.1 Humanization and Manufacture of Humanized scFv (APIs)

The humanization of the selected clone comprised the transfer of the rabbit CDRs onto a scFv acceptor framework of the Vκ1/VH3 type as described in WO 2014/206561. In this process, which is schematically shown in FIG. 1, the amino acid sequence of the six CDR regions was identified on the donor sequence (rabbit mAb) and grafted into the acceptor scaffold sequence, resulting in the constructs termed "CDR graft".

In addition, a second graft was designed, which included additional amino acids modifications from the rabbit donor on the positions L15, L22, L48, L57, L74, L87, L88, L90, L92, L95, L97, L99 and H24, H25, H56, H82, H84, H89, H108 (AHo numbering), which have been described to potentially influence CDR positioning and thus antigen binding (Borras et al., 2010, JBC 285:9054-9066). These humanized construct is termed "structural (STR) graft". In case the comparison of the characterization data for these two initial constructs revealed a significant advantage of the STR construct additional variants were designed that combined the CDR grafted VL with STR grafted VH. This combination has been proven to be often sufficient to retain the activity of the STR graft (Borras et al. JBC. 2010; 285:9054-9066) and would generally be preferred as fewer non-human alterations in the human acceptor scaffold reduce the risk for impaired stability and also the potential for immunogenicity.

Once the in-silico construct design described in the previous section was completed the corresponding genes were synthesized and bacterial expression vectors were constructed. The sequence of the expression constructs was confirmed on the level of the DNA and the constructs were manufactured according to generic expression and purification protocols.

The heterologous expression of the proteins was performed in *E. coli* as insoluble inclusion bodies. The expression culture was inoculated with an exponentially growing starting culture. The cultivation was performed in shake flasks in an orbital shaker using commercially available rich media. The cells were grown to a defined OD$_{600}$ of 2 and induced by overnight expression with 1 mM Isopropyl β-D-1-thiogalactopyranoside (IPTG). At the end of fermentation the cells were harvested by centrifugation and homogenized by sonication. At this point the expression level of the different constructs was determined by SDS-PAGE analysis of the cell lysate. The inclusion bodies were isolated from the homogenized cell pellet by a centrifugation protocol that included several washing steps to remove cell debris and other host cell impurities. The purified inclusion bodies were solubilized in a denaturing buffer (100 mM Tris/HCl pH 8.0, 6 M Gdn-HCl, 2 mM EDTA) and the scFvs were refolded by a scalable refolding protocol that generated milligram amounts of natively folded, monomeric scFv. A standardized protocol was employed to purify the scFvs, which included the following steps. The product after refolding was captured by an affinity chromatography employing Capto L agarose (GE Healthcare) to yield the purified scFvs. Lead candidates that met the affinity and potency criteria in initial testing were further purified by a polishing size-exclusion chromatography using a HiLoad Superdex75 column (GE Healthcare). Subsequent to the purification protocol the proteins were formulated in a buffered saline solution and characterized by the various biophysical, protein interaction and biological methods, as described in the following. The producibility of the different constructs was compared by determining the final yield of purified protein for the batch and normalizing this value to 1 L of refolding volume.

1.2.2 Biophysical Characterization of Humanized scFv

The biophysical characterization of the scFv with respect to stability and producibility were compiled in Table 5. The producibility and stability of the scFv construct was characterized by the different reporting points as discussed in the subsequent sections.

The scFv was investigated as to certain criteria, as explained in the following.

The producibility criterion shall ensure that the selected scFv entity can be expressed, refolded and purified in sufficient amounts to support later development of the lead molecule. The defined criteria were the expression yield of scFv per liter of fermentation broth, as assessed by SDS-PAGE, and the purification yield achieved in the generic lab-scale process, as assessed by measurement of the amount of purified protein by UV spectrometry, calculated back to 1 liter of refolding solution.

The criteria for stability were intended to assess the aggregation propensity during the manufacturing process of the molecules and their structural integrity during storage and further handling. The monomer content determined by SE-HPLC allows assessing the colloidal stability of molecules during the purification process (2.2.3). In a subsequent stability study the monomer content was tested over a duration of 4 weeks at 1 and 10 mg/mL and storage at 4, −20 and <−65° C. In addition, the colloidal stability of the proteins was tested after 5 freezing and thawing cycles. As an additional stability indicating parameter, the midpoint of thermal unfolding was determined by differential scanning fluorimetry (DSF) (2.2.4) to provide a read-out for the conformational stability of the lead candidates.

1.2.2.1 Producibility Assessment

The lead candidate scFv molecules were expressed by shake flask fermentation in batch mode and purified by a generic lab-scale process to yield the protein samples for further characterization. During this process some key performance parameters were monitored to compare the candidate molecules and to identify potentially difficult to develop constructs.

The expression titer was determined on the level of the crude E. coli lysate after the harvest of the cells by centrifugation. During the harvest a small loss of cells is anticipated, however, this factor was chosen to be neglected for the calculation of the expression yield in favor of a more conservative estimation of the productivity. For the quantification of the scFv product in the lysate coomassie stained reducing SDS-PAGE (2.2.1) was chosen due to the high specificity of the method that allows discriminating the product from the host cell proteins in the sample.

A second criterion to assess the producibility is the purification yield of scFv calculated per liter of refolding solution. This parameter addresses the potential bottleneck in the anticipated manufacturing process that includes a protein refolding step. Since the efficiency of the refolding procedure has proven to be limiting in comparable manufacturing processes it has been decided to compare the performance of the different constructs with respect to the producibility normalized to a defined refolding volume. For the calculation of the yield the final protein sample from each batch was quantified by UV absorbance (2.2.2) and divided by the actual refolding volume of the respective purification (Table 6).

TABLE 6

Summary of producibility data for three humanized scFvs. The expression titer was determined by quantitative SDS-PAGE on lysates of end-of-production cells. The batch yield was determined by UV absorbance measurement of the final purification pool. The purification yield is calculated as the purified scFv per liter of refolding volume.

| | Producibility | | | |
|---|---|---|---|---|
| Construct ID | Expression titer [g/L] | Batch yield [mg] | Refolding volume [L] | Purification yield [mg/mL] |
| 17-22-B03-sc02 | 0.28 | 10.7 | 0.45 | 23.7 |
| 17-22-B03-sc08 | 0.47 | 21.7 | 0.49 | 44.3 |
| 17-22-B03-sc12 | 0.38 | 23.2 | 0.40 | 57.9 |

1.2.2.2 Stability Assessment

The assessment of the conformational stability, monodispersity and structural integrity of the scFv constructs is an integral component for the ranking of the different molecules with respect to the developability. A prerequisite for the meaningful comparison of the different constructs is the preparation of purified molecules of similar quality. The criterion "monomer purity" determined by SE-HPLC is intended to ensure compatible quality of the different test substances. In addition to the SE-HPLC analysis, SDS-PAGE for the determination of protein purity and identity was performed to confirm comparable quality of the tested preparations.

Figure 2:
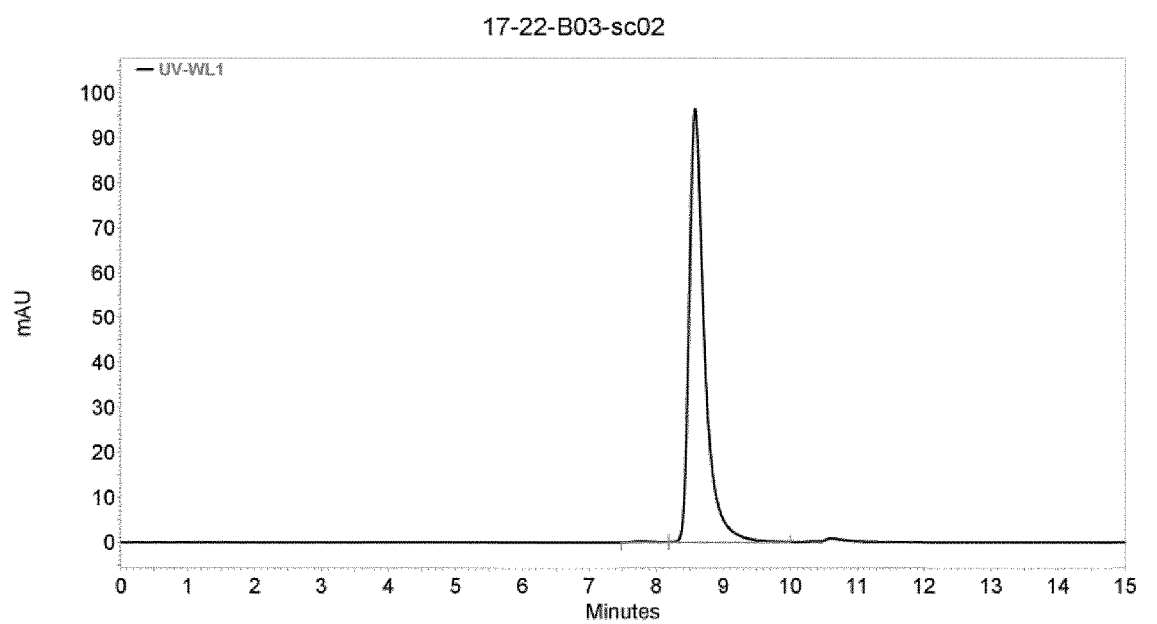
FIG. 2: SE-HPLC chromatograms of purified humanized scFv preparations of scFv. The scFv monomer elutes at retention times between 8.4 and 9.5 minutes, while buffer components elute at >10 min. All peaks from the dead volume of the column up to the respective scFv monomer were integrated as aggregates/oligomers and used for the calculation of the relative peak area.
Figure 2:
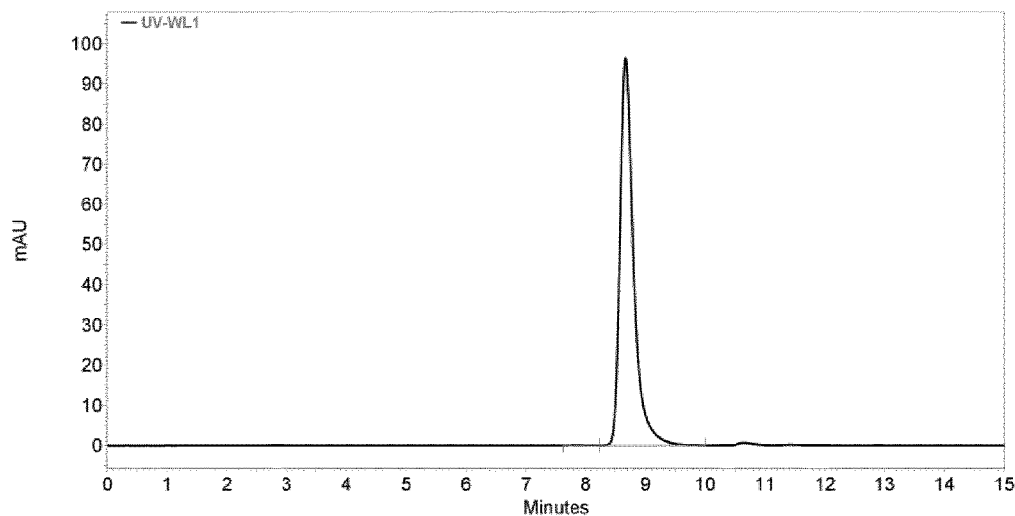
Figure 2:
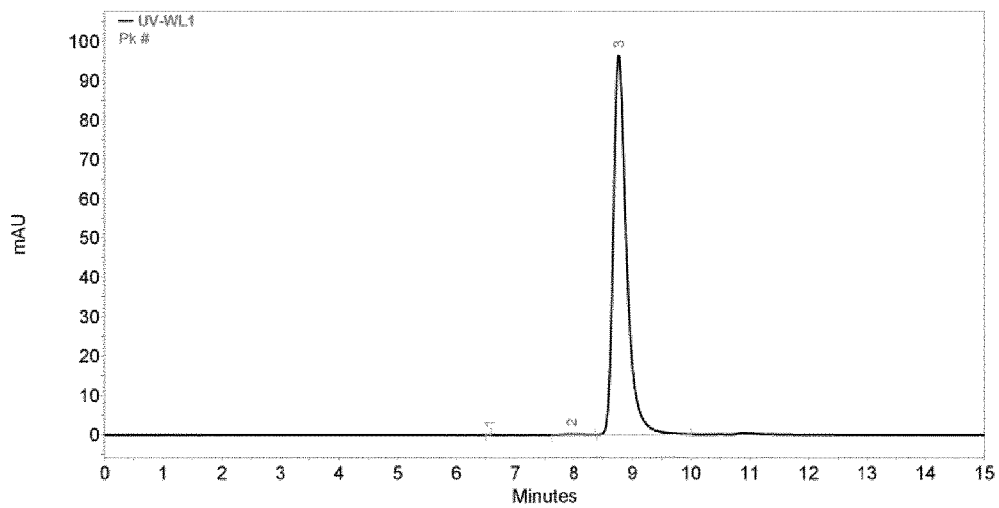

The SE-HPLC results of the three scFvs reveal that all preparations could be purified to a monomer content of at least 99% (FIG. 2).

Figure 3:
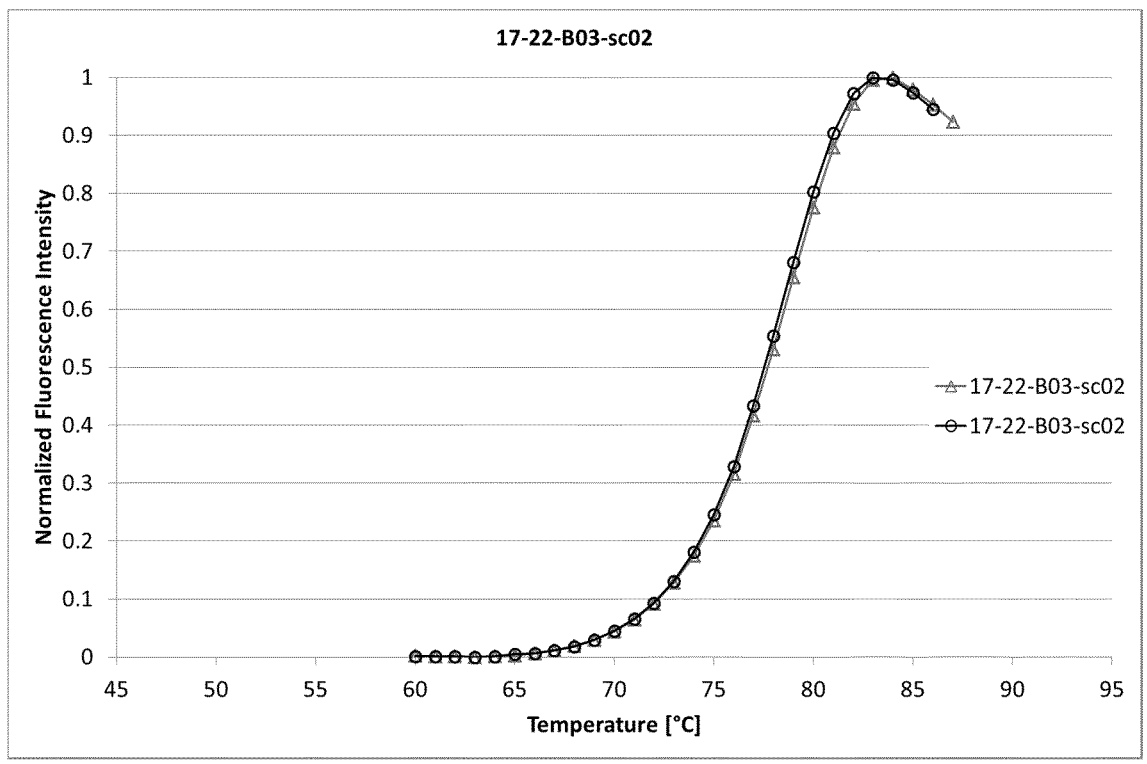
FIG. 3: Thermal unfolding curves from DSF measurements of three scFv constructs. For each construct duplicate measurements are shown. The resulting Tm values have been determined by fitting the data to a Boltzmann equation to obtain the midpoint of transition.
Figure 3:
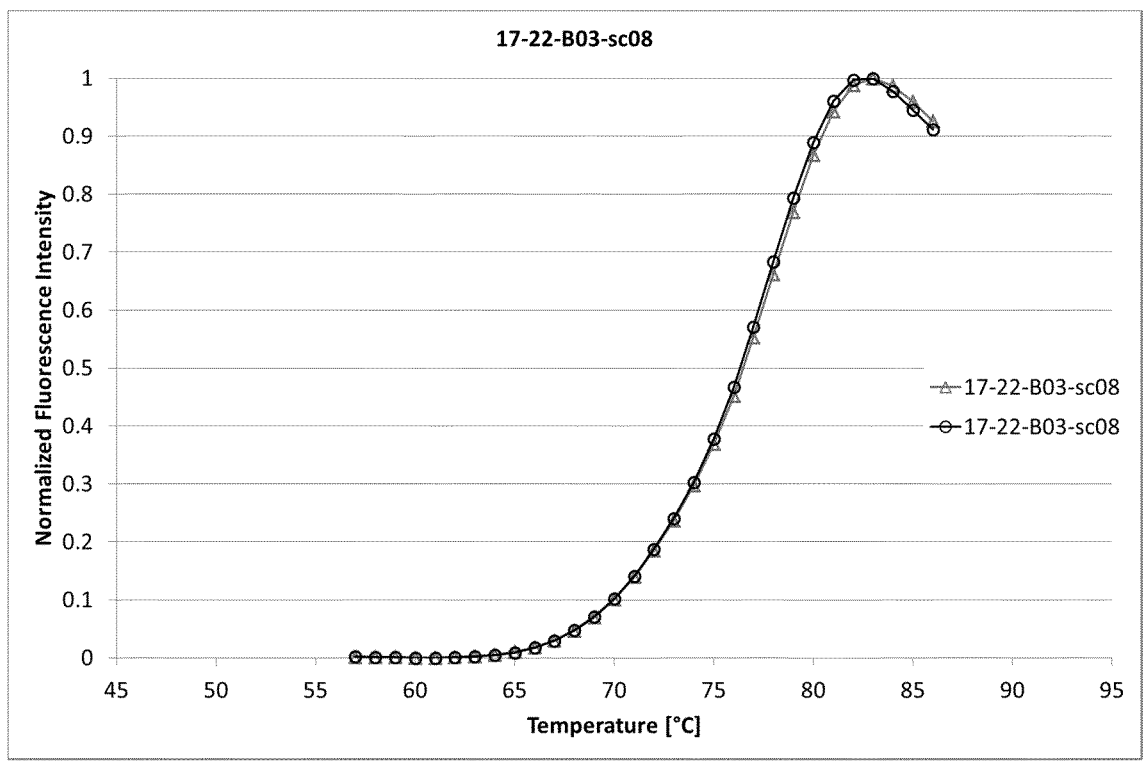
Figure 3:
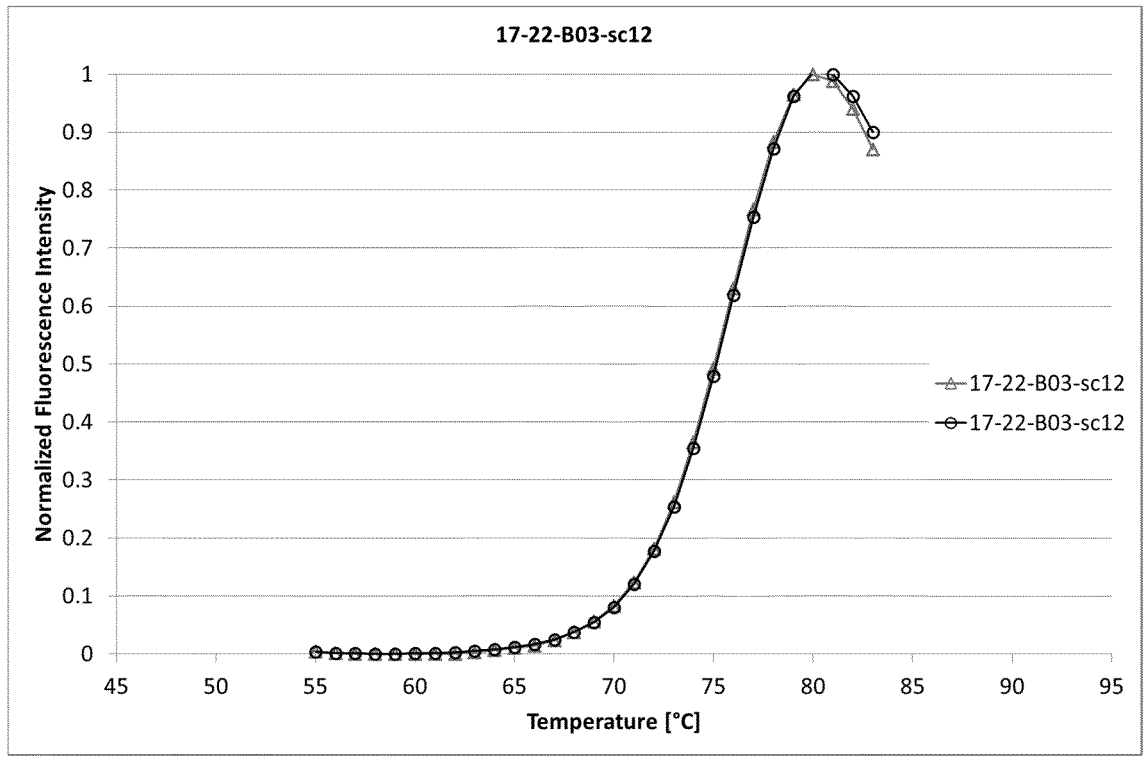

The thermal unfolding behavior of the lead candidates was tested by differential scanning fluorimetry (DSF) to allow ranking of the molecules with respect to their expected conformational stability. A normalized plot of the fluorescence raw data is shown in FIG. 3, which depicts duplicate measurements of each sample. A cooperative unfolding behavior was observed. The three molecules 17-22-B03-sc02, 17-22-B03-sc08 and 17-22-B03-sc12 showed a $T_m$ of 77.5, 76.2 and 74.9° C., respectively.

TABLE 5

Summary of the biophysical characterization data for the humanized scFvs.

| | | | Stability | | | | Producibility | | |
|---|---|---|---|---|---|---|---|---|---|
| clone ID | Construct | Tm [° C.] | Storage [Δ%] −65° C. | −20° C. | 4° C. | Freeze/thaw [Δ%] | Purity [%] | Expression [g/L] | Purification yield [mg/L] |
| 17-22-B03-sc02 | 17-22-B03 STR | 77.5 | 0.0 | 0.0 | 0.3 | 0.0 | 99.7 | 0.28 | 23.7 |
| 17-22-B03-sc08 | CDR/STR | 76.2 | 0.0 | 0.1 | 0.5 | 0.0 | 99.9 | 0.47 | 44.3 |
| 17-22-B03-sc12 | CDR(C90S)/STR | 74.9 | 0.1 | 0.1 | 3.7 | 0.1 | 99.8 | 0.38 | 57.9 |

Figure 4:
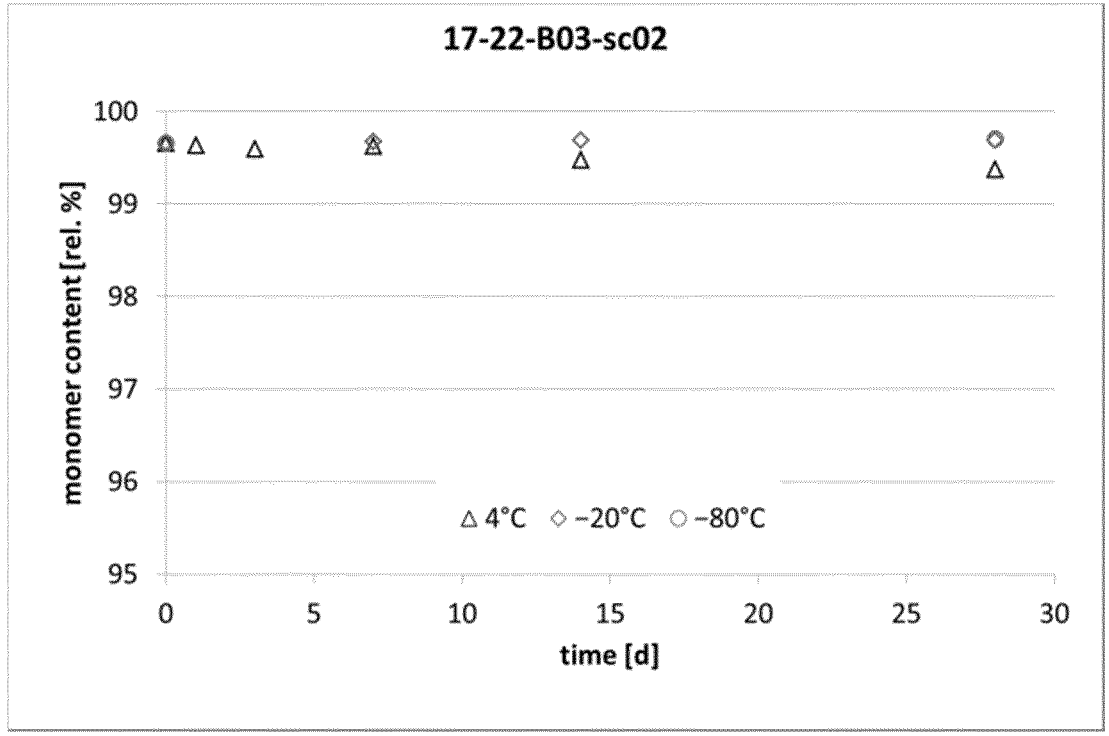
FIG. 4: Time-course of the monomer content of the three scFv constructs during storage. The monomer content as determined by SE-HPLC has been plotted for the storage temperatures 4, −20 and <−65° C. for the duration of 4 weeks.
Figure 4:
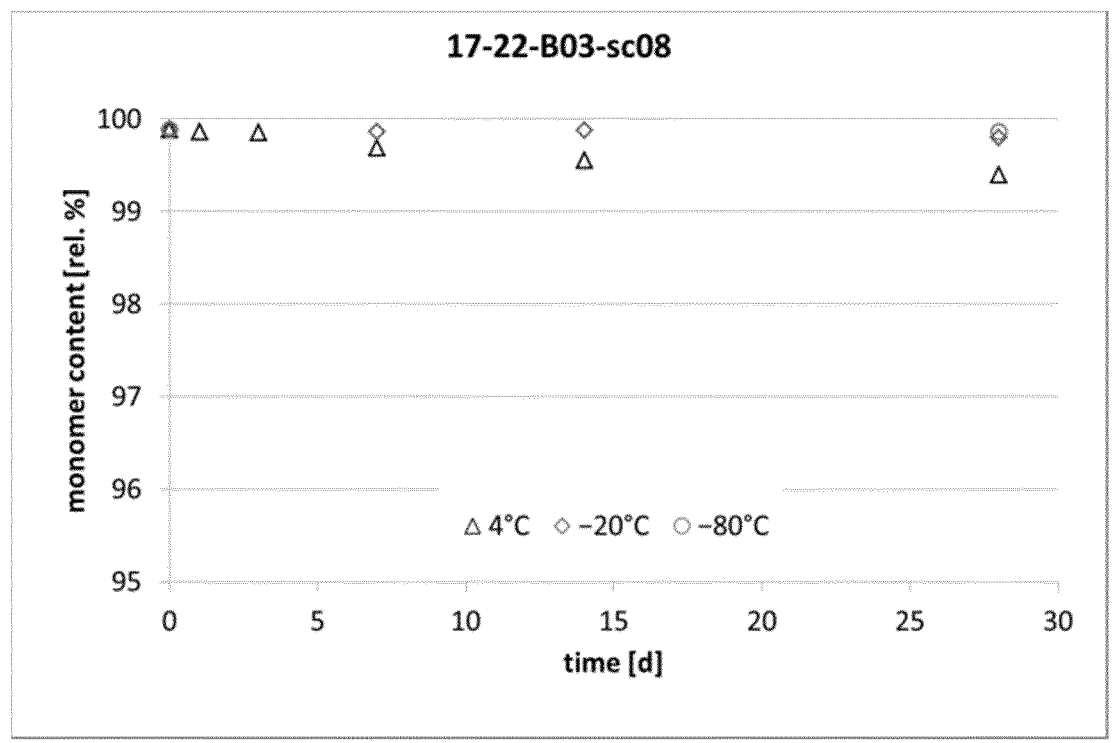
Figure 4:
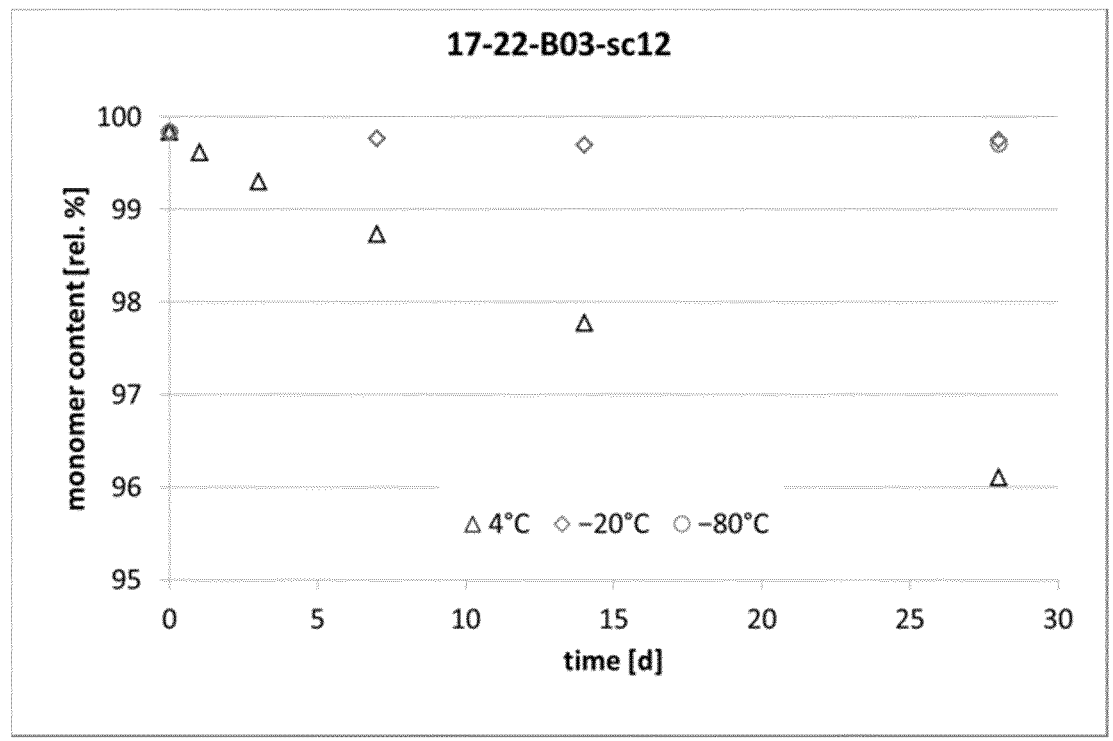
Figure 5:
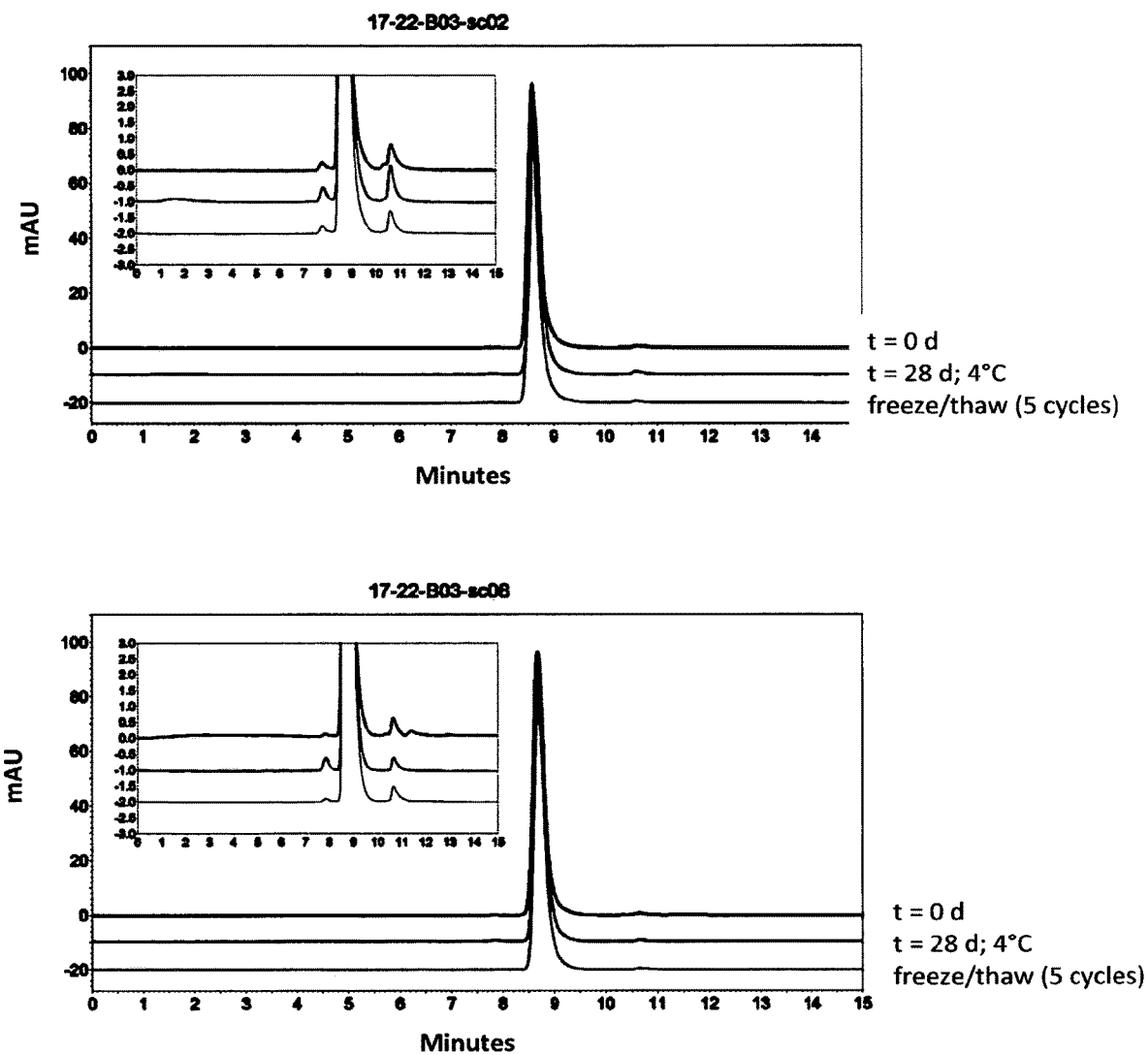
FIG. 5: Overlay of SE-HPLC chromatograms for three scFv molecules. For each scFv, the sample (10 mg/mL) at d0 and after storage for 4 weeks at 4° C. is shown. In addition, the chromatogram of the sample after 5 cycles of freezing and thawing is shown. The inserted panel shows an approx. 15-fold zoom of the y-axis for each molecule to visualize also minuscule changes in oligomer content.
Figure 5:
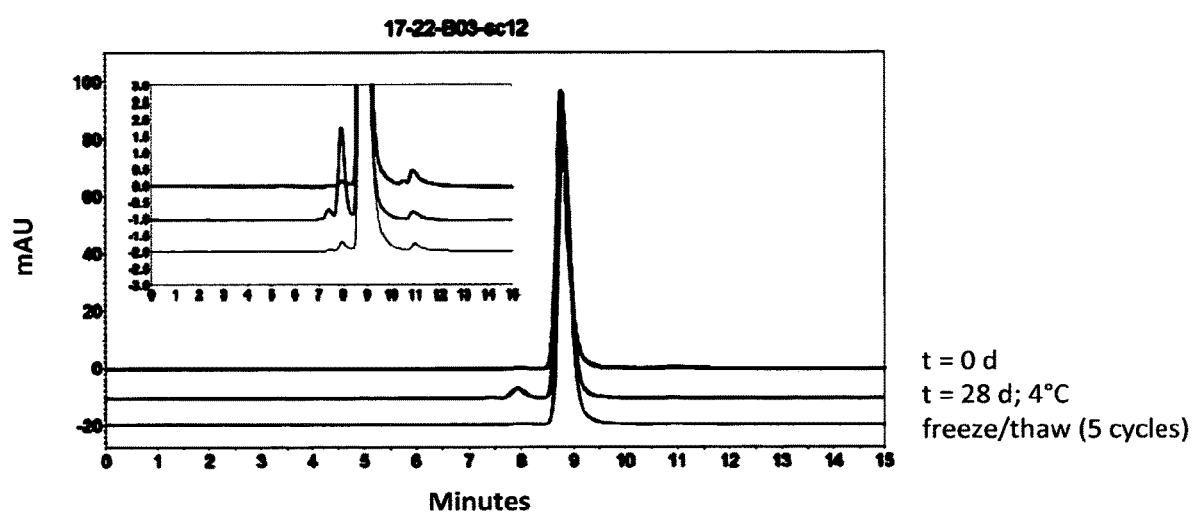
Figure 6:
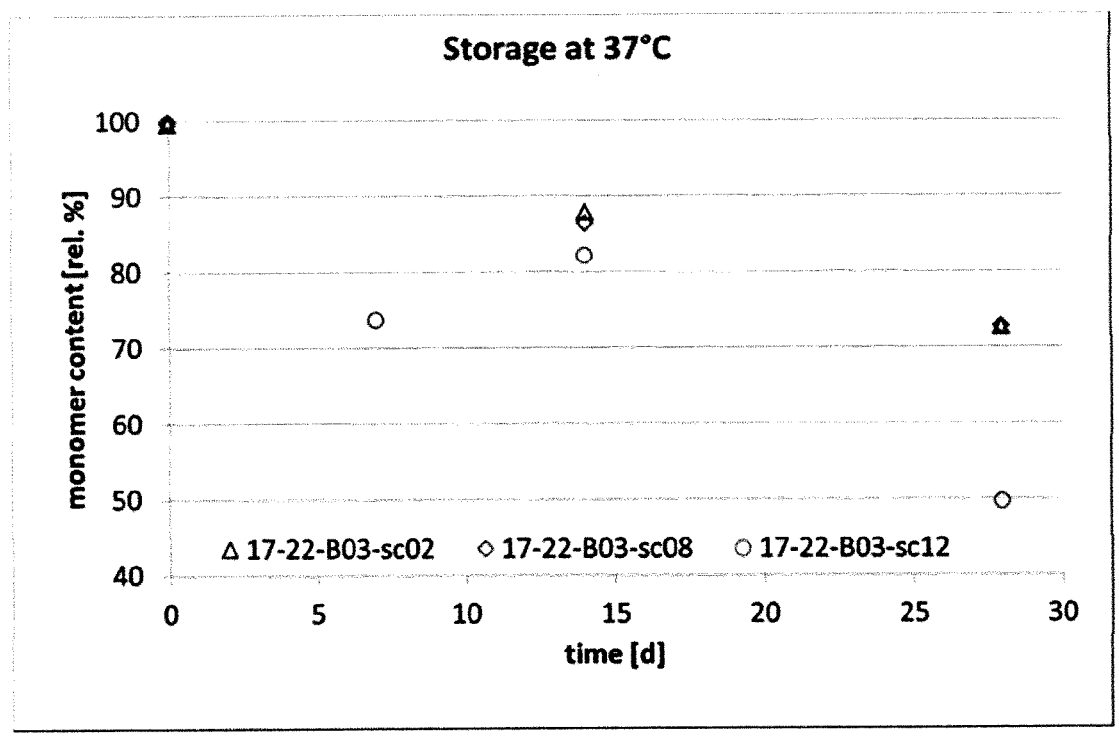
FIG. 6: Time-course of the monomer content of the humanized scFvs during storage. The monomer content as determined by SE-HPLC has been plotted for the 10 mg/mL samples at a storage temperature of 37° C. for the duration of 4 weeks.

In a second arm of the stability assessment the monodispersity of the molecules was monitored over the duration of 4 weeks at different temperatures. The results for the stability study and the resulting monomer contents are shown in FIG. 4. All three molecules (17-22-B03-sc02, 17-22-B03-sc08 and 17-22-B03-sc12) start at a monomer content exceeding the minimum of 95% monomer and lose less than 5% of monomer with respect to the respective starting value at a concentration of 10 mg/mL. In the frozen state at −20° C. and <−65° C. the samples only showed minimal differences over time. At the most stringent condition (4° C.) the molecule 17-22-B03-sc08 lost as little as 0.5% of monomer during the 4 weeks. In addition a stress stability study was conducted at a temperature of 37° C. and a scFv concentration of 10 mg/mL for up to 4 weeks. At this condition a more stringent discrimination of the propensity for aggregation of the different constructs is expected. The resulting data summarized in FIG. 6 revealed for 17-22-B03-sc02 and 17-22-B03-sc08 a monomer loss of 28% after 28 days. Both scFv demonstrated good monomer stability at stress conditions. Chromatograms of the stability study at 4° C. are provided in FIG. 5, where the sample at day 0 and after 28 days at 4° C. is shown. In this chromatogram overlay also the results of the freeze/thaw stability is shown. For this part of the study the samples were repeatedly frozen and thawed for a total of 5 cycles. The resulting quantification of the monomer content by analytical SE-HPLC did not reveal any changes in the two samples (Table 5).

A SDS-PAGE analysis was performed for the two scFvs to generate supportive data for the quantification by UV absorbance, confirming the purity of the sample preparation and thereby conferring specificity for the content quantification. In another aspect of this analysis the SDS-PAGE results revealed the absence of protein degradation during the stability study (28 days at 4° C. and a concentration of 10 mg/mL compared to sample from day 0 stored at <−65° C.), which is an important characteristic from a developability perspective.

It is important to note that the different studies performed within the scope of this assessment address distinct mechanistic aspects of protein stability. The determination of the thermal unfolding temperature of a protein will give complementary results to the measurement of the monodispersity by SE-HPLC upon storage at elevated temperature. While both methods are designed to give an estimation of the potential product shelf live and stability the mechanisms addressed are profoundly different. The midpoint of transition (Tm) assessed by thermal unfolding is a qualitative measure for protein domain stability (does not allow for thermodynamic determination of AG). Highly stable protein domains (high Tm) are less likely to spontaneously unfold at ambient temperature and thus less prone to irreversible aggregation/precipitation driven by unfolded domain interactions. High domain stability indicates dense packaging of amino acid residues, which also correlates with resistance towards protease cleavage. The SE-HPLC assessment on the other hand quantitatively determines the content of the monomeric fraction as well as of soluble oligomers/aggregates. Such soluble oligomers are oftentimes reversible and relatively loose associations driven by electrostatic or hydrophobic interactions between correctly folded proteins. There is some correlation between Tm as assessed by thermal unfolding and the propensity for oligomer/aggregate formation as assessed by SE-HPLC particularly for proteins with "border line" stability. Beyond a certain threshold Tm of approximately 60° C. antibody variable domains are generally sufficiently stable to be resistant toward aggregation/precipitation and proteolytic degradation due to partial domain unfolding at ambient temperature. Oligomerization driven by hydrophobic and/or electrostatic interactions of surface residues may, however, still occur. Importantly, in an accelerated (stress) stability study at elevated temperature (e.g. 37° C.) the various mechanisms of oligomer formation and precipitation may occur simultaneously.

1.2.3 Characterization of In Vitro Binding and Activity of Humanized scFvs

In the following the humanized scFvs were characterized in vitro for their target binding properties and potencies. Binding kinetics (ka, kd and KD) to human TNFα and potency to neutralize TNFα-induced apoptosis of L929 fibroblasts was analyzed. Additionally, the potency to inhibit Cynomolgus monkey (*Macaca fascicularis*) and Rhesus monkey (*Macaca mulatta*) TNFα induced apoptosis as well as the potency to inhibit the interaction between human TNFα and TNFRI/TNFRII by ELISA and target selectivity for binding to TNFα over TNFβ was determined.

For the understanding of the results below it is important to note that both, the transfer of the rabbit CDRs onto a human variable domain scaffold as well as the change in the format from the full-size IgG to the scFv fragment may impact on pharmacological properties. For example, a certain loss of affinity is usually associated with humanization. Further, due to the smaller size of the scFv compared to the IgG the ability of a scFv to interfere with interaction partners through steric hindrance is largely reduced. Last but not least it shall be noted that due to its bivalent mode of binding to the homo-trimeric TNFα, the affinity of the parent IgG may have been reported too high (SPR artifact). Consequently, when comparing affinities between the parental bivalent rabbit IgG and the humanized monovalent scFv, the reported "loss in affinity" may be overestimated.

1.2.3.1 Affinity

Affinity of humanized scFvs to human TNFα was determined by SPR measurements (see also 2.1.1). Affinity was determined using 2-fold serial dilutions of the respective scFvs. The scFvs were derived from a rabbit monoclonal antibody. Two scFv variants were generated, named "CDR" (CDR) and "structural graft" (STR). To assess the relative contribution of framework substitutions in the light and the heavy chain and to possibly reduce the number of rabbit amino acid residues introduced in the human framework, domain shuffling experiments were performed. Therefore, scFv constructs containing a CDR grafted light chain and a structural grafted heavy chain (CDR/STR) were generated for clone 17-22-B03.

The top ranking scFvs 17-22-B03-sc02 (STR), 17-22-B03-sc08 (CDR/STR) and 17-22-B03-sc12 (CDR(C90S)/STR) bound with affinities of $5.2 \times 10^{-11}$, $6.1 \times 10^{-11}$ and $4.8 \times 10^{-11}$ M, respectively. There was almost no variation in affinity between the three "structural graft" variants (see Table 7).

1.2.3.2 Potency

Figure 7:
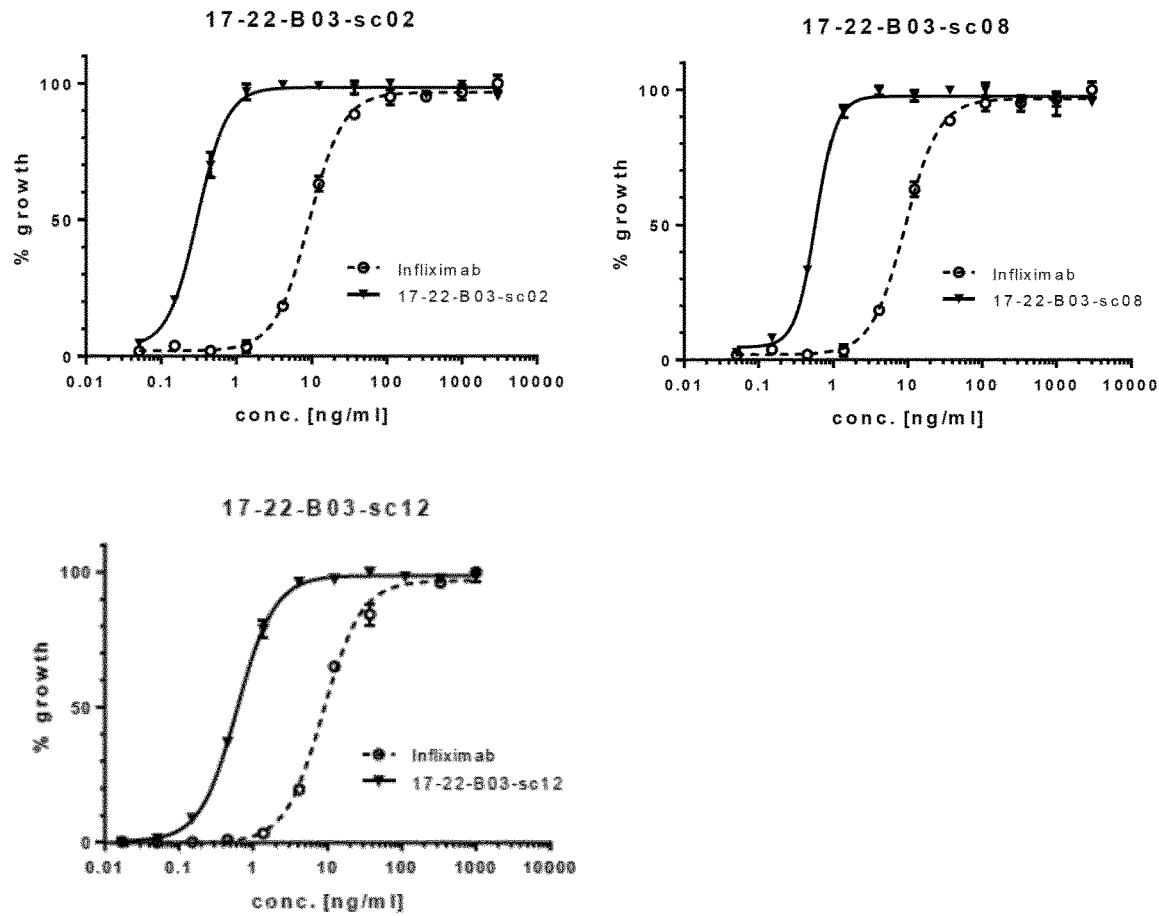
FIG. 7: Potency to neutralize human TNFα in the L929 assay of three scFvs. Dose-response curves for the scFvs and the reference antibody Infliximab are shown for each experiment. The highest scFv and infliximab concentrations as well as negative controls were set to 100% and 0% of growth.

The ability of the humanized scFvs to neutralize human TNFα was analyzed using the L929 assay (see also 2.1.2). The potency ($IC_{50}$ and $IC_{90}$) to neutralize TNFα induced apoptosis was analyzed for 17-22-B03 derived scFvs and compared to the potency of the reference antibody infliximab to allow for direct comparison of $IC_{50}$ and $IC_{90}$ values from different assay plates. Relative $IC_{50}$ and $IC_{90}$ values were calculated in mass units (ng/mL) of infliximab and the scFvs. Potency analysis was performed several times on different days with different lots of antibody fragments. FIG. 7 shows representative dose-response curves from one experiment for each of the two scFvs. Mean values of replicate measurements are shown in Table 7 (standard deviations are summarized in the legend of the table).

The humanized scFvs inhibited TNFα induced apoptosis with lower $IC_{50}$ and $IC_{90}$ values than infliximab (see Table 7). Consistent with SPR results, the domain shuffled variant 17-22-B03-sc08 (CDR/STR) exhibited equal potency when compared to the structural graft 17-22-B03-sc02 (STR). The scFvs 17-22-B03-sc02, 17-22-B03-sc08 and 17-22-B03-sc12 showed excellent TNFα-neutralizing activities, with $IC_{50}$ values of 23.7-, 26.0- and 13.4-fold better than infliximab, respectively. $IC_{90}$ value of 17-22-B03-sc02, 17-22-B03-sc08 and 17-22-B03-sc12 were 29.4-, 26.6- and 11.7-fold better than for infliximab, respectively. As observed for the parental rabbit monoclonal antibodies there was no clear correlation between affinity and potency of antibodies (correlation not shown). Additionally, results from the neutralization assays suggest that a certain threshold affinity needs to be achieved for efficient inhibition of TNFα signaling. For example, scFvs 16-14-D08-sc01 (CDR), 16-15-009-sc01 (CDR), 16-24-H07-sc01 (CDR) and 17-20-G01-sc01 (CDR), all binding to TNFα with affinities above 1 nM, show poor potential to neutralize TNFα (not shown).

1.2.3.3 Species Cross-Reactivity (Cynomolgus and Rhesus Monkey TNFα)

Species cross-reactivity for the top ranking scFvs was determined by two methods: 1) potency to neutralize Cynomolgus monkey and Rhesus monkey TNFα in the L929 assay and 2) affinity to Cynomolgus monkey and Rhesus monkey TNFα by SPR. The potency to neutralize TNFα from the different species was determined by the L929 assay similarly as described above for human TNFα using Cynomolgus monkey and Rhesus monkey TNFα, respectively (see also 2.1.2). TNFα from both species showed very similar potency to induce L929 apoptosis (data not shown). Therefore, same concentrations of human and monkey TNFα were used for species cross-reactivity testing. Additionally, binding kinetics (by SPR) to Cynomolgus monkey and Rhesus monkey TNFα were determined using a similar assay as for human TNFα (see also 2.1.1).

Figure 8:
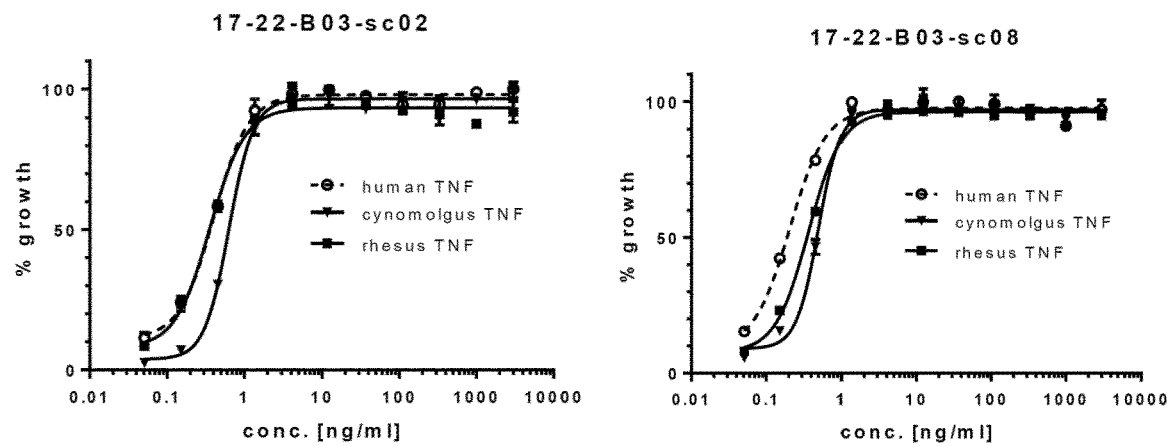
FIG. 8: Potency of two scFvs to neutralize non-human primate and human TNFα in the L929 assay. Dose-response curves for neutralization of human, Cynomolgus monkey and Rhesus monkey TNFα are shown. The highest scFv concentration and negative controls were set to 100% and 0% of growth.

All scFvs derived from the clone 17-22-B03 showed cross-reactivity to Cynomolgus monkey and Rhesus monkey TNFα (see Table 7). The affinities were similar, namely $5.0 \times 10^{-11}$ and $1.5 \times 10^{-10}$ M for Cynomolgus monkey and Rhesus monkey, respectively in the case of 17-22-B03-sc02. The difference in affinity between human and Rhesus monkey TNFα was about 3-fold, while the affinity to Cynomolgus monkey TNFα was comparable to human TNFα. (see Table 7 and FIG. 8). To summarize, the scFvs derived from clone 17-22-B03 showed species cross-reactivity to Cynomolgus and Rhesus TNFα.

1.2.3.4 Blocking of the Human TNFα-TNFRI/II Interaction

In addition to the L929 assay, the potency of each humanized scFv to inhibit the interaction between human TNFα and TNFRI/II was assessed by ELISA (see 2.1.3). Similarly to the L929 assay, individual $IC_{50}$ values on each plate were calibrated against the $IC_{50}$ of the reference molecule infliximab that was taken along on each plate and relative $IC_{50}$ and $IC_{90}$ values were calculated in mass units (ng/mL) of Infliximab and the scFvs.

Neutralization assays can distinguish potencies of target blocking antibodies only if they bind their target with an equilibrium binding constant (KD) that is higher than the target concentration used in the potency assay (KD>target concentration). For the L929 assay a TNFα concentration of 5 pM was used while in the TNFRI/II inhibition ELISAs a TNFα concentration of 960 pM was used. Therefore, theoretically, the L929 assay can differentiate potencies between scFvs with KD>5 pM, while the inhibition ELISA can only differentiate potencies between scFvs with KD>960 pM. Since all of the scFvs analyzed showed KDs below 960 pM, potencies between scFvs with different affinities (but similar mechanism of action) can be differentiated only in the L929 assay.

Figure 10:
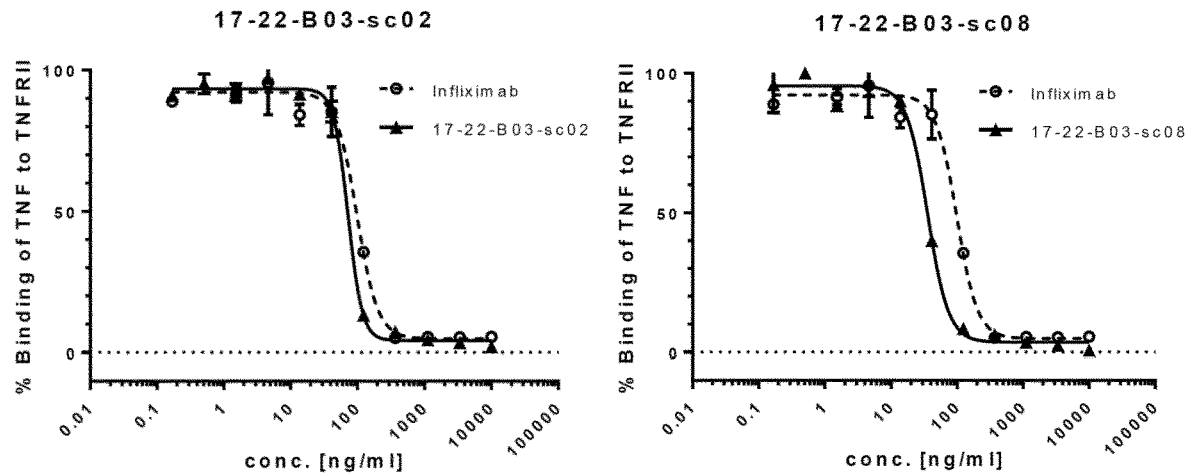
FIG. 10: Potency of two scFvs to block the TNFα-TNFRII interaction. Dose-response curves are shown. The highest scFv concentration and negative controls were set to 0% and 100% of binding of TNFα to TNFRII.
Figure 10:
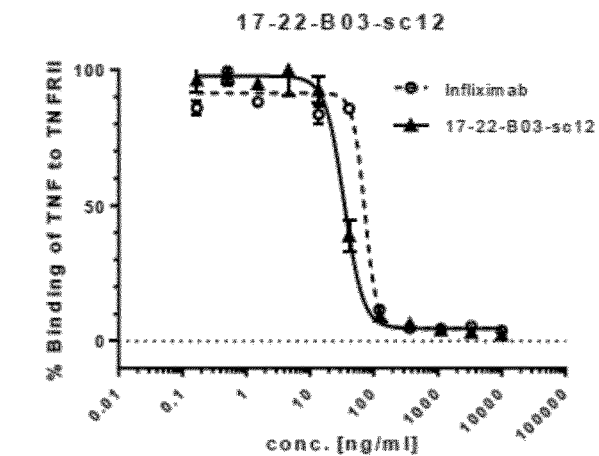

17-22-B03-sc02, 17-22-B03-sc08 and 17-22-B03-sc12 showed potencies for blocking of the TNFα-TNFRI interaction of 1.5-, 2.3- and 1.5-fold higher compared to infliximab, respectively, while the potency compared to infliximab in the L929 assay was significantly higher (23.7-, 26.0- and 13.4-fold). Inhibition of the TNFα-TNFRII interaction was in the similar range as for TNFα-TNFRI blocking. When comparing the relative $IC_{50}$ values for the parental rabbit IgG (see Table 4) with the relative $IC_{50}$ values for the humanized scFvs (Table 7) potencies of the scFvs are in general slightly higher compared to the parental IgG although affinities in general are in the same range for the parental rabbit IgG. Since potencies of antibodies and scFvs were compared in mass units, the number of valencies (TNFα binding sites) at each concentration is about 2.9-fold higher for the monovalent scFvs compared to the more than five-fold heavier but bivalent IgG. With very high-affinity binding scFvs, this results in more potent blocking of the TNFα and TNFRI/II interaction because the lack of avidity is no longer critical for activity. In contrast, with low-affinity monovalent domains the opposite has been published (Coppieters et al. Arthritis & Rheumatism 2006; 54:1856-1866). For the reasons mentioned above, results from the inhibition ELISA were not used for ranking of potencies between the different antibodies but primarily for comparison of the potential of antibodies to block the interaction with TNFRI versus TNFRII. The investigated scFvs blocked the interaction between both TNFα receptors with comparable potencies (Table 9, FIG. 9 and FIG. 10).

1.2.3.5 Target Specificity (Selectivity for Binding to TNFα Versus TNFβ)

Figure 11:
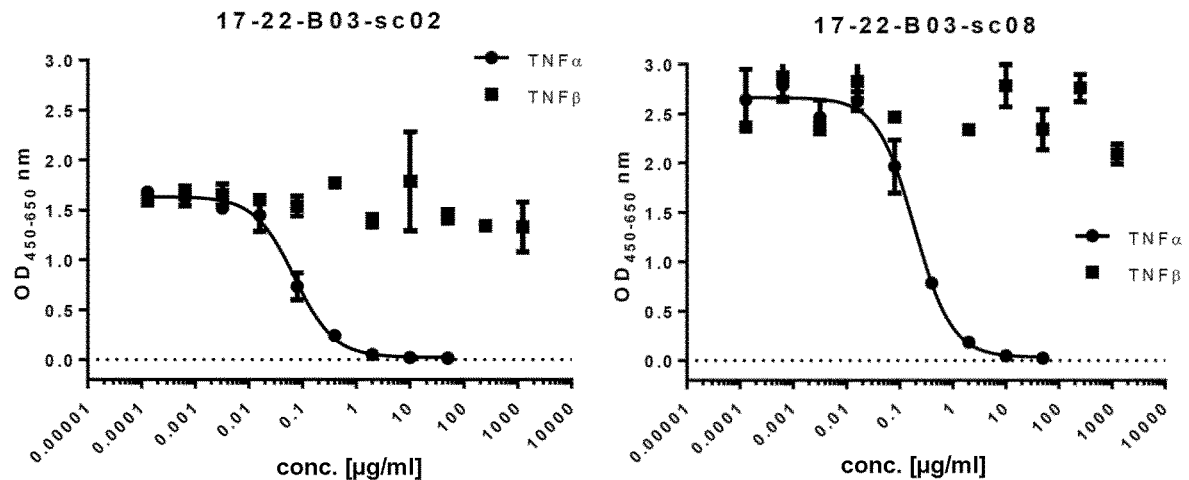
FIG. 11: Target specificity of an scFv. The potential to inhibit the interaction of biotinylated TNFα with the scFv by TNFα and TNFβ was analyzed by competition ELISA. Dose-dependent effects of TNFα and TNFβ are shown.

Specificity of the three scFvs (17-22-B03-5c02, 17-22-B03-sc08 and 17-22-B03-sc12) for TNFα over TNFβ was confirmed by assessment of the relative potential of TNFβ as compared to TNFα to half-maximally inhibit TNFα binding to each scFv and was measured in a competition ELISA (see also 2.1.4). The quality of recombinant human TNFβ has been analyzed 1) for purity by SDS-page and HPLC analysis, and 2) for biological activity in the mouse L929 cytotoxicity assay, by the manufacturer of the protein. As shown in FIG. 11, the interaction between each of the scFvs with biotinylated TNFα was blocked by unlabeled TNFα with $IC_{50}$ values ranging from 60 to 260 ng/mL, while TNFβ did not show any significant effect even at the highest concentration of TNFβ tested (1250 µg/mL). Hence, all of the scFvs analyzed bind specifically to TNFα but not to its closest homologue, TNFβ. TNFβ did not show any significant inhibition of TNFα binding to scFvs at the concentrations tested. Therefore, the TNFβ concentration required to half-maximally inhibit TNFα binding has to be significantly higher than the highest concentration of TNFβ used in the assay (1250 µg/mL). When comparing concentrations of TNFα and TNFβ required to half-maximally inhibit TNFα binding to the scFvs, the selectivity for binding to TNFα over TNFβ is significantly higher than approximately 5000 to 20'000 fold for all of the fragments tested (see also Table 7). Therefore, off-target binding of any of the scFvs appears highly unlikely.

The results of the experiments described above are summarized in tables 7 to 9.

TABLE 7

In vitro binding and activity properties of humanized scFvs.

| scFv | Design | Affintiy to human TNF | | | Affintiy to cyno TNF | | |
|---|---|---|---|---|---|---|---|
| | | $k_a$ (M$^{-1}$s$^{-1}$) | $K_d$ (s$^{-1}$) | KD (M) | $k_a$ (M$^{-1}$s$^{-1}$) | $K_d$ (s$^{-1}$) | KD (M) |
| 17-22-B03-sc02 | STR | 1.1E+06 | 5.9E−05 | 5.2E−11 | 1.2E+06 | 6.0E−05 | 5.0E−11 |
| 17-22-B03-sc08 | CDR/STR | 1.1E+06 | 6.8E−05 | 6.1E−11 | nd | nd | nd |
| 17-22-B03-sc12 | CDR(C90S)/STR | 8.3E+05 | 4.0E−05 | 4.8E−11 | 7.5E+05 | 5.2E−05 | 7.0E−11 |

| scFv | Design | Affintiy to rhesus TNF | | | Potency | |
|---|---|---|---|---|---|---|
| | | $k_a$ (M$^{-1}$s$^{-1}$) | $K_d$ (s$^{-1}$) | KD (M) | rel. IC$_{50}$* | rel. IC$_{90}$& |
| 17-22-B03-sc02 | STR | 7.1E+05 | 1.1E−04 | 1.5E−10 | 23.7 | 29.4 |
| 17-22-B03-sc08 | CDR/STR | nd | nd | nd | 26.0 | 26.6 |
| 17-22-B03-sc12 | CDR(C90S)/STR | 8.3E+05 | 2.0E−04 | 2.4E−10 | 13.4 | 11.7 |

| scFv | Design | Species-specificity IC$_{50}$ [ng/mL] | | | Target selectivity rel. IC$_{50}$ of TNFβ vs TNFα |
|---|---|---|---|---|---|
| | | human | cyno | rhesus | |
| 17-22-B03-sc02 | STR | 0.5 | 0.6 | 0.3 | >>10'000 |
| 17-22-B03-sc08 | CDR/STR | 0.4 | 0.5 | 0.4 | >>10'000 |
| 17-22-B03-sc12 | CDR(C90S)/STR | 0.6 | 0.8 | 0.9 | >>10'000 |

*IC$_{50, Infliximab}$ (ng/mL)/IC$_{50, scFv}$ (ng/mL)
&IC$_{90, Infliximab}$ (ng/mL)/IC$_{90, scFv}$ (ng/mL)
CDR: "CDR graft",
STR: "structural graft".
Potency analysis was performed several times on different days with different lots of antibody fragments with the following standard deviations: 17-22-B03-sc02 (n = 4): rel. IC$_{50}$ = 23.7 ± 9.8 and rel. IC$_{90}$ = 29.4 ± 9.5; 17-22-B03-sc08 (n = 3): rel. IC$_{50}$ = 26.0 ± 13.6 and rel. IC$_{90}$ = 26.6 ± 2.5.

TABLE 8

Specifications of humanized scFvs of the present invention.

| | Expression | Producibility | Stability | | |
|---|---|---|---|---|---|
| | Expression yield [g/L] | Refolding yield [mg/L] | Thermal unfolding [° C.] | Monomer loss after 4 w at 10 g/L at 4° C. (−65, −20) [Δ %] | Monomer loss after 5 freeze/thaw cycles [Δ %] |
| 17-22-B03-sc02 | 0.28 | 23.7 | 77.5 | 0.3 (0.0, 0.0) | 0.0 |
| 17-22-B03-sc08 | 0.47 | 44.3 | 76.2 | 0.5 (0.0, 0.1) | 0.0 |
| 17-22-B03-sc12 | 0.38 | 57.9 | 74.9 | 3.7 (0.1, 0.1) | 0.1 |

TABLE 9

Potency of scFvs to block the TNFα-TNFRI and TNFα-TNFRII interaction.

| scFv | Blocking of TNF-TNFRI interaction | | | | Blocking of TNF-TNFRII interaction | | | |
|---|---|---|---|---|---|---|---|---|
| | rel. IC$_{50}$* | rel. IC$_{90}$& | IC$_{50}$ [ng/mL] | IC$_{90}$ [ng/mL] | rel. IC$_{50}$* | rel. IC$_{90}$& | IC$_{50}$ [ng/mL] | IC$_{90}$ [ng/mL] |
| 17-22-B03-sc02 | 1.5 | 1.4 | 33.4 | 70.5 | 1.4 | 1.8 | 71.1 | 123.5 |
| 17-22-B03-sc08 | 2.3 | 2.5 | 21.2 | 39.2 | 2.8 | 2.7 | 35.3 | 80.1 |
| 17-22-B03-sc12 | 1.5 | nd | nd | nd | 2.1 | nd | nd | nd |

*IC$_{50, Infliximab}$ (ng/mL)/IC$_{50, scFv}$ (ng/mL)
&IC$_{90, Infliximab}$ (ng/mL)/IC$_{90, scFv}$ (ng/mL)

2. Methods
2.1 Lead Characterization Assays
2.1.1 Binding Kinetics and Species Cross-Reactivity by SPR Binding affinities of scFvs towards human TNFα were measured by surface plasmon resonance (SPR) using a MASS-1 SPR instrument (Sierra Sensors). Performance of the SPR assay was qualified by analysis of a reference antibody antigen interaction such as certolizumab-TNFα interaction. The pegylated Fab-fragment certolizumab was selected as reference due to its monovalent binding mode similar to that of scFvs. Using the same assay setup as for affinity measurements of the scFvs, a value of 9.94×10$^{-11}$ M was determined for the affinity of certolizumab to TNFα. This value is in good agreement with published K$_D$ values of 9.02±1.43×10$^{-11}$ M (BLA certolizumab; BLA number: 125160; submission date: Apr. 30, 2007).

For affinity measurements of scFvs human TNFα (Peprotech, Cat. No. 300-01) was immobilized on a sensor chip (SPR-2 Affinity Sensor, Amine, Sierra Sensors) by amine-coupling to reach an immobilization level of 50 to 100 RUs (immobilization levels achieved during SPR analysis were between 40 to 120 RUs). In a first step, affinity screening of scFvs was performed using only one scFv concentration (90 nM). In a second step, for the best performing scFvs, Single Injection Cycle Kinetics (SiCK) were measured from a single injection cycle by simultaneously injecting six analyte samples at different concentrations into each of the eight parallel channels in the MASS-1 system. For affinity screenings, humanized scFvs were injected into the flow cells at a concentration of 90 nM for three minutes and dissociation was monitored for 12 minutes. For the subsequent more precise affinity determinations, two-fold serial dilutions of scFv ranging from 45 to 1.4 nM were injected into the flow cells for three minutes and dissociation of the protein from TNFα immobilized on the sensor chip was allowed to proceed for 12 minutes. The apparent dissociation ($k_d$) and association ($k_a$) rate constants and the apparent dissociation equilibrium constant ($K_D$) were calculated with the MASS-1 analysis software (Analyzer, Sierra Sensors) using one-to-one Langmuir binding model and quality of the fits was monitored based on Chi$^2$, which is a measure for the quality of the curve fitting. The smaller the value for the Chi$^2$ the more accurate is the fitting to the one-to-one Langmuir binding model. For affinity screenings, results were deemed valid if the Chi$^2$ was below 10 for the concentration analyzed. In cases where several scFv concentrations were analyzed, results were deemed valid if the average Chi$^2$ over all the concentrations tested was below 10. Acceptance criteria were met for all scFvs tested.

Species cross-reactivity to Cynomolgus monkey (Sino Biological, Cat. No. 90018-CNAE) and Rhesus monkey (R&D Systems, Cat. No. 1070-RM-025/CF) TNFα (Peprotech, Cat. No. 315-01A) was measured using the same assay setup and applying the same quality measures as described above for human TNFα. For Cynomolgus and Rhesus monkey TNFα immobilization levels ranging from 50 to 180 RUs and from 90 to 250 RUs, respectively, were achieved. The scFvs were analyzed using two-fold serial dilutions with concentrations ranging from 45 to 1.4 nM. The average Chi$^2$ values were below 10 for all of the scFvs tested.

2.1.2 TNF-Induced Apoptosis in L929 Fibroblasts (Neutralization of Human, Non-Human Primate and TNFα by scFvs)

The ability of scFvs to neutralize the biological activity of recombinant human TNFα was assessed using mouse L929 fibroblasts (ATCC/LGC Standards, Cat. No. CCL-1). L929 cells were sensitized to TNF-induced apoptosis by addition of 1 μg/mL actinomycin D. Three-fold serial dilutions of anti-TNFα reference antibody or scFvs (3000-0.05 ng/mL) and 5 pM recombinant human TNFα (Peprotech, Cat. No. 300-01) were pre-incubated at room temperature for 1 hour. The used TNFα concentration (5 pM) induces submaximal L929 apoptosis (EC$_{90}$). After addition of the agonist/inhibitor mixtures the cells were incubated for 24 hours. Survival of the cells was determined by a colorimetric assay using the WST-8 (2-(2-methoxy-4-nitrophenyl)-3-(4-nitrophenyl)-5-(2,4-disulfophenyl)-2H-tetrazolium, monosodium salt) cell proliferation reagent (Sigma Aldrich, Cat. No. 96992). WST-8 is reduced by cellular dehydrogenases to an orange formazan product. The amount of formazan produced is directly proportional to the number of living cells. Data were analyzed using a four-parameter logistic curve fit using the Softmax Data Analysis Software (Molecular Devices), and the concentration of reference antibody or scFvs required to neutralize TNFα-induced apoptosis by 50% and 90% (IC$_{50}$ and IC$_{90}$) was calculated (see also FIG. 7). In order to render IC$_{50}$ and IC$_{90}$ values directly comparable between experiments that were performed on different days or on different assay plates, IC$_{50}$ and IC$_{90}$ values were calibrated against the reference antibody infliximab. To control precision of the response, the dose-response curves were analyzed in duplicate. Standard deviations and CVs were calculated for each measurement point (CV<20%).

Species cross-reactivity to Cynomolgus monkey (Sino Biological, Cat. No. 90018-CNAE) and Rhesus monkey (R&D Systems, Cat. No. 1070-RM-025/CF) TNFα was measured using the same assay setup and applying the same quality measures as described above for human TNFα. Similarly to the human counterpart, TNFα concentrations that induce submaximal L929 apoptosis (EC$_{90}$) were used for species cross-reactivity testing. TNFα from both species showed very similar potency to human TNFα to induce L929 mouse fibroblast apoptosis. Consequently the same concentration of TNFα (5 pM) was used for oth species tested. During species cross-reactivity testing CVs of most of the duplicate measurement points were below 10%.

2.1.3 TNFα Inhibition ELISA

The inhibitory effect of scFvs on ligand binding was assessed using an ELISA, a biochemical method solely reproducing the interaction between TNFα and TNFRI and TNFRII.

For the first inhibition ELISA, the extracellular domain of TNFRI fused to the Fc region of human IgG (R&D Systems, Cat. No. 372-RI) was coated on a 96-well Maxisorp ELISA at a concentration of 0.5 μg/mL. For the second inhibition ELISA, the extracellular domain of TNFRII fused to the Fc region of human IgG (R&D Systems, Cat. No. 726-R2) was coated at a concentration of 2 μg/mL. All subsequent steps were identical for both assays. In order to detect binding of TNFα to TNFRI and TNFRII, TNFα was biotinylated prior to its use. Biotinylated human TNFα (960 pM, 50 ng/mL) was first incubated with 3-fold serially diluted humanized anti-TNFα scFvs and infliximab (10'000 ng/mL-0.2 ng/mL) for 1 hour at room temperature. The TNFα/antibody fragment mixtures were transferred to the TNF receptor immobilized plates and binding of unblocked TNFα to the immobilized TNFα receptor was detected after incubation at room temperature for 20 minutes with the biotin-binding streptavidin-HRP (SDT Reagents, Cat. No. SP40C). Addition of 3',5,5'-tetramethylbenzidine (TMB) substrate resulted in a colorimetric read-out that was proportional to the binding of TNFα to TNFRI and TNFRII. Before use in the competition ELISA, the biological activity of the biotinylated TNFα was confirmed in the L929 assay. The EC$_{50}$ of biotinylated TNFα was similar to the EC$_{50}$ of unlabeled TNFα (data not shown). Similar to the L929 assay described above, data were analyzed using a four-parameter logistic curve fit using the Softmax Data Analysis Software (Molecular Devices), and the concentration of scFvs required to inhibit interaction of TNFα and TNFR by 50% and 90% (IC$_{50}$ and IC$_{00}$) was calculated. In order to render IC$_{50}$ and IC$_{90}$ values directly comparable between experiments that were performed on different days or on different assay plates, IC$_{50}$ and IC$_{90}$ values were calibrated against the reference antibody infliximab.

To control precision of the response, the dose-response curves were analyzed in duplicate. Standard deviations and CVs were calculated for each measurement point (CV<25%).

2.1.4 Target Specificity

To confirm specificity of the anti-TNFα scFvs, binding to the most homologous family member TNFβ was assessed. The potential to inhibit the interaction of biotinylated TNFα with scFvs by unlabeled TNFβ (Peprotech, Cat. No. 300-01B) and TNFα (Peprotech, Cat. No. 300-01) was analyzed by competition ELISA. For this purpose, the scFvs were coated on a 96-well Maxisorp ELISA plate at a concentration of 1 µg/mL. Binding of biotinylated TNFα (75 ng/mL) to the coated scFvs in presence of 5-fold serially diluted unlabeled TNFα (50 µg/mL-0.00013 µg/mL) or TNFβ (1250 µg/mL-0.00013 µg/mL) was detected using the biotin-binding streptavidin-HRP (SDT Reagents, Cat. No. SP40C) as described above. For the dose-response curve with TNFα data were analyzed using a four-parameter logistic curve fit using the Softmax Data Analysis Software (Molecular Devices), and the concentration of unlabeled TNFα required to block the interaction of biotinylated TNFα with the coated scFv by 50% ($IC_{50}$) was calculated. TNFβ did not show any significant inhibition of the interaction between biotinylated TNFα and scFvs (see also FIG. 11). To quantify the relative potential of TNFβ as compared to TNFα to inhibit TNFα binding to each scFv the $IC_{50}$ to inhibit the interaction by TNFβ relative to TNFα was calculated. Since no significant inhibition was observed when using TNFβ at an approximately 5'000 to 20'000-fold higher concentration than the $IC_{50}$ of TNFα, the selectivity for binding to TNFα over TNFβ was determined to be significantly higher than 5'000 to 20'000-fold. To control precision of the response, the dose-response curves were analyzed in duplicate. Standard deviations and CVs were calculated for each measurement point (CV<25% for all but one of the TNFα/β concentrations tested). All scFv fulfilled this criterion.

2.2 CMC Analytics 2.2.1 Reducing SDS-PAGE

Sodium Dodecyl Sulfate Polyacrylamide Gel Electrophoresis (SDS-PAGE) is an analysis technique used for qualitative characterization and to control purity of proteins. According to the United States Pharmacopeia (USP) (USP Chapter 1056) analytical gel electrophoresis is an appropriate and routine method to identify and to assess the homogeneity of proteins in drug substances.

The method is used to quantify the amount of scFv product from *E. coli* lysates to derive the expression yield after fermentation. Another application of the method is to verify the identity of test substances based on their molecular weight with respect to the theoretical values. For supportive purposes this method is used to quantify the purity of test samples with respect to process-related impurities (host cell proteins) and product related impurities (degradation products or adducts).

The SDS-PAGE analyses were performed with commercially available precast gel system "Mini Protean" obtained from Bio-Rad Laboratories Inc. Humanized scFvs were analyzed on "Any kD" resolving gels (#456-9036). In both cases the Tris/Glycine buffer system recommended by the manufacturer was used. For the detection of protein bands either coomassie staining with SimplyBlue™ staining solution (Life Technologies Corp., #LC6060) or silver staining with the Pierce Silver Stain Kit (Thermo Fisher Scientific Inc., #24612) was employed. For the staining procedures the protocols of the respective supplier were followed.

The documentation and analysis of the stained protein gels was performed with the documentation system ChemiDoc XRS System (Bio-Rad Laboratories Inc., #170-8265) and software Image Lab, Version 4.0.1 (Bio-Rad Laboratories Inc., #170-9690).

Titer Determination of Lysate Samples

SDS-PAGE allows for specific detection of the protein of interest in the mixture of host cell proteins. A reference standard dilution series in the linear range of the method (which was determined in advance) was included on every gel. A linear regression of band intensities (measured by densitometry) versus nominal concentrations of the reference standard were used to calculate a standard curve, which in turn, was used to extrapolate scFv content in the sample.

The lysate samples of unknown product concentrations were loaded in different dilutions (at least 1:10 in dilution buffer) to have at least one scFv concentration in the linear range of the method. The product amount was calculated based on the measured band intensities of the scFv and the concentration was determined using the dilution factors of the sample preparation. The values were averaged for all samples that were within the linear range of the standard curve.

As an additional test of the suitability of the method for the quantification of lysate sample an inhibition/enhancement test was performed by spiking a lysate sample with a known amount of reference standard. Calculation of the spike recovery at a sample dilution of 1:10 in dilution buffer resulted in a value of 95.4% which is at the same level of precision as observed with the reference standard in dilution buffer. Thus, no significant matrix interference in cell lysates was observed and the method was deemed suitable for the quantification of scFv content in cell lysates.

Protein Purity and Content

To show the suitability of the method to determine the content and thereby also the purity of test samples, the lower limit of detection (LOD) for a reference scFv was determined visually (by identifying the protein band) at a nominal load of 0.02 µg, the evaluation of the intensity histogram of the respective lane shows a signal-to-noise ratio at this load of approximately 2. In addition, the linear range for the quantification was determined by analyzing the main bands densitometrically.

The fit of the data with a linear regression, results in a coefficient of determination ($R^2$) of 0.9998, thus indicating a good quality of the fit. In addition to the overall quality of the fit the relative error of each individual data point was determined to document the suitability of the method in the chosen range. The relative errors are below 10% for all data points indicating good accuracy of this method.

2.2.2 UV Absorbance at 280 nm

The method UV absorbance at 280 nm is a total protein assay as outlined in USP Chapter 1057. Protein solutions absorb UV light at a wavelength of 280 nm due to the presence of aromatic amino acids. The UV absorbance is a function of the content of tyrosine and tryptophan residues in the protein and is proportional to the protein concentration. The absorbance of an unknown protein solution can be determined according to USP Chapter 851 on spectroscopy by applying Beer's law: $A=\varepsilon*l*c$, where the absorbance (A) is equal to the product of the molar absorptivity ($\varepsilon$), the absorption path length and the concentration of the substance. The molar absorptivity for the scFv was calculated with the software Vector NTI® (Life Technologies Corporation).

The measurement of the UV absorbance was performed with the Infinity reader M200 Pro equipped with Nanoquant plate (Tecan Group Ltd.). The absorbance of the protein samples were measured at 280 nm and 310 nm, where the latter wavelength was serving as a reference signal that was subtracted from the 280 nm signal. To account for potential interference of the sample matrix a blank subtraction was performed for each measurement.

The final absorbance signal of a protein sample obtained was used to calculate the protein concentration using Lambert-Beer's law.

All measurements were performed within the range given by the instruments specifications in the measurement range of 0-4 OD, where a reproducibility of <1% and a uniformity of <3% is specified by the manufacturer.

2.2.3 SE-HPLC (Size Exclusion High-Pressure Liquid Chromatography)

SE-HPLC is a separation technique based on a solid stationary phase and a liquid mobile phase as outlined by the USP chapter 621. This method separates molecules based on their size and shape utilizing a hydrophobic stationary phase and aqueous mobile phase. The separation of molecules is occurring between the void volume ($V_0$) and the total permeation volume ($V_T$) of a specific column. Measurements by SE-HPLC were performed on a Chromaster HPLC system (Hitachi High-Technologies Corporation) equipped with automated sample injection and a UV detector set to the detection wavelength of 280 nm. The equipment is controlled by the software EZChrom Elite (Agilent Technologies, Version 3.3.2 SP2) which also supports analysis of resulting chromatograms. Protein samples were cleared by centrifugation and kept at a temperature of 6° C. in the autosampler prior to injection. For the analysis of scFv samples the column Shodex KW402.5-4F (Showa Denko Inc., #F6989201) was employed with a standardized buffered saline mobile phase (50 mM Sodium acetate pH 6.0, 250 mM sodium chloride) at the recommended flow rate of 0.35 mL/min. The target sample load per injection was 5 µg. Samples were detected by an UV detector at a wavelength of 280 nm and the data recorded by a suitable software suite. The resulting chromatograms were analyzed in the range of $V_0$ to $V_T$ thereby excluding matrix associated peaks with >10 min elution time.

To ensure intermediate precision of the method, a reference standard was routinely measured at the beginning and end of each HPLC sequence. The reference standard used for this system suitability test was a scFv that had been produced as a batch and was aliquoted to be used for each measurement timepoint.

2.2.4 DSF (Differential Scanning Fluorimetry)

The method DSF is a non-compendial method to measure temperature-dependent protein unfolding. The measurement of the thermal unfolding temperature by DSF were performed with a MX3005P qPCR machine (Agilent Technologies) controlled with the MX Pro software package (Agilent Technologies) and equipped with an excitation/emission filter set at 492/610 nm. The reactions were set-up in Thermo fast 96 white PCR plates (Abgene; #AB-06001W). For the detection of protein unfolding a commercially available stock solution of the dye SYPRO orange (Molecular Probes; #S6650) was used at a final dilution of 1:1'000. The protein samples were diluted for the unfolding measurements to a final concentration of 50 µg/mL in a standardized buffered saline solution. The thermal unfolding was performed by a temperature program starting at 25° C. ramping up to 96° C. in 1° C. steps with a duration of 30 seconds. During the temperature program the fluorescence emission of each sample was recorded. The recorded raw data was processed and evaluated with a package of Microsoft Excel templates (Niesen, Nature Protocols 2007, Vol. 2 No. 9) and the fluorescence data was fitted with a Boltzmann equation using the program GraphPad Prism (GraphPad Software, Inc.) to obtain the midpoint of transition ($T_m$).

In order to produce reliable and robust measurements of the midpoint of unfolding at least duplicate measurements were performed. With respect to the data quality only measurements with a goodness of fit ($R^2$) >0.9900 and a 95% confidence interval of the $T_m$ of smaller than 0.5% were considered.

For an assessment of the intermediate precision a reference standard (known characterized scFv) was included with every measurement to allow for comparison of assay performance on different days.

2.2.5 Stability Study

In order to assess the stability of different scFv constructs as a read-out for the developability of these molecules a short-term stability study protocol was designed. The protein constructs were concentrated in a simple buffered saline formulation (see above) to the target concentrations of 1 and 10 mg/mL. The monomer content was determined by SE-HPLC to confirm that the purity is exceeding the success criteria of >95%. Subsequently the protein samples were stored at <−65, −20, 4 and 37° C. for the duration of 4 weeks and aliquots were analyzed at various time points. The primary read-out is the analysis by SE-HPLC, which allows the quantification of soluble higher molecular weight oligomers and aggregates. As supportive measurements the protein content is determined by UV absorbance at 280 nm, which gives an indication whether during the storage period substantial amounts of protein were lost by precipitation. For the storage screw cap tubes were used (Sarstedt, Cat. No. 72.692.005) with filling amounts of 30-1500 µg per aliquot. Additionally purity is determined by SDS-PAGE that indicates the stability of the construct with respect to degradation or covalent multimerization.

Example 3: Generation of Humanized Diabody and IgG

The single-chain diabody construct is designed by arranging the variable domains in a VLA-L1-VHB-L2-VLB-L3-VHA configuration. In these constructs the VLA and VHA and VLB and VHB domains jointly form the binding site for TNFα. The peptide linkers L1-L3 connecting the variable domains are constructed of glycine/serine repeats. The two short linkers L1 and L3 are composed of a single $G_4S$ (SEQ ID NO:30) repeat, whereas the long linker L2 is composed of the sequence $(G_4S)_4$ (SEQ ID NO:29). The nucleotide sequences encoding the humanized variable domains (Example 2; 1.2.1.) are de novo synthesized and cloned into an adapted vector for E. coli expression that is based on a pET26b(+) backbone (Novagen). The expression and purification is performed as described for the scFvs in Example 2; 1.2.1.

The humanized IgG was constructed by cloning the variable domains a suitable mammalian expression vector for transient heterologous expression containing a leader sequence and the respective constant domains e.g. the pFUSE-rIgG vectors (Invivogen). The transient expression of the functional IgG is performed by co-transfection of vectors encoding the heavy and light chains with the FreeStyle™ MAX system in CHO S cells. After cultivation for several days the supernatant of the antibody secreting cells is recovered for purification. Subsequently the secreted IgGs are affinity purified by Protein A sepharose (GE Healthcare). The elution fractions are analyzed by SDS-PAGE, UV absorbance at 280 nm and SE-HPLC.

The affinities of the antibody molecules are determined using a Biacore instrument as described in Example 2 under 2.1.1).

The potencies of the antibody molecules are determined in an L929 assay (the method is described in Example 2 under 2.1.2).

Example 4: Determination of Stoichiometry of TNFα Binding

The binding stoichiometry of 17-22-B03 to TNFα was determined using SE-HPLC. 17-22-B03-scFv and TNFα were incubated at two different molar ratios, namely at a 1:1 and 4.5:1 molar ratio. Since TNFα exists as a trimer in solution the indicated molar ratios refer to the $TNFα_{trimer}$. Thus, in the 4.5:1 ratio the 17-22-B03-scFv is in excess and should occupy all $TNFα_{trimer}$ binding positions resulting in complexes of 1 $TNFα_{trimer}$ with 3 scFv. However, under equimolar conditions there is not enough scFv present to saturate all 3 theoretical TNFα binding sites. Therefore, also complex variants with less than 3 scFv bound are expected. TNFα and 17-22-B03-scFv were incubated for 2 hours at RT to allow for complex formation. Samples were then centrifuged at 4° C. for 10 min. 10 µL of each sample were analysed on SE-HPLC. The SE-HPLC analysis was performed with 50 mM phosphate buffer pH 6.5, 300 mM NaCl as eluent at a flow rate of 0.35 mL/min. Eluted protein peaks were detected at a wavelength of 280 nm. The column was calibrated using the Gel filtration Calibration Kit from GE Healthcare (LMW, HMW) in advance for the determination of apparent molecular weights.

The bottom panel of FIG. 12 shows the elution profile with equimolar amounts of scFv and TNFα which is overlayed with the profiles of $TNFα_{trimer}$ alone and scFv alone. Due to the trimerization of the TNFα in solution there are theoretically up to three equivalent binding sites for the scFv present on each trimer and hence the scFv molecules are limiting. Under these conditions all three complex species (3:1, 2:1, 1:1) were identified. The top panel of FIG. 12 shows the elution profile of the complex with excess amounts of scFv. The surplus of unbound scFv eluted at the expected retention time. The TNFα peak was quantitatively consumed for complex formation and disappeared completely. The peak of this complex shifted towards lower retention times, and correlated well with the retention time of the peak with the largest molecular weight of the equimolar setup. For this reason it was concluded that all available binding sites on the TNFα were occupied by scFv and thus, the binding stoichiometry is 3:1 (scFv:TNFα) if the scFv is available in excess.

Further to these qualitative observations, the apparent binding stoichiometry was also calculated based on the apparent MW of the 17-22-B03-scFv:TNFα complex as determined by SE-HPLC. Based on retention time, the apparent MW was calculated to be 149.2 kDa. According to equation (1) below the apparent binding stoichiometry was calculated to be 3.6. This correlates well with the theoretical number of three equivalent binding sites available for scFv on the $TNFα_{trimer}$ and the observations above where a 3:1 binding stoichiometry was determined.

$$\text{binding stochiometry } (scFv:TNFα) = \frac{MW(\text{complex } app) - MW(TNFα\ theo)}{MW(scFv\ theo)} \quad \text{Equation (1)}$$

MW (complex app): 149.2 kDa
MW (TNFα theo): 52.2 kDa
MW (scFv theo): 26.5 kDa

Example 5: Formation of TNFα:Antibody Complexes (Cross-Linking of TNFα)

The ability of 17-22-B03-diabody to bind simultaneously to two TNFα molecules is tested on a Biacore T200 instrument in HEPES buffer containing 10 mM HEPES, 150 mM NaCl and 0.05% Tween. Biotinylated TNFα (Acro Biosystems) is captured via a biotinylated ssDNA oligo using the Biotin CAPture kit (GE Healthcare) according to the manufacturer's instructions. 0.25 µg/mL of biotinylated TNFα are injected with a flow rate of 10 µL/min for 3 min to reach a capture level of approximately 200 to 300 RUs (resonance units). The diabody and a 17-22-B03-scFv, as a control, are injected over the TNFα immobilized surface for 2 min at a flow rate of 30 µL/min at a concentration of 90 nM. Following association of the antibody fragments, TNFα (Peprotech) is injected for 5 min with a flow rate of 30 µL/min at 90 nM. The antibody and TNFα concentrations are selected close to saturation of the binding. The measurement is performed at 25° C. The bivalent 17-22-B03-diabody is is expected to bind two TNFα molecules simultaneously while, as expected, the monovalent 17-22-B03-scFv binds only to one TNFα molecule.

Further, the formation of TNFα-antibody complexes can be assessed at different ratios of TNFα and 17-22-B03 antibody formats using SE-HPLC. 17-22-B03-IgG (150 kDa) and 17-22-B03-scDb (~52 kDa) are incubated with TNFα (52 kDa) at different molar ratios (1:3, 1:1, 3:1) in respect to binding sites. Thus, IgG and scDb have 2 and TNFα has 3 binding sites. The antibody-TNFα mixtures are incubated for at least 30 min at 37° C., cooled down for 10 min at RT and stored overnight at 2-8° C. Five to 10 uL of protein mixture at a concentration of approx. 1 mg/mL are injected onto a TOSHO TSKgel UP-SW3000 column. The analysis is performed with 150 mM phosphate buffer pH 6.8, 100 mM NaCl as eluent at a flow rate of 0.3 mL/min. Eluted protein peaks are detected at a wavelength of 214 nm. The column is calibrated using the BEH450 SEC protein standard mix (Waters) in advance for the determination of the approximate molecular weights of the complexes. Complexes that are ≥600 kDa indicate the formation of complexes consisting of ≥2 TNFα and ≥3 IgG molecules. Complexes that are ≥300 kDa indicate the formation of complexes consisting of ≥2 TNFα and ≥3 scDb molecules.

Example 6: Inhibition of Cell Proliferation

The capacity of different antibody formats of 17-22-B03 and adalimumab to inhibit the proliferation of peripheral blood mononuclear cells (PBMC) is tested in a mixed lymphocyte reaction (MLR). PBMC from 2 healthy donors are cultured (RPMI1640) in a 1:1 ratio in 96-well plates for 48 h at 37° C./5% $CO_2$. After activation, cells are treated with anti-TNFα antibodies or IgG control antibody (all at a final concentration of 10 µg/mL) in sextuplicates for another 5 d at 37° C./5% $CO_2$. 24 h before the end of incubation BrdU (20 uL/well) is added to each well and proliferation is determined by measuring BrdU uptake using a commercially available cell proliferation ELISA (Roche Diagnostics). The stimulation index is determined by calculating the ratio of BrdU uptake between the antibody treated cells and mitomycin C (25 ng/mL) treated cells. All tested antibody formats of 17-22-B03 are expected to significantly inhibit T-cell proliferation comparable to adalimumab.

Example 7: Inhibition of LPS-Induced Cytokine Secretion $CD14^+$ monocytes in RPMI1640 are seeded in 96-well plates and incubated for 16 h at 37° C./5% $CO_2$ in a humidified incubator. Then cells are treated with anti-TNFα antibodies or IgG control antibody in duplicates for 1 h using final antibody concentrations ranging from 2 to 2000 ng/mL. The monocytes are washed 3 times with cell culture medium and subsequently incubated with LPS (100 ng/mL) for 4 h at 37° C./5% $CO_2$. IL-1β and TNFα concentrations in the cell culture supernatants are determined using commercially available ELISA kits (R&D Systems). $IC_{50}$ is determined using a four-parameter logistic curve fit.

TABLE 10

Vκ1 consensus sequences (rearranged)

| | Positions according to Kabat: | SEQ ID NO: | Sequence |
|---|---|---|---|
| Framework I | 1 to 23 | 31 | DIQMTQSPSSLSASVGDRVTITC |
| Framework II | 35 to 49 | 32 | WYQQKPGKAPKLLIY |
| Framework III | 57 to 88 | 33 | GVPSRFSGSGSGTDFTLTISSLQPEDFATYYC |

TABLE 11

Vλ germline-based framework IV sequences

| SEQ ID NO: | Sequence |
|---|---|
| 34 | FGTGTKVTVL |
| 35 | FGGGTKLTVL |
| 36 | FGGGTQLIIL |
| 37 | FGSGTKVTVL |

The invention claimed is:

1. An antibody or a functional fragment thereof capable of binding to human tumor necrosis factor alpha (TNFα), wherein said antibody or functional fragment comprises:
   i. a $V_L$ domain comprising a CDR1 region having an amino acid sequence as shown in SEQ ID NO: 7, a CDR2 region having an amino acid sequence as shown in SEQ ID NO: 8, and a CDR3 region having an amino acid sequence as shown in SEQ ID NO: 9, and
   ii. a $V_H$ domain comprising a CDR1 region having an amino acid sequence as shown in SEQ ID NO: 10, a CDR2 region having an amino acid sequence as shown in SEQ ID NO: 11, and a CDR3 region having an amino acid sequence as shown in SEQ ID: 6.

2. The antibody or functional fragment of claim 1, wherein said antibody or functional fragment
   (i) binds to human TNFα with a dissociation constant ($K_D$) of less than 100 pM;
   (ii) is cross-reactive with Macaca mulatta (Rhesus) TNFα and with Macaca fascicularis (Cynomolgus) TNFα;
   (iii) has a greater potency to inhibit TNFα-induced apoptosis than infliximab, as determined by an L929 assay;
   (iv) comprises a variable domain having a melting temperature, determined by differential scanning fluorimetry, of at least 70° C. and/or
   (v) is capable of binding to human $TNFα_{Trimer}$ in a stoichiometry (antibody: $TNFα_{Trimer}$) of at least 2.

3. The antibody or functional fragment of claim 1, wherein said antibody or functional fragment binds to human TNFα with a $K_D$ of less than 70 pM.

4. The antibody or functional fragment of claim 1, wherein said antibody or functional fragment comprises a $V_H$ domain having the amino acid sequence as shown in SEQ ID NO:21.

5. The antibody or functional fragment of claim 1, wherein said antibody or functional fragment comprises a $V_L$ domain having an amino acid sequence selected from the group consisting of SEQ ID NO: 22 and SEQ ID NO: 23.

6. The antibody or functional fragment of claim 1, wherein said antibody or functional fragment is a single-chain variable fragment (scFv).

7. The antibody or functional fragment of claim 6, wherein said scFv has an amino acid sequence selected from the group consisting of SEQ ID NO:25, SEQ ID NO:26 and SEQ ID NO:27.

8. The antibody or functional fragment of claim 1, wherein said antibody or functional fragment is an immunoglobulin G (IgG).

9. The antibody or functional fragment of claim 1, wherein the sum of (i) the number of amino acids in framework regions I, II, and III of the variable light domain of said antibody or functional fragment that are different from the respective human Vκ1 consensus sequences SEQ ID NOs: 31, 32, and 33, respectively, and (ii) the number of amino acids in framework region IV of the variable light domain of said antibody or functional fragment that are different from the most similar human λ germline-based sequence selected from SEQ ID NOs: 34, 35, 36, and 37, is less than 7.

10. The antibody or functional fragment of claim 1, wherein the framework regions I, II, and III of the variable light domain of said antibody or functional fragment consist of human Vκ1 consensus sequences with SEQ ID NOs:31, 32, and 33, respectively, and framework region IV consists of a λ germline-based sequence selected from among SEQ ID NOs:34, 35, 36, and 37.

11. A nucleic acid encoding the antibody or functional fragment of claim 1.

12. A vector or plasmid comprising the nucleic acid of claim 11.

13. A cell comprising the nucleic acid of claim 11 or a vector or plasmid comprising said nucleic acid.

14. A method of preparing the antibody or functional fragment of claim 1, comprising the steps of: culturing a cell comprising a nucleic acid encoding the antibody or functional fragment of claim 1 or a vector or plasmid comprising said nucleic acid in a medium under conditions that allow expression of the nucleic acid encoding the antibody or functional fragment, and recovering the antibody or functional fragment from the cells or from the medium.

15. A pharmaceutical composition comprising the antibody or functional fragment of claim 1 in combination with an optional pharmaceutically acceptable carrier and/or excipient.

16. A method of treating an inflammatory disorder or a TNFα-related disorder in a subject in need thereof, said method comprising the step of administering the pharmaceutical composition of claim 15 to said subject.

17. The method according to claim 16, wherein said inflammatory disorder is an inflammatory disorder of the gastrointestinal tract.

18. The method according to claim 17, wherein said inflammatory disorder of the gastrointestinal tract is inflammatory bowel disease.

19. The method according to claim 17, wherein said inflammatory disorder of the gastrointestinal tract is Crohn's disease or ulcerative colitis.

20. The antibody or functional fragment of claim 1, wherein the sum of (i) the number of amino acids in framework regions I, II, and III of the variable light domain of said antibody or functional fragment that are different from the respective human Vκ1 consensus sequences SEQ ID NOs: 31, 32, and 33, respectively, and (ii) the number of amino acids in framework region IV of the variable light domain of said antibody or functional fragment that are different from the most similar human λ germline-based sequence selected from SEQ ID NOs: 34, 35, 36, and 37, is less than 4.

* * * * *

SEQUENCE LISTING

```
<160> NUMBER OF SEQ ID NOS: 37

<210> SEQ ID NO 1
<211> LENGTH: 11
<212> TYPE: PRT
<213> ORGANISM: Artificial Sequence
<220> FEATURE:
<223> OTHER INFORMATION: Generic CDR L1
<220> FEATURE:
<221> NAME/KEY: MISC_FEATURE
<222> LOCATION: (7)..(7)
<223> OTHER INFORMATION: Xaa is Ser or Gly
<220> FEATURE:
<221> NAME/KEY: MISC_FEATURE
<222> LOCATION: (8)..(8)
<223> OTHER INFORMATION: Xaa is Ser or Asn
<220> FEATURE:
<221> NAME/KEY: MISC_FEATURE
<222> LOCATION: (11)..(11)
<223> OTHER INFORMATION: Xaa is Ala or Ser

<400> SEQUENCE: 1

Gln Ala Ser Gln Ser Ile Xaa Xaa Tyr Leu Xaa
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Generic CDR L2
<220> FEATURE:
<221> NAME/KEY: MISC_FEATURE
<222> LOCATION: (1)..(1)
<223> OTHER INFORMATION: Xaa is Arg, Gln or Lys

<400> SEQUENCE: 2

Xaa Ala Ser Thr Leu Ala Ser
1               5

<210> SEQ ID NO 3
<211> LENGTH: 13
<212> TYPE: PRT
<213> ORGANISM: Artificial Sequence
<220> FEATURE:
<223> OTHER INFORMATION: Generic CDR L3
<220> FEATURE:
<221> NAME/KEY: misc_feature
<222> LOCATION: (2)..(2)
<223> OTHER INFORMATION: Xaa can be any naturally occurring amino acid
```

```
<400> SEQUENCE: 3

Gln Xaa Thr Tyr Tyr Glu Pro Ser Tyr Val Phe Arg Ala
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Generic CDR H1
<220> FEATURE:
<221> NAME/KEY: MISC_FEATURE
<222> LOCATION: (1)..(1)
<223> OTHER INFORMATION: Xaa is Arg or Gly

<400> SEQUENCE: 4

Xaa Ile Asp Phe Ser Ala Gly Tyr Asp Met Cys
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Generic CDR H2
<220> FEATURE:
<221> NAME/KEY: MISC_FEATURE
<222> LOCATION: (6)..(6)
<223> OTHER INFORMATION: Xaa is Arg, Asn or Ser
<220> FEATURE:
<221> NAME/KEY: MISC_FEATURE
<222> LOCATION: (7)..(7)
<223> OTHER INFORMATION: Xaa is Asp or Glu
<220> FEATURE:
<221> NAME/KEY: MISC_FEATURE
<222> LOCATION: (8)..(8)
<223> OTHER INFORMATION: Xaa is Asn, Asp or Glu
<220> FEATURE:
<221> NAME/KEY: MISC_FEATURE
<222> LOCATION: (9)..(9)
<223> OTHER INFORMATION: Xaa is Ser or Thr

<400> SEQUENCE: 5

Cys Ile Asp Ser Arg Xaa Xaa Xaa Xaa Asp Tyr Ala Ser Trp Ala Lys
1               5                   10                  15

Gly

<210> SEQ ID NO 6
<211> LENGTH: 14
<212> TYPE: PRT
<213> ORGANISM: Artificial Sequence
<220> FEATURE:
<223> OTHER INFORMATION: CDR H3 of clones 17-22-B03, 16-12-E09,
      16-13-E01, 16-15-E11, 16-17-C08, 16-17-G01, 17-18-D10 and
      17-22-B01

<400> SEQUENCE: 6

Gly Gly Tyr Gly Gly Asp Gly Val Asp Gly Ala Phe Asp Pro
1               5                   10

<210> SEQ ID NO 7
<211> LENGTH: 11
<212> TYPE: PRT
<213> ORGANISM: Artificial Sequence
<220> FEATURE:
<223> OTHER INFORMATION: CDR L1 of clones 17-22-B03, 16-12-E09,
      16-13-E01, 16-15-E11 and 17-18-D10
```

```
<400> SEQUENCE: 7

Gln Ala Ser Gln Ser Ile Ser Ser Tyr Leu Ala
1               5                   10

<210> SEQ ID NO 8
<211> LENGTH: 7
<212> TYPE: PRT
<213> ORGANISM: Artificial Sequence
<220> FEATURE:
<223> OTHER INFORMATION: CDR L2 of clones 17-22-B03, 16-12-E09,
      16-15-E11, 16-17-C08, 16-17-G01 and 17-18-D10

<400> SEQUENCE: 8

Lys Ala Ser Thr Leu Ala Ser
1               5

<210> SEQ ID NO 9
<211> LENGTH: 13
<212> TYPE: PRT
<213> ORGANISM: Artificial Sequence
<220> FEATURE:
<223> OTHER INFORMATION: CDR L3 of clones 17-22-B03, 16-12-E09,
      16-13-E01, 16-15-E11, 16-17-C08, 16-17-G01, 17-18-D10 and
      17-22-B01

<400> SEQUENCE: 9

Gln Cys Thr Tyr Tyr Glu Pro Ser Tyr Val Phe Arg Ala
1               5                   10

<210> SEQ ID NO 10
<211> LENGTH: 11
<212> TYPE: PRT
<213> ORGANISM: Artificial Sequence
<220> FEATURE:
<223> OTHER INFORMATION: CDR H1 of clones 17-22-B03, 16-12-E09,
      16-13-E01, 16-15-E11, 16-17-C08, 17-18-D10 and 17-22-B01

<400> SEQUENCE: 10

Gly Ile Asp Phe Ser Ala Gly Tyr Asp Met Cys
1               5                   10

<210> SEQ ID NO 11
<211> LENGTH: 17
<212> TYPE: PRT
<213> ORGANISM: Artificial Sequence
<220> FEATURE:
<223> OTHER INFORMATION: CDR H2 of clones 17-22-B03 and 16-17-C08

<400> SEQUENCE: 11

Cys Ile Asp Ser Arg Arg Glu Glu Ser Asp Tyr Ala Ser Trp Ala Lys
1               5                   10                  15

Gly

<210> SEQ ID NO 12
<211> LENGTH: 17
<212> TYPE: PRT
<213> ORGANISM: Artificial Sequence
<220> FEATURE:
<223> OTHER INFORMATION: CDR H2 of clone 16-12-E09

<400> SEQUENCE: 12

Cys Ile Asp Ser Arg Ser Asp Asn Thr Asp Tyr Ala Ser Trp Ala Lys
1               5                   10                  15

Gly
```

```
<210> SEQ ID NO 13
<211> LENGTH: 7
<212> TYPE: PRT
<213> ORGANISM: Artificial Sequence
<220> FEATURE:
<223> OTHER INFORMATION: CDR L2 of clone 16-13-E01

<400> SEQUENCE: 13

Gln Ala Ser Thr Leu Ala Ser
1               5

<210> SEQ ID NO 14
<211> LENGTH: 17
<212> TYPE: PRT
<213> ORGANISM: Artificial Sequence
<220> FEATURE:
<223> OTHER INFORMATION: CDR H2 of clones 16-13-E01 and 17-18-D10

<400> SEQUENCE: 14

Cys Ile Asp Ser Arg Arg Glu Asp Ser Asp Tyr Ala Ser Trp Ala Lys
1               5                   10                  15

Gly

<210> SEQ ID NO 15
<211> LENGTH: 17
<212> TYPE: PRT
<213> ORGANISM: Artificial Sequence
<220> FEATURE:
<223> OTHER INFORMATION: CDR H2 of clones 16-15-E11, 16-17-G01 and
      17-22-B01

<400> SEQUENCE: 15

Cys Ile Asp Ser Arg Asn Asp Asn Thr Asp Tyr Ala Ser Trp Ala Lys
1               5                   10                  15

Gly

<210> SEQ ID NO 16
<211> LENGTH: 11
<212> TYPE: PRT
<213> ORGANISM: Artificial Sequence
<220> FEATURE:
<223> OTHER INFORMATION: CDR L1 of clone 16-17-C08

<400> SEQUENCE: 16

Gln Ala Ser Gln Ser Ile Gly Ser Tyr Leu Ala
1               5                   10

<210> SEQ ID NO 17
<211> LENGTH: 11
<212> TYPE: PRT
<213> ORGANISM: Artificial Sequence
<220> FEATURE:
<223> OTHER INFORMATION: CDR L1 of clone 16-17-G01

<400> SEQUENCE: 17

Gln Ala Ser Gln Ser Ile Ser Asn Tyr Leu Ala
1               5                   10

<210> SEQ ID NO 18
<211> LENGTH: 11
<212> TYPE: PRT
<213> ORGANISM: Artificial Sequence
<220> FEATURE:
<223> OTHER INFORMATION: CDR H1 of clone 16-17-G01
```

<400> SEQUENCE: 18

Arg Ile Asp Phe Ser Ala Gly Tyr Asp Met Cys
1               5                   10

<210> SEQ ID NO 19
<211> LENGTH: 11
<212> TYPE: PRT
<213> ORGANISM: Artificial Sequence
<220> FEATURE:
<223> OTHER INFORMATION: CDR L1 of clone 17-22-B01

<400> SEQUENCE: 19

Gln Ala Ser Gln Ser Ile Ser Ser Tyr Leu Ser
1               5                   10

<210> SEQ ID NO 20
<211> LENGTH: 7
<212> TYPE: PRT
<213> ORGANISM: Artificial Sequence
<220> FEATURE:
<223> OTHER INFORMATION: CDR L2 of clone 17-22-B01

<400> SEQUENCE: 20

Arg Ala Ser Thr Leu Ala Ser
1               5

<210> SEQ ID NO 21
<211> LENGTH: 124
<212> TYPE: PRT
<213> ORGANISM: Artificial Sequence
<220> FEATURE:
<223> OTHER INFORMATION: VH of humanized scFv of clones 17-22-B03-sc02,
      17-22-B03-sc08, 17-22-B03-sc12

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Lys Ala Ser Gly Ile Asp Phe Ser Ala Gly
            20                  25                  30

Tyr Asp Met Cys Trp Val Arg Gln Ala Pro Gly Lys Gly Leu Glu Trp
        35                  40                  45

Ile Ala Cys Ile Asp Ser Arg Arg Glu Glu Ser Asp Tyr Ala Ser Trp
    50                  55                  60

Ala Lys Gly Arg Phe Thr Ile Ser Lys Asp Ser Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Gly Gly Tyr Gly Gly Asp Gly Val Asp Gly Ala Phe Asp
            100                 105                 110

Pro Trp Gly Gln Gly Thr Leu Val Thr Val Ser Ser
        115                 120

<210> SEQ ID NO 22
<211> LENGTH: 112
<212> TYPE: PRT
<213> ORGANISM: Artificial Sequence
<220> FEATURE:
<223> OTHER INFORMATION: VL of humanized scFv of clone 17-22-B03-sc02

```
<400> SEQUENCE: 22

Asp Ile Gln Met Thr Gln Ser Pro Ser Ser Leu Ser Ala Ser Val Gly
1               5                   10                  15

Asp Arg Val Thr Ile Lys Cys Gln Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
50                  55                  60

Ser Gly Ser Gly Thr Glu Phe Thr Leu Thr Ile Ser Asp Leu Glu Pro
65                  70                  75                  80

Ala Asp Phe Ala Thr Tyr Tyr Cys Gln Cys Thr Tyr Tyr Glu Pro Ser
                85                  90                  95

Tyr Val Phe Arg Ala Phe Gly Gly Gly Thr Lys Leu Thr Val Leu Gly
            100                 105                 110

<210> SEQ ID NO 23
<211> LENGTH: 112
<212> TYPE: PRT
<213> ORGANISM: Artificial Sequence
<220> FEATURE:
<223> OTHER INFORMATION: VL of humanized scFv of clone 17-22-B03-sc08

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Cys Thr Tyr Tyr Glu Pro Ser
                85                  90                  95

Tyr Val Phe Arg Ala Phe Gly Gly Gly Thr Lys Leu Thr Val Leu Gly
            100                 105                 110

<210> SEQ ID NO 24
<211> LENGTH: 112
<212> TYPE: PRT
<213> ORGANISM: Artificial Sequence
<220> FEATURE:
<223> OTHER INFORMATION: VL of humanized scFv of clone 17-22-B03-sc12

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Ser Thr Tyr Tyr Glu Pro Ser
                85                  90                  95

Tyr Val Phe Arg Ala Phe Gly Gly Gly Thr Lys Leu Thr Val Leu Gly
            100                 105                 110
```

<210> SEQ ID NO 25
<211> LENGTH: 257
<212> TYPE: PRT
<213> ORGANISM: Artificial Sequence
<220> FEATURE:
<223> OTHER INFORMATION: Humanized scFv of clone 17-22-B03-sc02

<400> SEQUENCE: 25

```
Met Asp Ile Gln Met Thr Gln Ser Pro Ser Ser Leu Ser Ala Ser Val
1               5                   10                  15

Gly Asp Arg Val Thr Ile Lys Cys Gln Ala Ser Gln Ser Ile Ser Ser
            20                  25                  30

Tyr Leu Ala Trp Tyr Gln Gln Lys Pro Gly Lys Ala Pro Lys Leu Leu
        35                  40                  45

Ile Tyr Lys Ala Ser Thr Leu Ala Ser Gly Val Pro Ser Arg Phe Ser
50                  55                  60

Gly Ser Gly Ser Gly Thr Glu Phe Thr Leu Thr Ile Ser Asp Leu Glu
65                  70                  75                  80

Pro Ala Asp Phe Ala Thr Tyr Tyr Cys Gln Cys Thr Tyr Tyr Glu Pro
                85                  90                  95

Ser Tyr Val Phe Arg Ala Phe Gly Gly Gly Thr Lys Leu Thr Val Leu
            100                 105                 110

Gly Gly Gly Gly Ser Gly Gly Gly Ser Gly Gly Gly Ser
            115                 120                 125

Gly Gly Gly Gly Ser Glu Val Gln Leu Val Glu Ser Gly Gly Gly Leu
            130                 135                 140

Val Gln Pro Gly Gly Ser Leu Arg Leu Ser Cys Lys Ala Ser Gly Ile
145                 150                 155                 160

Asp Phe Ser Ala Gly Tyr Asp Met Cys Trp Val Arg Gln Ala Pro Gly
                165                 170                 175

Lys Gly Leu Glu Trp Ile Ala Cys Ile Asp Ser Arg Arg Glu Glu Ser
            180                 185                 190

Asp Tyr Ala Ser Trp Ala Lys Gly Arg Phe Thr Ile Ser Lys Asp Ser
        195                 200                 205

Ser Lys Asn Thr Val Tyr Leu Gln Met Asn Ser Leu Arg Ala Glu Asp
    210                 215                 220

Thr Ala Val Tyr Tyr Cys Ala Arg Gly Gly Tyr Gly Gly Asp Gly Val
225                 230                 235                 240

Asp Gly Ala Phe Asp Pro Trp Gly Gln Gly Thr Leu Val Thr Val Ser
                245                 250                 255

Ser
```

<210> SEQ ID NO 26
<211> LENGTH: 257
<212> TYPE: PRT
<213> ORGANISM: Artificial Sequence
<220> FEATURE:
<223> OTHER INFORMATION: Humanized scFv of clone 17-22-B03-sc08

<400> SEQUENCE: 26

```
Met Asp Ile Gln Met Thr Gln Ser Pro Ser Ser Leu Ser Ala Ser Val
1               5                   10                  15

Gly Asp Arg Val Thr Ile Thr Cys Gln Ala Ser Gln Ser Ile Ser Ser
            20                  25                  30

Tyr Leu Ala Trp Tyr Gln Gln Lys Pro Gly Lys Ala Pro Lys Leu Leu
        35                  40                  45

Ile Tyr Lys Ala Ser Thr Leu Ala Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Cys Thr Tyr Tyr Glu Pro
                85                  90                  95

Ser Tyr Val Phe Arg Ala Phe Gly Gly Gly Thr Lys Leu Thr Val Leu
            100                 105                 110

Gly Gly Gly Gly Gly Ser Gly Gly Gly Ser Gly Gly Gly Gly Ser
            115                 120                 125

Gly Gly Gly Gly Ser Glu Val Gln Leu Val Glu Ser Gly Gly Gly Leu
            130                 135                 140

Val Gln Pro Gly Gly Ser Leu Arg Leu Ser Cys Lys Ala Ser Gly Ile
145                 150                 155                 160

Asp Phe Ser Ala Gly Tyr Asp Met Cys Trp Val Arg Gln Ala Pro Gly
                165                 170                 175

Lys Gly Leu Glu Trp Ile Ala Cys Ile Asp Ser Arg Arg Glu Glu Ser
            180                 185                 190

Asp Tyr Ala Ser Trp Ala Lys Gly Arg Phe Thr Ile Ser Lys Asp Ser
        195                 200                 205

Ser Lys Asn Thr Val Tyr Leu Gln Met Asn Ser Leu Arg Ala Glu Asp
    210                 215                 220

Thr Ala Val Tyr Tyr Cys Ala Arg Gly Gly Tyr Gly Gly Asp Gly Val
225                 230                 235                 240

Asp Gly Ala Phe Asp Pro Trp Gly Gln Gly Thr Leu Val Thr Val Ser
                245                 250                 255

Ser
```

<210> SEQ ID NO 27
<211> LENGTH: 257
<212> TYPE: PRT
<213> ORGANISM: Artificial Sequence
<220> FEATURE:
<223> OTHER INFORMATION: Humanized scFv of clone 17-22-B03-sc12

<400> SEQUENCE: 27

```
Met Asp Ile Gln Met Thr Gln Ser Pro Ser Ser Leu Ser Ala Ser Val
1               5                   10                  15

Gly Asp Arg Val Thr Ile Thr Cys Gln Ala Ser Gln Ser Ile Ser Ser
            20                  25                  30

Tyr Leu Ala Trp Tyr Gln Gln Lys Pro Gly Lys Ala Pro Lys Leu Leu
        35                  40                  45

Ile Tyr Lys Ala Ser Thr Leu Ala Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Ser Thr Tyr Tyr Glu Pro
                85                  90                  95
```

```
Ser Tyr Val Phe Arg Ala Phe Gly Gly Thr Lys Leu Thr Val Leu
                100                 105                 110

Gly Gly Gly Gly Ser Gly Gly Gly Ser Gly Gly Gly Ser
        115                 120                 125

Gly Gly Gly Ser Glu Val Gln Leu Val Glu Ser Gly Gly Leu
        130                 135                 140

Val Gln Pro Gly Gly Ser Leu Arg Leu Ser Cys Lys Ala Ser Gly Ile
145                 150                 155                 160

Asp Phe Ser Ala Gly Tyr Asp Met Cys Trp Val Arg Gln Ala Pro Gly
                165                 170                 175

Lys Gly Leu Glu Trp Ile Ala Cys Ile Asp Ser Arg Arg Glu Glu Ser
                180                 185                 190

Asp Tyr Ala Ser Trp Ala Lys Gly Arg Phe Thr Ile Ser Lys Asp Ser
                195                 200                 205

Ser Lys Asn Thr Val Tyr Leu Gln Met Asn Ser Leu Arg Ala Glu Asp
        210                 215                 220

Thr Ala Val Tyr Tyr Cys Ala Arg Gly Gly Tyr Gly Gly Asp Gly Val
225                 230                 235                 240

Asp Gly Ala Phe Asp Pro Trp Gly Gln Gly Thr Leu Val Thr Val Ser
                245                 250                 255

Ser

<210> SEQ ID NO 28
<211> LENGTH: 13
<212> TYPE: PRT
<213> ORGANISM: Artificial Sequence
<220> FEATURE:
<223> OTHER INFORMATION: Generic CDR L3 where Cys2 (Xaa) is limited to
      Arg, His, Pro, Phe, Gln, Gly or Tyr
<220> FEATURE:
<221> NAME/KEY: MISC_FEATURE
<222> LOCATION: (2)..(2)
<223> OTHER INFORMATION: Xaa is Arg, His, Pro, Phe, Gln, Gly or Tyr

<400> SEQUENCE: 28

Gln Xaa Thr Tyr Tyr Glu Pro Ser Tyr Val Phe Arg Ala
1               5                   10

<210> SEQ ID NO 29
<211> LENGTH: 20
<212> TYPE: PRT
<213> ORGANISM: Artificial Sequence
<220> FEATURE:
<223> OTHER INFORMATION: Linker sequence in scFv

<400> SEQUENCE: 29

Gly Gly Gly Gly Ser Gly Gly Gly Gly Ser Gly Gly Gly Gly Ser Gly
1               5                   10                  15

Gly Gly Gly Ser
            20

<210> SEQ ID NO 30
<211> LENGTH: 5
<212> TYPE: PRT
<213> ORGANISM: Artificial Sequence
<220> FEATURE:
<223> OTHER INFORMATION: Linker sequence in diabody

<400> SEQUENCE: 30

Gly Gly Gly Gly Ser
1               5
```

```
<210> SEQ ID NO 31
<211> LENGTH: 23
<212> TYPE: PRT
<213> ORGANISM: Artificial Sequence
<220> FEATURE:
<223> OTHER INFORMATION: Vk1 consensus sequence of framework I (Kabat
      positions 1-23)

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 32
<211> LENGTH: 15
<212> TYPE: PRT
<213> ORGANISM: Artificial Sequence
<220> FEATURE:
<223> OTHER INFORMATION: Vk1 consensus sequence of framework II (Kabat
      positions 35-49)

<400> SEQUENCE: 32

Trp Tyr Gln Gln Lys Pro Gly Lys Ala Pro Lys Leu Leu Ile Tyr
1               5                   10                  15

<210> SEQ ID NO 33
<211> LENGTH: 32
<212> TYPE: PRT
<213> ORGANISM: Artificial Sequence
<220> FEATURE:
<223> OTHER INFORMATION: Vk1 consensus sequence of framework III (Kabat
      positions 57-88)

<400> SEQUENCE: 33

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 34
<211> LENGTH: 10
<212> TYPE: PRT
<213> ORGANISM: Artificial Sequence
<220> FEATURE:
<223> OTHER INFORMATION: V lamda germline-based sequence of framework IV

<400> SEQUENCE: 34

Phe Gly Thr Gly Thr Lys Val Thr Val Leu
1               5                   10

<210> SEQ ID NO 35
<211> LENGTH: 10
<212> TYPE: PRT
<213> ORGANISM: Artificial Sequence
<220> FEATURE:
<223> OTHER INFORMATION: V lamda germline-based sequence of framework IV

<400> SEQUENCE: 35

Phe Gly Gly Gly Thr Lys Leu Thr Val Leu
1               5                   10

<210> SEQ ID NO 36
<211> LENGTH: 10
<212> TYPE: PRT
<213> ORGANISM: Artificial Sequence
```

```
<220> FEATURE:
<223> OTHER INFORMATION: V lamda germline-based sequence of framework IV

<400> SEQUENCE: 36

Phe Gly Gly Gly Thr Gln Leu Ile Ile Leu
1               5                   10

<210> SEQ ID NO 37
<211> LENGTH: 10
<212> TYPE: PRT
<213> ORGANISM: Artificial Sequence
<220> FEATURE:
<223> OTHER INFORMATION: V lamda germline-based sequence of framework IV

<400> SEQUENCE: 37

Phe Gly Ser Gly Thr Lys Val Thr Val Leu
1               5                   10
```